US011279688B2

(12) United States Patent
Brubaker et al.

(10) Patent No.: US 11,279,688 B2
(45) Date of Patent: Mar. 22, 2022

(54) INHIBITORS OF RET

(71) Applicant: BLUEPRINT MEDICINES CORPORATION, Cambridge, MA (US)

(72) Inventors: Jason D. Brubaker, Cambridge, MA (US); Joseph L. Kim, Wayland, MA (US); Kevin J. Wilson, Boston, MA (US); Douglas Wilson, Ayer, MA (US); Lucian V. DiPietro, Gloucester, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

(21) Appl. No.: 16/775,646

(22) Filed: Jan. 29, 2020

(65) Prior Publication Data
US 2020/0407341 A1 Dec. 31, 2020

Related U.S. Application Data

(63) Continuation of application No. 16/041,719, filed on Jul. 20, 2018, now Pat. No. 10,584,114, which is a continuation of application No. 15/340,428, filed on Nov. 1, 2016, now Pat. No. 10,030,005.

(60) Provisional application No. 62/367,960, filed on Jul. 28, 2016, provisional application No. 62/249,784, filed on Nov. 2, 2015.

(51) Int. Cl.
C07D 239/30 (2006.01)
C07D 239/36 (2006.01)
C07D 401/14 (2006.01)
C07D 403/14 (2006.01)

(52) U.S. Cl.
CPC ......... C07D 401/14 (2013.01); C07D 239/30 (2013.01); C07D 239/36 (2013.01); C07D 403/14 (2013.01)

(58) Field of Classification Search
CPC .................. C07D 239/30; C07D 239/36
See application file for complete search history.

(56) References Cited

U.S. PATENT DOCUMENTS

| | | |
|---|---|---|
| 8,802,697 B2 | 8/2014 | Bifulco, Jr. |
| 9,126,951 B2 | 9/2015 | Bifulco, Jr. |
| 9,187,475 B2 | 11/2015 | Kawamura et al. |
| 9,200,002 B2 | 12/2015 | Hodous et al. |
| 9,216,172 B2 | 12/2015 | Kohno et al. |
| 9,297,011 B2 | 3/2016 | Downing et al. |
| 9,334,263 B2 | 5/2016 | Hodous et al. |
| 9,340,514 B2 | 5/2016 | Bifulco, Jr. |
| 9,434,700 B2 | 9/2016 | Bifulco, Jr. |
| 9,499,522 B2 | 11/2016 | DiPietro et al. |
| 9,688,680 B2 | 6/2017 | Hodous |
| 9,695,165 B2 | 7/2017 | Bifulco, Jr. |
| 9,884,861 B2 | 2/2018 | Hodous et al. |
| 9,944,651 B2 | 4/2018 | Hodous et al. |
| 9,994,552 B2 | 6/2018 | DiPietro et al. |
| 9,994,575 B2 | 6/2018 | Hodous et al. |
| 10,000,490 B2 | 6/2018 | Bifulco, Jr. |
| 10,000,496 B2 | 6/2018 | Hodous et al. |
| 10,017,512 B2 | 7/2018 | Wenglowsky et al. |
| 10,030,005 B2 | 7/2018 | Brubaker et al. |
| 10,035,789 B2 | 7/2018 | Brubaker et al. |
| 10,183,928 B2 | 1/2019 | Kim et al. |
| 10,196,436 B2 | 2/2019 | Miduturu |
| 10,202,365 B2 | 2/2019 | Brooijmans et al. |
| 10,221,154 B2 | 3/2019 | Bifulco, Jr. et al. |
| 10,227,329 B2 | 3/2019 | Brubaker et al. |
| 10,584,114 B2 | 3/2020 | Brubaker et al. |
| 10,774,070 B2 | 9/2020 | Brooijmans et al. |
| 2012/0316137 A1 | 12/2012 | Huang et al. |
| 2013/0096136 A1 | 4/2013 | Hata et al. |
| 2013/0115313 A1 | 5/2013 | Charrier et al. |
| 2013/0116280 A1 | 5/2013 | Ju et al. |
| 2014/0187559 A1 | 7/2014 | Miduturu |
| 2014/0221404 A1 | 8/2014 | Kohno et al. |
| 2014/0243357 A1 | 8/2014 | Dar et al. |
| 2014/0272951 A1 | 9/2014 | Chakravarti et al. |
| 2015/0057335 A1 | 2/2015 | Kohno et al. |
| 2015/0177246 A1 | 6/2015 | Shibata et al. |
| 2016/0102097 A1 | 4/2016 | Hodous et al. |
| 2017/0014413 A1 | 1/2017 | Downing et al. |
| 2017/0022206 A1 | 1/2017 | Hodous et al. |
| 2017/0029409 A1 | 2/2017 | DiPietro et al. |
| 2017/0057953 A1 | 3/2017 | Hodous et al. |
| 2017/0066773 A1 | 3/2017 | Wenglowsky et al. |
| 2017/0066812 A1 | 3/2017 | Bifulco, Jr. |
| 2017/0121312 A1 | 5/2017 | Brubaker et al. |
| 2017/0145018 A1 | 5/2017 | Wenglowsky et al. |

(Continued)

FOREIGN PATENT DOCUMENTS

| | | |
|---|---|---|
| CN | 105255927 A | 1/2016 |
| EP | 3037547 A1 | 6/2016 |

(Continued)

OTHER PUBLICATIONS

W. Brandt et al., 45 European Journal of Medicinal Chemistry, 2919-2927 (2010).

(Continued)

Primary Examiner — Brian E McDowell
(74) Attorney, Agent, or Firm — Goodwin Procter LLP

(57) ABSTRACT

Described herein are compounds that inhibit wild-type RET and its resistant mutants, pharmaceutical compositions including such compounds, and methods of using such compounds and compositions.

2 Claims, No Drawings

(56) References Cited

U.S. PATENT DOCUMENTS

| | | |
|---|---|---|
| 2017/0174652 A1 | 6/2017 | Bifulco, Jr. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0281633 A1 | 10/2017 | Boylan et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |
| 2018/0030032 A1 | 2/2018 | Brubaker et al. |
| 2019/0185454 A1 | 6/2019 | Brubaker et al. |
| 2019/0192522 A1 | 6/2019 | Hagel et al. |
| 2021/0085680 A1 | 3/2021 | Evans Raab et al. |
| 2021/0100795 A1 | 4/2021 | Evans Raab et al. |
| 2021/0100799 A1 | 4/2021 | Evans Raab et al. |

FOREIGN PATENT DOCUMENTS

| | | |
|---|---|---|
| JP | 2015109806 A | 6/2015 |
| WO | WO-2001/60816 A1 | 8/2001 |
| WO | WO-2004/009087 A1 | 1/2004 |
| WO | WO-2005/062795 A2 | 7/2005 |
| WO | WO-2007/023382 A2 | 3/2007 |
| WO | WO-2007/087245 A2 | 8/2007 |
| WO | WO-2007/124221 A1 | 11/2007 |
| WO | WO-2008/061201 A1 | 5/2008 |
| WO | WO-2009/003136 A1 | 12/2008 |
| WO | WO-2009/007748 A2 | 1/2009 |
| WO | WO-2009/014637 A2 | 1/2009 |
| WO | WO-2009/100536 A1 | 8/2009 |
| WO | WO-2010/006432 A1 | 1/2010 |
| WO | WO-2011/060295 A1 | 5/2011 |
| WO | WO-2013/170159 A1 | 11/2013 |
| WO | WO-2014/039971 A1 | 3/2014 |
| WO | WO-2014/050781 A1 | 4/2014 |
| WO | WO-2014/072220 A1 | 5/2014 |
| WO | WO-2014/130810 A1 | 8/2014 |
| WO | WO-2014/141187 A1 | 9/2014 |
| WO | WO-2015/006875 A1 | 1/2015 |
| WO | WO-2015/079251 A1 | 6/2015 |
| WO | WO-2016/037578 A1 | 3/2016 |
| WO | WO-2016/038552 A1 | 3/2016 |
| WO | WO-2016/075224 A1 | 5/2016 |
| WO | WO-2016/127074 A1 | 8/2016 |
| WO | WO-2017/011776 A1 | 1/2017 |
| WO | WO-2017/079117 A1 | 5/2017 |
| WO | WO-2017/079121 A2 | 5/2017 |
| WO | WO-2017/079140 A1 | 5/2017 |
| WO | WO-2017/145050 A1 | 8/2017 |
| WO | WO-2017/161269 A1 | 9/2017 |
| WO | WO-2017/178844 A1 | 10/2017 |
| WO | WO-2017/178845 A1 | 10/2017 |
| WO | WO-2018/017983 A1 | 1/2018 |
| WO | WO-2018/022761 A1 | 2/2018 |
| WO | WO-2018/049233 A1 | 3/2018 |
| WO | WO-2018/060714 A1 | 4/2018 |
| WO | WO-2018/064852 A1 | 4/2018 |
| WO | WO-2018/071447 A1 | 4/2018 |
| WO | WO-2018/071454 A1 | 4/2018 |
| WO | WO-2018/102455 A1 | 6/2018 |
| WO | WO-2018/136661 A1 | 7/2018 |
| WO | WO-2018/136663 A1 | 7/2018 |
| WO | WO-2018/183712 A1 | 10/2018 |
| WO | WO-2018/189553 A1 | 10/2018 |
| WO | WO-2018/213329 A1 | 11/2018 |
| WO | WO-2018/237134 A1 | 12/2018 |
| WO | WO-2019/001556 A1 | 1/2019 |
| WO | WO-2019/008172 A1 | 1/2019 |
| WO | WO-2019/126121 A1 | 6/2019 |
| WO | WO-2019/143977 A1 | 7/2019 |
| WO | WO-2019/143991 A1 | 7/2019 |
| WO | WO-2019/143994 A1 | 7/2019 |
| WO | WO-2019/195471 A1 | 10/2019 |
| WO | WO-2020/033838 A2 | 2/2020 |

OTHER PUBLICATIONS

R. Graham et al., 17 Bioorganic & Medicinal Chemistry, 5886-5893 (2007).

Arighi, E. et al. (2005) "RET tyrosine kinase signaling in development and cancer" Cytokine & Growth Factor Reviews, 16:441-467.

International Search Report and Written Opinion dated Apr. 29, 2016, in International Patent Application No. PCT/US2016/016808, filed Feb. 5, 2016, by Blueprint Medicines Corp. (8 pages).

International Search Report and Written Opinion dated Jan. 18, 2017, in International Patent Application No. PCT/US2016/059879, filed Nov. 1, 2016, by Blueprint Medicines Corp. (12 pages).

International Search Report and Written Opinion dated Jun. 12, 2017, in International Patent Application No. PCT/US2017/022969, filed Mar. 17, 2017, by Blueprint Medicines Corp. (12 pages).

Mologni, L. et al. (2013) "Ponatinib is a potent inhibitor of wild-type and drug-resistant gatekeeper mutant RET kinase" Mol Cell Endocrinol, 377:1-6.

Mologni, L. et al. (2017) "RET kinase inhibitors: a review of recent patents (2012-2015)" Exp Opin Ther Patents, 27(1):91-99.

Plaza-Menacho, I. et al. (2014) "Mechanisms of RET signaling in cancer: Current and future implications for targeted therapy" Cellular Signalling, 26:1743-1752.

Abdel-Rahman, O. and M. Fouad (2014) "Risk of cardiovascular toxicities in patients with solid tumors treated with sunitinib, axitinib, cediranib or regorafenib: an updated systematic review and comparative meta-analysis" Crit Rev Oncol Hematol,92:194-207.

Bentzien, F. et al. (2013) "In Vitro and in Vivo Activity of Cabozantinib (XL184), an Inhibitor of RET, MET, and VEGFR2, in a Model of Medullary Thyroid Cancer" Thyroid, 23(12):1569-1577.

Carlomagno, F. et al. (Feb. 1995) "Point Mutation of the Ret Proto-oncogene in the TT Human Medullary Thyroid Carcinoma Cell Line" Biochem Biophys Res Commun, 207(3): 1022-1023.

Evans, E. (May 1, 2016) "The Development of Potent and Selective RET Inhibitors" Slides presented at the 2016 Annual Meeting of the International Thyroid Oncology Group at the University of Colorado (19 pages).

Hayashi, H. et al. (2000) "Characterization of intracellular signals via tyrosine 1062 in RET activated by glial cell line-derived neurotrophic factor" Oncogene, 19:4469-4475.

International Search Report and Written Opinion dated Oct. 12, 2017, in International Patent Application No. PCT/US2017/043964, filed Jul. 26, 2017, by Blueprint Medicines Corp. (13 pages).

International Search Report and Written Opinion dated Oct. 25, 2017, in International Patent Application No. PCT/US2017/043340, filed Jul. 21, 2017, by Blueprint Medicines Corp. (14 pages).

Rahal, R. (Apr. 18, 2016) "The development of potent, selective RET inhibitors" Slides of a Presentation at the American Association for Cancer Research (AACR) Annual Meeting, Apr. 16-20, 2016, New Orleans (15 pages).

Suzuki, M. et al. (Jul. 2013) "Identification of a lung adenocarcinoma cell line with CCDC6-RET fusion gene and the effect of RET inhibitors in vitro and in vivo" Cancer Sci, 104(7):896-903.

Touat, M. et al. (2015) "Targeting FGFR Signaling in Cancer" Clin Cancer Res, 21(12):2684-2694.

Chen, M-H et al. (2014) "Antitumor activity of the combination of a HSP90 inhibitor and a PI3K/mTOR dual inhibitor against cholangiocarcinoma," Oncotarget, 5(8):2372-2389.

Gild, M.L. et al. (Oct. 2013) "Targeting mTOR in RET mutant medullary and differentiated thyroid cancer cells" Endocr Re/at Cancer, 20(5):659-667. HHS Public Access Author Manuscript; available in PMC Mar. 27, 2015 (16 pages).

International Search Report and Written Opinion dated Aug. 21, 2018, in International Patent Application No. PCT/US2018/032794, filed May 15, 2018, by Blueprint Medicines Corp. (18 pages).

Jin, N. et al. (Oct. 15, 2011), "Synergistic Action of a RAF Inhibitor and a Dual PI3K/mTOR Inhibitor in Thyroid Cancer," Clin Cancer Res, 17(20):6482-6489.

Kuster, B. (Ed.) (2012) Kinase Inhibitors. Methods and Protocols. Humana Press; Chapters 1 and 2, pp. 1-44.

Subbiah, V. et al. (Jul. 2015) "Systemic and CNS activity of the RET inhibitor vandetanib combined with the mTOR inhibitor everolimus in KIF5B-RET re-arranged Non-Small Cell Lung Cancer with brain

(56) References Cited

OTHER PUBLICATIONS metastases" Lung Cancer, 89(1):76-79. HHS Public Access Author Manuscript; available in PMC Aug. 25, 2016 (10 pages).
Brandt, W. et al. (2010) "Inhibitors of the RET tyrosine kinase based on a 2-(alkylsulfanyl)-4-(3-thienyl) nicotinonitrile scaffold" Eur J Med Chem, 45:2919-2927.
Mologni, L. et al. (2010) "Synthesis, structure-activity relationship and crystallographic studies of 3-substituted indolin-2-one RET inhibitors" Bioorg Med Chem, 18:1482-1496.
Robinett, R.G. et al. (2007) "The discovery of substituted 4-(3-hyroxyanilino)-quinolines as potent RET kinase inhibitors" Bioorg Med Chem Lett, 17:5886-5893.
Antonescu, C.R. et al. (Jul. 2015) "Molecular Characterization of Inflammatory Myofibroblastic Tumors with Frequent ALK and ROS1 Fusions and Rare Novel RET Gene Rearrangement" Am J Surg Pathol, 39(7):957-967. HHS Public Access Author Manuscript;available in PMC Jul. 1, 2015 (19 pages).
Baselga, J. et al. (2005) "Phase II and Tumor Pharmacodynamic Study of Gefitinib in Patients with Advanced Breast Cancer" J Clin Oncol, 23(23):5323-5333.
Caprelsa (vandetanib) "Full Prescribing Information" Reference ID: 3964956, Cambridge, MA: Sanofi Genzyme; 2016.
Ceccherini, I. et al. (1997) "Somatic in frame deletions not involving juxtamembranous cysteine residues strongly activate the RET proto-oncogene" Oncogene, 14:2609-2612.
Chalice Software Technical Guide, Horizon CombinatoRx Inc., Cambridge, MA, USA (downloaded Jul. 2018).
Cometriq (cabozantinib)"Full Prescribing Information" Reference ID: 3964956, South San Francisco, CA: Exelixix, Inc.; 2018.
Druker, B.J. et al. (2001) "Efficacy and Safety of a Specific Inhibitor of the BCR-ABL Tyrosine Kinase in Chronic Myeloid Leukemia" New Engl J Med, 344(14):1031-1037.
Eisenhauer, E.A. et al. (2009) "New response evaluation criteria in solid tumours: Revised RECIST guideline (version 1.1)" Eur J Cancer, 45:228-247.
Elisei, R. et al. (2008) "Prognostic Significance of Somatic RET Oncogene Mutations in Sporadic Medullary Thyroid Cancer: A 10-Year Follow-Up Study" J Clin Endocrinol Metab, 93(3):682-687.
Fang, P. et al. (Feb. 2016) "Detection of a novel RET gene fusion in a non-small cell lung cancer patient using AMP chemistry" J Thorac Oncol, 11.2:S21-S22.
Gautschi, O. et al. (2016) "Targeting RET in patients with RET-rearranged lung cancers: Results from a global registry" J Clin Oncol, 34(15S) (suppl; abstr 9014).
Grubbs, E.G. et al. (Mar. 2015) "RET Fusion as a Novel Driver of Medullary Thyroid Carcinoma" J Clin Endocrinol Metab, 100:788-793.
Halkova, T. et al. (2015) "A novel RET/PTC variant detected in a pediatric patient with papillary thyroid cancer without ionization history" Hum Pathol, 46:1962-1969.
Horiike, A. et al. (2016) "Sorafenib treatment for patients with RET fusion-positive non-small cell lung cancer" Lung Cancer, 93:43-46.
Joung, J.Y. et al. (2016) "Diffuse sclerosing variant of papillary thyroid carcinoma: major genetic alterations and prognostic implications" Histopathology, 69:45-53.
Jovanovic, R. et al. (2015) "Novel RET Mutations in Macedonian Patients with Medullary Thyroid Carcinoma: Genotype-Phenotype Correlations" Prilozi, 36(1):93-107.
Karrasch, T. et al. (2016) "How to Assess the Clinical Relevance of Novel RET Missense Variants in the Absence of Functional Studies?" Eur Thyroid J, 5:73-77.
Kato, S. et al. (Apr. 15, 2017) "RET Aberrations in Diverse Cancers: Next-Generation Sequencing of 4,871 Patients" Clin Cancer Res, 23(8):1988-1997.
Kim, S.H. et al. (2015) "A New Germline ALA641THR Variant in the Transmembrane Domain of the RET Gene Associated with Medullary Thyroid Cancer" Acta Endocrinologica (Buc), 11.2:189-194.

Krampitz, G.W. and J.A. Norton (2014) "RET Gene Mutations (Genotype and Phenotype) of Multiple Endocrine Neoplasia Type 2 and Familial Medullary Thyroid Carcinoma" Cancer, 120:1920-1931.
Latteyer, S. et al. (Mar. 2016) "A 6-Base Pair in Frame Germline Deletion in Exon 7 of RET Leads to Increased RET Phosphorylation, ERK Activation, and MEN2A" J Clin Endocrinol Metab, 101(3):1016-1022.
Le Rolle, A. et al. (2015) "Identification and characterization of RET fusions in advanced colorectal cancer" Oncotarget, 6(30):28929-28937.
Lee, M.S. et al. (2016) "Efficacy of the combination of MEK and CDK4/6 inhibitors in vitro and in vivo in KRAS mutant colorectal cancer models" Oncotarget, 7(26):39595-39608.
Lehar, J. et al. (2009) "Synergistic drug combinations improve therapeutic selectivity" Nat Biotechnol, 27(7):659-666. HHS Public Access Author Manuscript; available in PMC Jan. 1, 2010 (23 pages).
Lin, J.J. et al. (2016) "Clinical Activity of Alectinib in Advanced RET-Rearranged Non-Small Cell Lung Cancer" J Thorac Oncol, 11(11):2027-2032.
Lipson, D. et al. (2012) "Identification of new ALK and RET gene fusions from colorectal and lung cancer biopsies" Nat Med, 18(3):382-384. HHS Public Access Author Manuscript; available in PMC Feb. 6, 2014 (7 pages).
Machens, A et al. (2003) "Early Malignant Progression of Hereditary Medullary Thyroid Cancer" New Engl J Med, 349:1517-1525.
Moura, M.M. et al. (2009) "Correlation of RET somatic mutations with clinicopathological features in sporadic medullary thyroid carcinomas" Br J Cancer, 100:1777-1783.
Mulligan, L.M. et al. (Jun. 3, 1993) "Germ-line mutations of the RET proto-oncogene in multiple endocrine neoplasia type 2A" Nature, 363:458-460.
Mulligan, L.M. et al. (1995) "Genotype-phenotype correlation in multiple endocrine neoplasia type 2: report of the International RET Mutation Consortium" J Int Med, 238:343-346.
Mulligan, L.M. (Mar. 2014) "RET revisited: expanding the oncogenic portfolio" Nat Rev Cancer, 14:173-186.
Pirker, R. and M. Filipits (2015) "Alectinib in RET-rearranged non-small cell lung cancer—Another progress in precision medicine?" Transl Lung Cancer Res, 4(6):797-800.
Qi, X. et al. (2015) "RET mutation p.S891 A in a Chinese family with familial medullary thyroid carcinoma and associated cutaneous amyloidosis binding OSMR variant p.G513D" Oncotarget, 6(32):33993-34003.
Romei, C. et al. (Apr. 2016) "A comprehensive overview of the role of the RET proto-oncogene in thyroid carcinoma" Nat Rev Endocrinol, 12:192-202.
Saito, M. et al. (Jun. 2016) "Gene aberrations for precision medicine against lung adenocarcinoma" Cancer Sci, 107(6):713-720.
Sarker, D. and P. Workman (2007) "Pharmacodynamic Biomarkers for Molecular Cancer Therapeutics" Adv Cancer Res, 96:213-268.
Scollo, C. et al. (2016) "A novel RET gene mutation in a patient with apparently sporadic pheochromocytoma" Endocr J, 63(1):87-91.
Silva, A.L. et al. (2015) "Identification and characterization of two novel germline RET variants associated with medullary thyroid carcinoma" Endocrine, 49:366-372.
Suehara, Y. et al. (Dec. 15, 2012) "Identification of KIF5B-RET and GOPC-ROS1 fusions in lung adenocarcinomas through a comprehensive mRNA-based screen for tyrosine kinase fusions" Clin Cancer Res, 18(24):6599-6608. HHS Public Access AuthorManuscript; available in PMC Nov. 17, 2014 (18 pages).
Stransky, N. et al. (2014) "The landscape of kinase fusions in cancer" Nat Commun, 5:4846 (10 pages).
Takeuchi, K. et al. (Mar. 2012) "RET, ROS1 and ALK fusions in lung cancer" Nat Med, 18(3):378-381.
Tan, D.S. et al. (2009) "Biomarker-Driven Early Clinical Trials in Oncology" Cancer J, 15(5):406-420.
U.S. Nat'l Library of Med., A Phase 1 Trial of Vandetanib (a Multi-kinase Inhibitor of EGFR, VEGFR and RET Inhibitor) in Combination With Everolimus (an mTOR Inhibitor) in Advanced

(56) References Cited

OTHER PUBLICATIONS

Cancer, ClinicalTrials.gov,https://clinicaltrials.gov/ct2/show/NCT01582191 (last updated Jul. 3, 2018) (7 pages).
U.S. Nat'l Library of Med., Phase 1 Study of the Highly-selective RET Inhibitor BLU-667 in Patients With Thyroid Cancer, Non-Small Cell Lung Cancer, and Other Advanced Solid Tumors, ClinicalTrials.gov, https://clinicaltrials.gov/ct2/show/NCT03037385(last updated Jun. 27, 2018) (8 pages).
Wang, L. et al. (2012) "Identification of a Novel, Recurrent HEY1-NCOA2 Fusion in Mesenchymal Chondrosarcoma based on a Genome-wide Screen of Exon-level Expression Data" Genes Chromosomes Cancer, 51(2):127-139. HHS Public Access Author Manuscript;available in PMC Feb. 1, 2013(24 pages).
Wang, R. et al. (Dec. 10, 2012) "RET Fusions Define a Unique Molecular and Clinicopathologic Subtype of Non-Small-Cell Lung Cancer" J Clin Oncol, 30(35):4352-4359.
Wells, S.A. et al. (2015) "Revised American Thyroid Association Guidelines for the Management of Medullary Thyroid Carcinoma" Thyroid, 25(6):567-610.
Rahal, R. et al. (2016) "The development of potent, selective RET inhibitors that target both wild-type RET and prospectively identified resistance mutations to multi-kinase inhibitors" Abstract submitted to the American Association for CancerResearch (AACR) Annual Meeting, Apr. 16-20, 2016, New Orleans; submission date Dec. 1, 2015 (2 pages).
Ahn M. et al. "OA 09.03 TATTON Ph lb Expansion Cohort: Osimertinib plus Savolitinib for Pts with EGFR-Mutant MET-Amplified NSCLC after Progression on Prior EGFR-TKI." J Thorac Oncol. 12(11) S1768, 2017.
Anonymous "BLU-667 Targets RET-Altered Cancers" Cancer Discovery, vol. 8, No. 6, OF8, Jun. 2018 (Jun. 2018), p. 5pp, XP002792436.
Anonymous, "Phase 1 Study of the Highly-selective RET Inhibitor BLU-667 in Patients With Thyroid Cancer, Non-Small Cell Lung Cancer, and Other Advanced Solid Tumors," ClinicalTrials.org Internet Citation, Apr. 21, 2017 (Apr. 21, 2017), XP002783685.
Engelman J.A. et al. "MET Amplification Leads to Gefitinib Resistance in Lung Cancer by Activating ERBB3 Signaling." Science, 2007, 316 (5827), pp. 1039-1043.
Fagin, J.A. et al. "Biologic and Clinical Perspectives on Thyroid Cancer." N Engl J Med. 2016, 375 (11) pp. 1054-1067.
Gainor J.F. et al. "Dramatic Response to Combination Erlotinib and Crizotinib in a Patient with Advanced, EGFR-Mutant Lung Cancer Harboring De Novo MET Amplification." J Thorac Oncol. 11 (7) 2016, pp. e83-e85.
Vivek Subbiah et al. "Precision Targeted Therapy with BLU-667 for RET-Driven Cancers," Cancer Discovery, vol. 8, No. 7, Apr. 15, 2018 (Apr. 15, 2018), pp. 836-849, XP055599279.
International Search Report and Written Opinion of the International Searching Authority for Intenational Application No. PCT/US2019/025655 dated Jul. 23, 2019 (16 pages).
International Search Report and Written Opinion of the International Searching Authority for International Application No. PCT/US2019/045919 dated Jan. 22, 2020 (11 pages).
Klempner et al. "Emergence of RET rearrangement co-existing with activated EGFR mutation in EGFR-mutated NSCLC patients who had progressed on first- or second-generation EGFR TKI" Lung Cancer, Sep. 2015, vol. 89, No. 3, pp. 357-359; abstract, p. 358, col. 1, para 2, p. 359, col. 1, para 2.
Oxnard, G.R. et al. "Assessment of Resistance Mechanisms and Clinical Implications in Patients With EGFR T790M-Positive Lung Cancer and Acquired Resistance to Osimertinib." JAMA Oncol. 2018, 4(11), pp. 1527-1534.
Ramalingam et al. "Osimertinib As First-Line Treatment of EGFR Mutation-Positive Advanced Non-Small-Cell Lung Cancer" Journal of Clinical Oncology, Mar. 20, 2018, vol. 36, No. 9, p. 841-849; abstract.
Reckamp, K. L. et al. "Abstract 936: Analysis of cell-free DNA from 32,991 advanced cancers reveals novel co-occurring activating RET alterations and oncogenic signaling pathway aberrations." Cancer Research. Pubished Jul. 2018. Proceedings: AACR Annual Meeting 2018; Apr. 14-18, 2018; Chicago, IL. Retrieved from the internet URL: "<https://cancerres.aacrjournals.org/content/78/13_Supplement/936>" (3 pages).
Robinson B. G. et al. "Vandetanib (100 mg) in Patients with Locally Advanced or Metastatic Hereditary Medullary Thyroid Cancer," Journal of Clinical En doc ri no logy and Metabolism, vol. 95, No. 6, Jun. 1, 2010 (Jun. 1, 2010), pp. 2664-2671, XP055599340.
Schrock, A.B. et al. "Receptor Tyrosine Kinase Fusions and BRAF Kinase Fusions are Rare but Actionable Resistance Mechanisms to EGFR Tyrosine Kinase Inhibitors." Translational Oncology, 2018, 13(9) pp. 1312-1323.
Subbiah et al. Abstract CT043 "Highly potent and selective RET inhibitor, BLU-667, achieves proof of concept in a phase I study of advanced, RET-altered solid tumors," Cancer Research vol. 78, No. 13, Supplement 1 Jul. 2018 (Jul. 2018), XP002792435, Proceedings: AACR Annual Meeting 2018; Apr. 14-18, 2018; Chicago, IL. Retrieved from the Internet: URL:http://cancerres.aacrjournals.org/content/78/13Supplement/CT043.
U.S. Appl. No. 15/340,428, U.S. Pat. No. 10,030,005, Inhibitors of RET, filed Nov. 1, 2016, Patented.
U.S. Appl. No. 16/041,719, U.S. Pat. No. 10,584,114, Inhibitors of RET, filed Jul. 20, 2018, Patented.
U.S. Appl. No. 15/548,925, U.S. Pat. No. 10,202,365, 2-(Pyridin-3-yl)-pyrimidine Derivatives as RET Inhibitors, filed Aug. 4, 2017, Patented.
U.S. Appl. No. 16/228,381, U.S. Pat. No. 10,774,070, 2(Pyridin-3-yl)-pyrimidine Derivatives as RET Inhibitors, filed Dec. 20, 2018, Patented.
U.S. Appl. No. 16/990,255, 2-(Pyridin-3-yl)-pyrimidine Derivatives as RET Inhibitors, filed Aug. 11, 2020, Pending.
U.S. Appl. No. 15/462,255, U.S. Pat. No. 10,183,928, Inhibitors of RET, filed Mar. 17, 2017, Patented.
U.S. Appl. No. 15/657,057, U.S. Pat. No. 10,227,329, Compounds Useful for Treating Disorders Related to RET, filed Jul. 21, 2017, Patented.
U.S. Appl. No. 15/660,840, U.S. Pat. No. 10,035,789, Compounds Useful for Treating Disorders Related to RET, filed Jul. 26, 2017, Patented.
U.S. Appl. No. 17/044,884, RET Inhibitor for Use in Treating Cancer Having a RET Alteration, filed Oct. 2, 2020, Pending.
U.S. Appl. No. 17/061,743, RET Inhibitor for Use in Treating Cancer Having a RET Alteration, filed Oct. 2, 2020, Pending.
U.S. Appl. No. 17/127,041, RET Inhibitor for Use in Treating Cancer Having a RET Alteration, filed Dec. 18, 2020, Pending.

INHIBITORS OF RET

CLAIM OF PRIORITY

This application is a continuation of U.S. application Ser. No. 16/041,719, filed Jul. 20, 2018, which application is a continuation of U.S. application Ser. No. 15/340,428, filed Nov. 1, 2016, which claims priority from U.S. Provisional Application No. 62/249,784, filed Nov. 2, 2015, and U.S. Provisional Application No. 62/367,960, filed Jul. 28, 2016, each of which is incorporated herein by reference in its entirety.

This invention relates to inhibitors of RET that are active against wild-type RET and its resistant mutants.

BACKGROUND

RET (rearranged during transfection) is a receptor tyrosine kinase that activates multiple downstream pathways involved in cell proliferation and survival. RET fusions are implicated in several cancers including papillary thyroid carcinoma and non-small cell lung cancer. A genomics analysis on the landscape of kinase fusions identified RET fusions in breast and colon cancer patient samples, providing therapeutic rationale for the use of RET inhibitors in multiple patient subpopulations.

The identification of RET fusions as drivers in some cancers prompted the use of approved multi-kinase inhibitors with RET inhibitory activity to treat patients whose tumors express a RET fusion protein. However, these drugs cannot always be dosed at the levels required to sufficiently inhibit RET due to toxicities that result from inhibition of targets other than RET. Further, one of the greatest challenges in treating cancer is the ability of tumor cells to become resistant to therapy. Kinase reactivation via mutation is a common mechanism of resistance. When resistance occurs, the patient's treatment options are often very limited, and the cancer progresses, unchecked, in most instances. There is thus a need for compounds that inhibit RET, as well as its resistant mutants.

SUMMARY

The present invention provides inhibitors of RET and RET mutants, e.g., RET resistant mutants (as defined herein), for example, inhibitors of structural formula (I) and pharmaceutically acceptable salts and compositions thereof. The present invention further provides methods of using the compounds of the invention, and pharmaceutically acceptable salts and compositions thereof, to inhibit the activity of RET or RET mutants in a cell or patient. The present invention still further provides methods for using the compounds of the invention, and pharmaceutically acceptable salts and compositions thereof, to treat a subject suffering from a condition mediated by aberrant RET activity, e.g., cancer.

In one aspect, the invention features a compound of structural formula (A) or a pharmaceutically acceptable salt thereof:

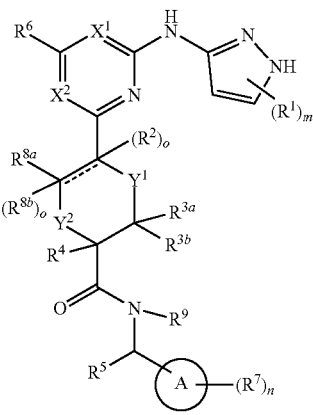

(A)

wherein each of ring A, $X^1$, $X^2$, $Y^1$, $Y^2$, $R^1$, $R^2$, $R^{3a}$, $R^{3b}$, $R^4$, $R^5$, $R^6$, $R^7$, $R^{8a}$, $R^{8b}$, $R^9$, m, n, o and " === " is described herein.

In another aspect, the present invention provides pharmaceutical compositions comprising a compound of structural formula (I) or a pharmaceutically acceptable salt thereof and a pharmaceutically acceptable carrier.

In another aspect, the present invention provides a method for inhibiting RET activity in a cell or in a patient. In some embodiments, said method comprises the step of contacting the cell or administering to the patient a compound of structural formula (I) or a pharmaceutically acceptable salt or composition thereof.

In another aspect, the present invention provides a method for treating a subject suffering from a condition mediated by aberrant RET activity. In some embodiments, said method comprises administering to the subject a therapeutically effective amount of a compound of structural formula (I) or a pharmaceutically acceptable salt or composition thereof.

In another aspect, the present invention provides a method for treating a subject who has developed resistance to a cancer treatment. In some embodiments, said method comprises administering to the subject a therapeutically effective amount of a compound of structural formula (I) or a pharmaceutically acceptable salt or composition thereof.

EMBODIMENTS OF THE INVENTION

Compounds

In one aspect, the present invention features a compound having the structural formula (A):

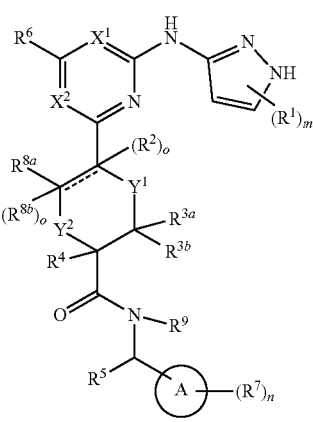

(A)

or a pharmaceutically acceptable salt thereof, wherein:
ring A is an aryl or heteroaryl ring;
each of $X^1$ and $X^2$ is independently selected from N and $C(R^6)$;
each of $Y^1$ and $Y^2$ is independently selected from —$CH_2$— and —O—, wherein no more than one of $Y^1$ or $Y^2$ is —O—;
each $R^1$ and each $R^7$ is independently selected from selected from $C_1$-$C_6$ alkyl, $C_2$-$C_6$ alkenyl, $C_2$-$C_6$ alkynyl, $C_1$-$C_6$ alkoxy, halo, $C_1$-$C_6$ heteroalkyl, cycloalkyl, aryl, heteroaryl, aryloxy, aralkyl, heterocyclyl, heterocyclylalkyl, nitro, cyano, —C(O)R, —OC(O)R, —C(O)OR, —($C_1$-$C_6$ alkylene)-C(O)R, —SR, —S(O)$_2$R, —S(O)$_2$—N(R)(R). —($C_1$-$C_6$ alkylene)-S(O)$_2$R, —($C_1$-$C_6$ alkylene)-S(O)$_2$—N(R)(R), —N(R)(R), —C(O)—N(R)(R), —N(R)—C(O)R, —N(R)—C(Q)OR, —($C_1$-$C_6$ alkylene)-N(R)—C(O)R, —N(R)S(O)$_2$R, and —P(O)(R)(R); wherein each of alkyl, alkenyl, alkynyl, alkoxy, heteroalkyl, cycloalkyl, aryl, heteroaryl, aryloxy, aralkyl, heterocyclyl, and heterocyclylalkyl is independently substituted with 0-5 occurrences of $R^a$; or two $R^1$ or two $R^7$ are taken together with the carbon atoms to which they are attached form a cycloalkyl or heterocyclyl ring independently substituted with 0-5 occurrences of $R^b$;
each of $R^2$ when present, $R^{3a}$, $R^{3b}$, $R^4$, $R^{8a}$ and $R^{8b}$, when present is independently selected from hydrogen, $C_1$-$C_6$ alkyl, $C_1$-$C_6$ alkoxy, halo, hydroxyl, $C_1$-$C_6$ heteroalkyl, and —N(R)(R); wherein each alkyl, alkoxy, and heteroalkyl is optionally and independently substituted with 0-5 occurrences of $R^a$;
each of $R^5$ and $R^9$ is independently selected from hydrogen, $C_1$-$C_6$ alkyl, and $C_1$-$C_6$ heteroalkyl; wherein each alkyl and heteroalkyl is optionally and independently substituted with 0-5 occurrences of $R^a$;
each $R^6$ is independently selected from hydrogen, $C_1$-$C_6$ alkyl, $C_1$-$C_6$ alkoxy, halo, $C_1$-$C_6$ heteroalkyl, and —N(R)(R); wherein each alkyl, alkoxy, and heteroalkyl is optionally and independently substituted with 0-5 occurrences of $R^a$;
each R is independently selected from hydrogen, hydroxyl, halo, thiol, $C_1$-$C_6$ alkyl, $C_1$-$C_6$ thioalkyl, $C_1$-$C_6$ alkoxy, $C_1$-$C_6$ heteroalkyl, cycloalkyl, cycloalkylalkyl, heteroarylalkyl, heterocyclyl, and heterocyclylalkyl, wherein each of alkyl, thioalkyl, alkoxy, heteroalkyl, cycloalkyl, cycloalkylalkyl, heteroarylalkyl, heterocyclyl, and heterocyclylalkyl is independently substituted with 0-5 occurrences of $R^a$, or 2 $R^1$ together with the atom(s) to which they are attached form a cycloalkyl or heterocyclyl ring independently substituted with 0-5 occurrences of $R^b$;
each $R^a$ and each $R^b$ is independently selected from $C_1$-$C_6$ alkyl, halo, hydroxyl, $C_1$-$C_6$ heteroalkyl, $C_1$-$C_6$ alkoxy, cycloalkyl, heterocyclyl, or cyano, wherein each of alkyl, heteroalkyl, alkoxy, cycloalkyl and heterocyclyl is independently substituted with 0-5 occurrences of R';
each R' is independently selected from $C_1$-$C_6$ alkyl, $C_1$-$C_6$ heteroalkyl, halo, hydroxyl, cycloalkyl or cyano; or 2 R' together with the atom(s) to which they are attached form a cycloalkyl or heterocyclyl ring;

m is 0, 1, or 2;
n is 0, 1, 2, or 3;
═══ represents a single or double bond;
each o is 0 when ═══ is a double bond; and
each o is 1 when ═══ is a single bond.

In some embodiments, the compound is a compound having formula (I):

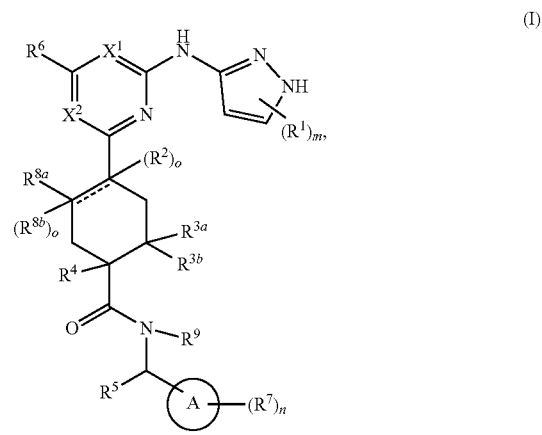

(I)

or a pharmaceutically acceptable salt thereof, wherein each of ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, R, $R^a$, $R^b$, R', m, and n is as described for a compound of Formula A.

In some embodiments, ═══ represents a single bond and the compound has formula Ia:

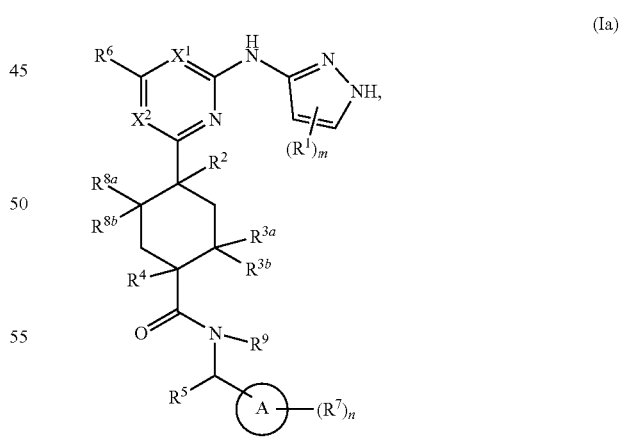

(Ia)

or a pharmaceutically acceptable salt thereof, wherein each of ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, R, $R^a$, $R^b$, R', m, and n is as described for a compound of Formula A.

In some embodiments, ═══ represents a double bond and the compound has formula Ib:

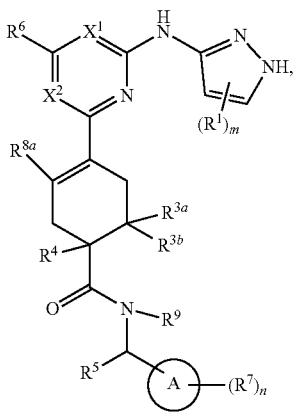

(Ib)

or a pharmaceutically acceptable salt thereof, wherein each of ring A, $X^1$, $X^2$, $R^1$, $R^3R^{3b}$, $R^4$, $R^5$, $R^6$, $R^7$, $R^{8a}$, $R^9$, R, $R^a$, $R^b$, R', m, and n is as described for a compound of Formula A.

In some embodiments of any of Formulae A, I, Ia or Ib, $R^1$ is located at the 5-position. In some embodiments, $R^1$ is located at the 4-position. In some embodiments, $R^1$ is $C_1$-$C_4$ alkyl optionally substituted with 0-3 occurrences of $R^a$. In some embodiments, m is 1 or 2. In some embodiments, m is 1. In some embodiments, m is 1; $R^1$ is located at the 5-position; and $R^1$ is $C_1$-$C_4$ alkyl optionally substituted with 0-3 occurrences of $R^a$. In some embodiments, $R^1$ is —$CH_3$.

In some embodiments of Formulae I or Ia, $R^2$ is selected from hydrogen, hydroxyl, halo and O—$C_1$-$C_4$ alkyl. In some embodiments, $R^2$ is selected from hydrogen, hydroxyl, fluoro and —$OCH_3$.

In some embodiments any of Formulae A, I, Ia or Ib, each of $R^{3a}$, $R^{3b}$, $R^{8a}$ and $R^{8b}$ (which is only present in Formulae I or Ia) is independently selected from hydrogen and $C_1$-$C_4$ alkyl optionally substituted with 0-3 occurrences of $R^a$. In some embodiments, each of $R^{3a}$, $R^{3b}$, $R^{8a}$ and $R^{8b}$ is independently selected from hydrogen and —$CH_3$. In some embodiments, at least one pair of $R^{3a}$ and $R^{3b}$ or $R^{8a}$ and $R^{8b}$ is simultaneously hydrogen.

In some embodiments any of Formulae A, I, Ia or Ib, $R^4$ is selected from hydrogen, $C_1$-$C_4$ alkyl, and O—$C_1$-$C_4$ alkyl, wherein each alkyl portion of $R^4$ is optionally substituted with 0-3 occurrences of $R^a$. In some embodiments, $R^4$ is selected from hydrogen, —$CH_3$, —$CH_2CH_3$, —$OCH_3$ and —$OCH_2CH_3$.

In some embodiments any of Formulae A, I, Ia or Ib, $R^5$ is selected from hydrogen and $C_1$-$C_4$ alkyl optionally substituted with 0-3 occurrences of $R^a$. In some embodiments, $R^5$ is selected from hydrogen and —$CH_3$.

In some embodiments any of Formulae A, I, Ia or Ib, each $R^6$ is independently selected from hydrogen, halo, and $C_1$-$C_4$ alkyl optionally substituted with 0-3 occurrences of $R^a$. In some embodiments, each $R^6$ is independently selected from hydrogen, chloro, and —$CH_3$. In some embodiments, no more than one $R^6$ is other than hydrogen.

In some embodiments any of Formulae A, I, Ia or Ib, ring A is a 6-membered monocyclic heteroaryl comprising at least one nitrogen ring atom. In some embodiments, ring A is selected from

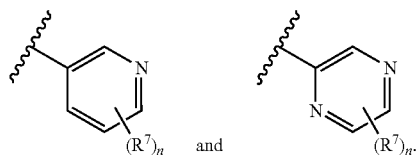

and

In some embodiments any of Formulae A, I, Ia or Ib, $R^7$ is heteroaryl optionally substituted with 0-3 occurrences of $R^b$. In some embodiments, $R^7$ is selected from 4-fluoropyrazole-1-yl, 4-chloropyrazol-1-yl, pyrazol-1-yl, and 3,5-dimethylpyrazol-1-yl optionally substituted with 0-3 occurrences of $R^b$. In some embodiments, $R^7$ is pyrazol-1-yl optionally substituted with 0-3 occurrences of $R^b$. In some embodiments, n is 1. In some embodiments, n is 1; and $R^7$ is pyrazol-1-yl an optionally substituted with 0-3 occurrences of $R^b$.

In some embodiments any of Formulae A, I, Ia or Ib, $R^9$ is selected from hydrogen and $C_1$-$C_4$ alkyl optionally substituted with 0-3 occurrences of $R^a$. In some embodiments, $R^9$ is hydrogen. In some embodiments, $R^9$ is $C_1$-$C_4$ alkyl. In some embodiments, $R^5$ and $R^9$ are both hydrogen.

In some embodiments, the compound is a compound having the structural formula (Ic):

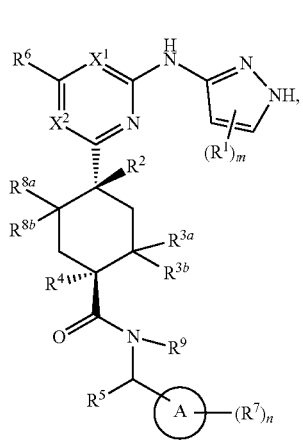

(Ic)

or a pharmaceutically acceptable salt thereof, wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, m and n are as defined for Formula (A).

In some embodiments, the compound is a compound having the structural formula (Id):

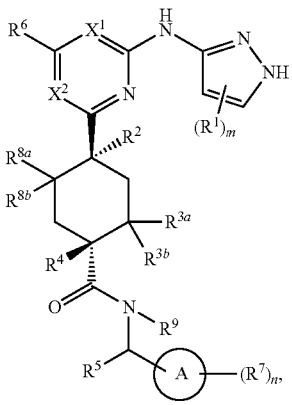

(Id)

or a pharmaceutically acceptable salt thereof,
wherein ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, m and n are as defined for Formula (A).

In some embodiments, the compound is a compound having the structural formula Ie:

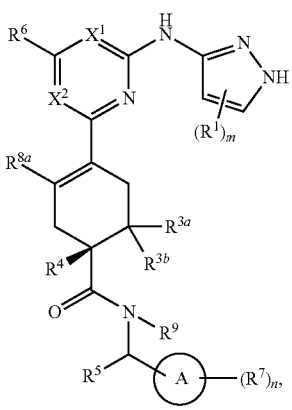

(Ie)

or a pharmaceutically acceptable salt thereof,
wherein ring A, $X^1$, $X^2$, $R^1$, $R^{3a}$, $R^{3b}$, $R^4$, $R^5$, $R^6$, $R^7$, $R^{8a}$, $R^9$, m and n are as defined for Formula (A).

In some embodiments, the compound is a compound having the structural formula (If):

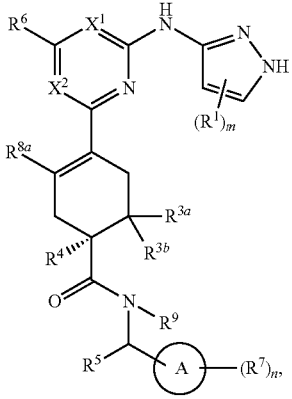

(If)

or a pharmaceutically acceptable salt thereof,
wherein ring A, $X^1$, $X^2$, $R^1$, $R^{3a}$, $R^{3b}$, $R^4$, $R^5$, $R^6$, $R^7$, $R^{8a}$, $R^9$, m and n are as defined for Formula (A).

In another aspect, the present invention features a compound having the structural formula (II):

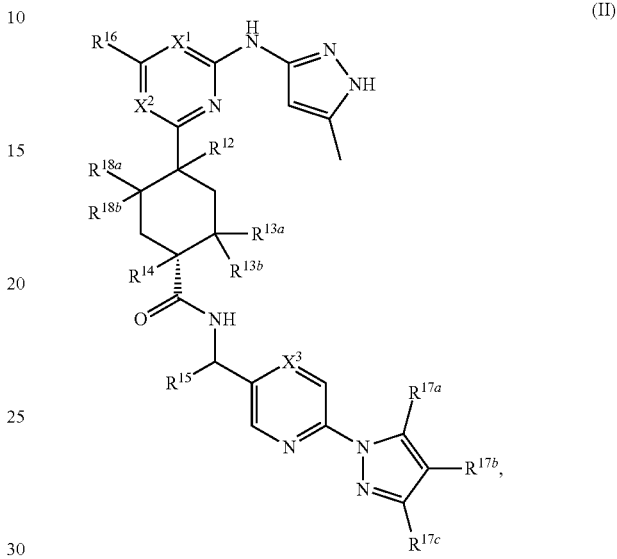

(II)

or a pharmaceutically acceptable salt thereof, wherein:

$X^1$ is selected from N, CH and C (halo);

$X^2$ is selected from N and CH;

$X^3$ is selected from N and CH;

$R^{12}$ is selected from hydrogen, hydroxyl, halo and O—$C_1$-$C_4$ alkyl;

each of $R^{13a}$, $R^{13b}$, $R^{18a}$ and $R^{18b}$ is independently selected from hydrogen and $C_1$-$C_4$ alkyl;

$R^{14}$ is selected from hydrogen, —$C_1$-$C_4$ alkyl and —O—$C_1$-$C_4$ alkyl;

$R^{15}$ is selected from hydrogen and —$C_1$-$C_4$ alkyl;

$R^{16}$ is selected from hydrogen and —$C_1$-$C_4$ alkyl;

$R^{17b}$ is selected from hydrogen and halo; and $R^{17a}$ and $R^{17c}$ are independently selected from hydrogen and —$C_1$-$C_4$ alkyl.

In some embodiments, $X^1$ is selected from N, CH and C(Cl); $X^2$ is selected from N and CH; $X^3$ is selected from N and CH; $R^{12}$ is selected from hydrogen, hydroxyl, fluoro and —O—$CH_3$; each of $R^{13a}$, $R^{13b}$, $R^{8a}$ and $R^{8b}$ is independently selected from hydrogen, methyl and ethyl; and wherein at least one pair of $R^{13a}$ and $R^{13b}$ or $R^{18a}$ and $R^{18b}$ is simultaneously hydrogen; $R^{14}$ is selected from hydrogen, —$CH_3$, —$CH_2CH_3$, —$OCH_3$ and —$OCH_2CH_3$; $R^{15}$ is selected from hydrogen and —$CH_3$; $R^{16}$ is selected from hydrogen and —$CH_3$; $R^{17b}$ is selected from hydrogen, chloro and fluoro; $R^{17a}$ and $R^{17c}$ are simultaneously hydrogen or —$CH_3$, wherein when $R^{17a}$ and $R^{17c}$ are simultaneously —$CH_3$, $R^{17b}$ is hydrogen.

In some embodiments, the compound is a compound having the structural formula (IIa):

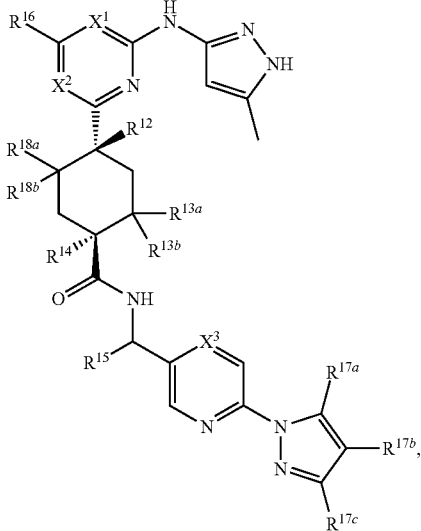

(IIa)

or a pharmaceutically acceptable salt thereof,
wherein $X^1$, $X^2$, $X^3$, $R^{12}$, $R^{13a}$, $R^{13b}$, $R^{14}$, $R^{15}$, $R^{16}$, $R^{17a}$, $R^{17b}$, $R^{17c}$, $R^{18a}$, and $R^{8b}$ are as defined as for Formula (II).

In some embodiments, the compound is a compound having the structural formula (IIb):

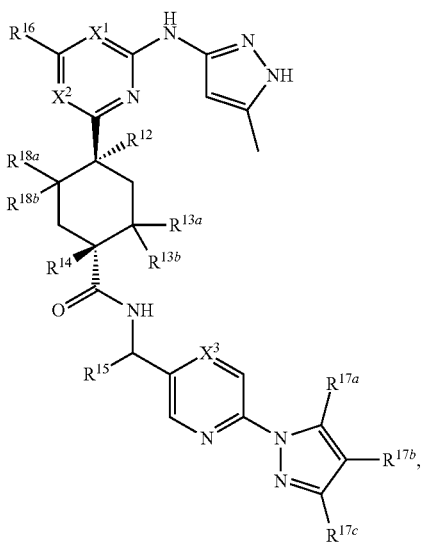

(IIb)

or a pharmaceutically acceptable salt thereof,
wherein $X^1$, $X^2$, $X^3$, $R^{12}$, $R^{13a}$, $R^{13b}$, $R^{14}$, $R^{15}$, $R^{16}$, $R^{17a}$, $R^{17b}$, $R^{17c}$, $R^{18a}$, and $R^{8b}$ are as defined as for Formula (II).

In some embodiments, the invention provides a compound of Formula IIIa or Formula IIIb:

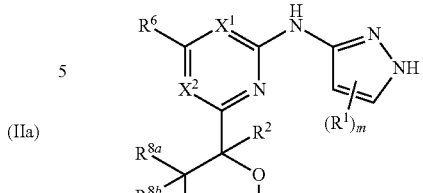

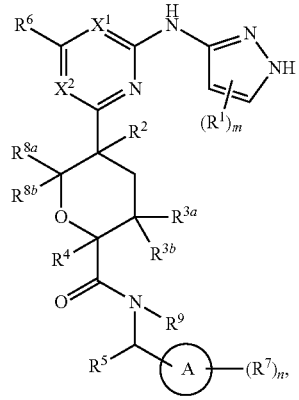

(IIIa)

(IIIb)

or a pharmaceutically acceptable salt thereof, wherein each of ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, R, $R^a$, $R^b$, R', m, and n is as described for a compound of Formula A, including the more specific embodiments and aspects of each of the above variables.

In some embodiments of Formula IIIb, the compound has the Formula IIIb-1:

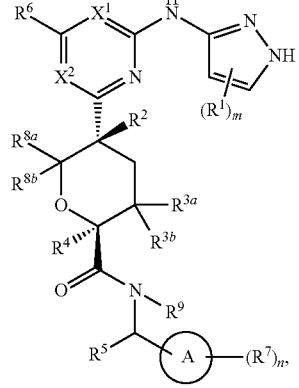

(IIIb-1)

or a pharmaceutically acceptable salt thereof, wherein each of ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, R, $R^a$, $R^b$, R', m, and n is as described for a compound of Formula A, including the more specific embodiments and aspects of each of the above variables.

In some embodiments of Formula IIIb, the compound has the Formula IIIb-2:

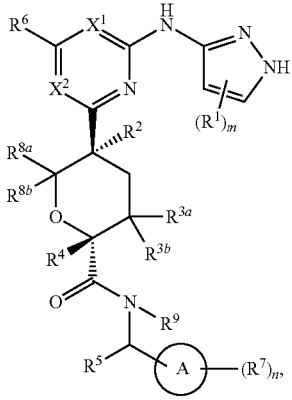

(IIIb-2)

or a pharmaceutically acceptable salt thereof, wherein each of ring A, $X^1$, $X^2$, $R^1$, $R^2$, $R^{3a}$, $R^{3b}$, $R^4$, $R^5$, $R^6$, $R^7$, $R^{8a}$, $R^{8b}$, $R^9$, R, $R^a$, $R^b$, R', m, and n is as described for a compound of Formula A, including the more specific embodiments and aspects of each of the above variables.

In some embodiments of Formulae IIIa, IIIb, IIIb-1 and IIIb-2, each of $X^1$ and $X^2$ is $C(R^6)$. In one aspect of these embodiments, each of $X^1$ and $X^2$ is CH.

In some embodiments of Formula IIIb, the compound has the Formula IIIb-3 or IIIb-4:

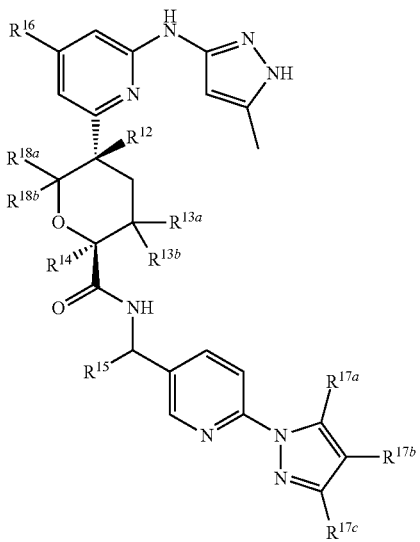

(IIIb-3)

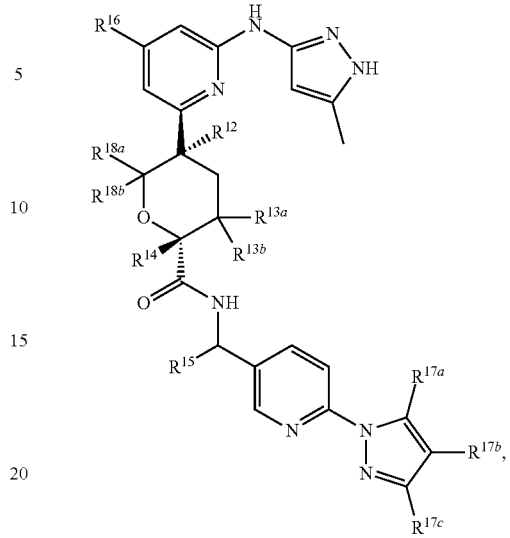

(IIIb-4)

or a pharmaceutically acceptable salt thereof, wherein each of $R^{12}$, $R^{13a}$, $R^{13b}$, $R^{14}$, $R^{15}$, $R^{16}$, $R^{17a}$, $R^{17b}$, $R^{17c}$, $R^{18a}$ and $R^{18b}$ are as defined for Formula II, including the more specific embodiments and aspects of each of the above variables.

In some embodiments, the present invention features a compound selected from any compound in Table 1.

In another aspect, the present invention features a pharmaceutical composition comprising a compound of Formula A, I, Ia, Ib, Ic, Id, II, IIa, IIb, IIIa, IIIb, IIIb-1, IIIb-2, IIIb-3, or IIIb-4 described herein (e.g., a compound in Table 1) or a pharmaceutically acceptable salt thereof, and a pharmaceutically acceptable carrier.

In another aspect, the present invention features a method for inhibiting RET activity in a cell or in a patient comprising the step of contacting the cell or administering to the patient a compound described herein (e.g., a compound in Table 1) or a pharmaceutically acceptable salt thereof, or a pharmaceutical composition thereof.

In another aspect, the present invention features a method for treating a subject suffering from a condition mediated by aberrant RET activity, comprising administering to the subject a therapeutically effective amount of a compound described herein (e.g., a compound in Table 1) or a pharmaceutically acceptable salt thereof, or a pharmaceutical composition thereof.

In another aspect, the present invention features a method for treating a subject who has developed resistance to a cancer treatment, comprising administering to the subject a therapeutically effective amount of a compound described herein (e.g., a compound in Table 1) or a pharmaceutically acceptable salt thereof, or a pharmaceutical composition thereof.

Definitions

As used herein, the terms a "patient," "subject," "individual," and "host" refer to either a human or a non-human animal suffering from or suspected of suffering from a disease or disorder associated with aberrant RET expression (i.e., increased RET activity caused by signaling through RET) or biological activity.

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by over expression of RET or aberrant RET biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

As used herein, "developing resistance" means that when a drug is first administered to the patient, the patient's symptoms improve, whether measured by decrease in tumor volume, a decrease in the number of new lesions, or some other means that a physician uses to judge disease progression; however, those symptoms stop improving, or even worsen at some point. At that time, the patient is said to have developed resistance to the drug.

"Aliphatic group" means a straight-chain, branched-chain, or cyclic hydrocarbon group and includes saturated and unsaturated groups, such as an alkyl group, an alkenyl group, and an alkynyl group.

"Alkylene" refers to a divalent radical of an alkyl group, e.g., —CH$_2$—, —CH$_2$CH$_2$—, and —CH$_2$CH$_2$CH$_2$—.

"Alkenyl" means an aliphatic group containing at least one double bond.

"Alkoxyl" or "alkoxy" means an alkyl group having an oxygen radical attached thereto. Representative alkoxyl groups include methoxy, ethoxy, propyloxy, tert-butoxy and the like. The term "haloalkoxy" refers to an alkoxy in which one or more hydrogen atoms are replaced by halo, and includes alkoxy moieties in which all hydrogens have been replaced by halo (e.g., perfluoroalkoxy).

"Alkyl" refers to a monovalent radical of a saturated straight or branched hydrocarbon, such as a straight or branched group of 1-12, 1-10, or 1-6 carbon atoms, referred to herein as C$_1$-C$_{12}$ alkyl, C$_1$-C$_{10}$ alkyl, and C$_1$-C$_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

"Alkenylene" refers to an alkenyl group having two connecting points. For example, "ethenylene" represents the group —CH=CH—. Alkenylene groups can also be in an unsubstituted form or substituted form with one or more substituents.

"Alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkynylene" refers to an alkynyl having two connecting points. For example, "ethynylene" represents the group —C≡C—. Alkynylene groups can also be in an unsubstituted form or substituted form with one or more substituents.

"Aromatic ring system" is art-recognized and refers to a monocyclic, bicyclic or polycyclic hydrocarbon ring system, wherein at least one ring is aromatic.

"Aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

"Arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

"Aryloxy" refers to —O-(aryl), wherein the heteroaryl moiety is as defined herein.

"Halo" refers to a radical of any halogen, e.g., —F, —Cl, —Br, or —I.

"Heteroalkyl" refers to an optionally substituted alkyl, which has one or more skeletal chain atoms selected from an atom other than carbon, e.g., oxygen, nitrogen, sulfur, phosphorus or combinations thereof. A numerical range may be given, e.g. C$_1$-C$_6$ heteroalkyl which refers to the number of carbons in the chain, which in this example includes 1 to 6 carbon atoms. For example, a —CH$_2$OCH$_2$CH$_3$ radical is referred to as a "C$_3$" heteroalkyl. Connection to the rest of the molecule may be through either a heteroatom or a carbon in the heteroalkyl chain. "Heteroalkylene" refers to a divalent optionally substituted alkyl, which has one or more skeletal chain atoms selected from an atom other than carbon, e.g., oxygen, nitrogen, sulfur, phosphorus or combinations thereof.

"Carbocyclic ring system" refers to a monocyclic, bicyclic or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

"Cycloalkyl" refers to a cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

"Cycloalkylalkyl" refers to a -(cycloalkyl)-alkyl radical where cycloalkyl and alkyl are as disclosed herein. The "cycloalkylalkyl" is bonded to the parent molecular structure through the cycloalkyl group.

"Heteroaromatic ring system" is art-recognized and refers to monocyclic, bicyclic or polycyclic ring system wherein at least one ring is both aromatic and comprises at least one heteroatom (e.g., N, O or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl, pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to monocyclic, bicyclic and polycyclic ring systems where at least one ring is saturated or partially unsaturated (but not aromatic) and that ring comprises at least one heteroatom. A heterocyclic ring system can be attached to its pendant group at any heteroatom or carbon atom that results in a stable structure and any of the ring atoms can be optionally substituted.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Heterocyclylalkyl" refers to an alkyl group substituted with a heterocyclyl group.

"Cyano" refers to a —CN radical.

"Nitro" refers to —NO$_2$.

"Hydroxy" or "hydroxyl" refers to —OH.

As used herein, the definition of each expression, e.g., alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example deuterium ($^2$H), tritium ($^3$H), carbon-13 ($^{13}$C), or carbon-14 ($^{14}$C). All isotopic variations of the compounds disclosed herein, whether radioactive or not, are intended to be encompassed within the scope of the present invention. In addition, all tautomeric forms of the compounds described herein are intended to be within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, heteroalkyl, heteroalkylene, carbocyclyl, heterocyclyl, aryl group and heteroaryl group include halogen, =O, —CN, —OR$^c$, —NR$^d$R$^e$, —S(O)$_k$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, $C_1$-$C_6$ alkyl, $C_1$-$C_6$ haloalkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, wherein each of said alkyl, alkylene, heteroalkyl, heteroalkylene, carbocyclyl, heterocyclyl, aryl and heteroaryl are optionally substituted with one or more of halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, $C_1$-$C_6$ alkyl, $C_1$-$C_6$ haloalkyl, or $C_1$-$C_6$ heteroalkyl, and wherein R$^c$ is hydrogen, hydroxy, $C_1$-$C_6$ alkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, each of which is optionally substituted with one or more of halogen, hydroxy, $C_1$-$C_6$ alkyl, $C_1$-$C_6$ haloalkyl, $C_1$-$C_6$ heteroalkyl, carbocyclyl, heterocyclyl, aryl, or heteroaryl; R$^d$ and R$^e$ are each independently selected from hydrogen, $C_1$-$C_6$ alkyl, or $C_1$-$C_6$ heteroalkyl; and k is 0, 1 or 2. The invention is not intended to be limited in any manner by the above exemplary listing of substituents.

TABLE 1

Exemplary Compounds of the Invention.

| Compound | Structure |
| --- | --- |
| 100 | 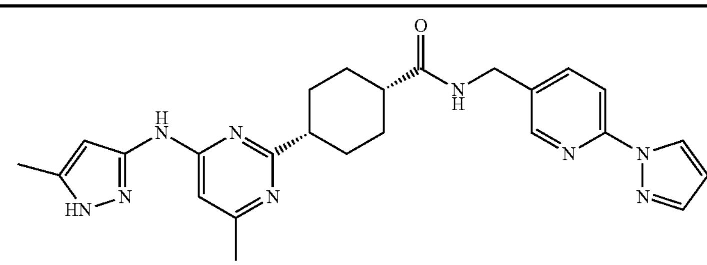 |
| 101 | 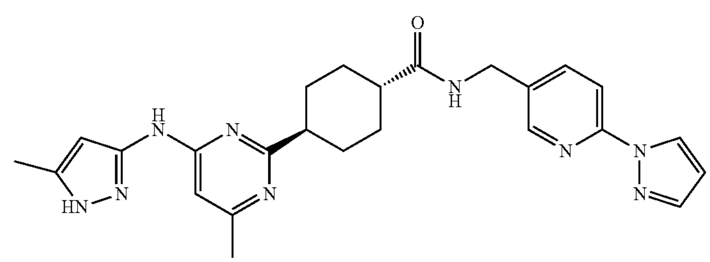 [SMILES: Cc1cc(Nc2cc(C)[nH]n2)nc([C@H]2CC[C@H](C(=O)NCc3ccc(-n4cccn4)nc3)CC2)n1] |
| 102 | 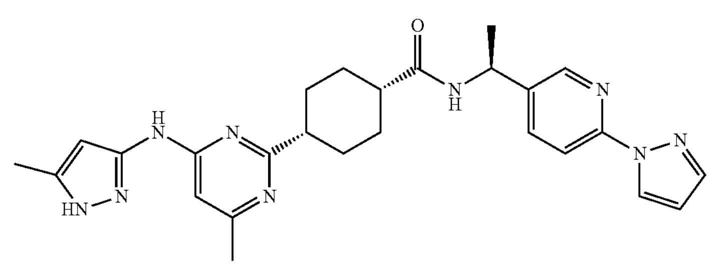 [SMILES: Cc1cc(Nc2cc(C)[nH]n2)nc([C@H]2CC[C@@H](C(=O)N[C@@H](C)c3ccc(-n4cccn4)nc3)CC2)n1] |
| 103 | 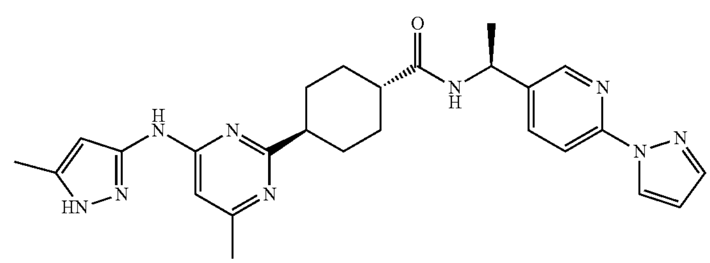 [SMILES: Cc1cc(Nc2cc(C)[nH]n2)nc([C@H]2CC[C@H](C(=O)N[C@@H](C)c3ccc(-n4cccn4)nc3)CC2)n1] |

TABLE 1-continued

Exemplary Compounds of the Invention.

| Compound | Structure |
|---|---|
| 104 | 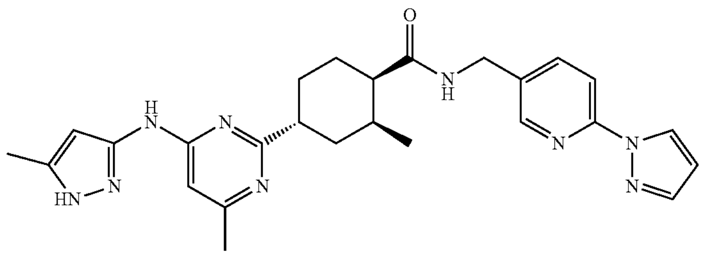 [SMILES: Cc1cc(Nc2cc(C)[nH]n2)nc([C@@H]2CC[C@@H](C(=O)NCc3ccc(-n4cccn4)nc3)[C@@H](C)C2)n1] |
| 105 | 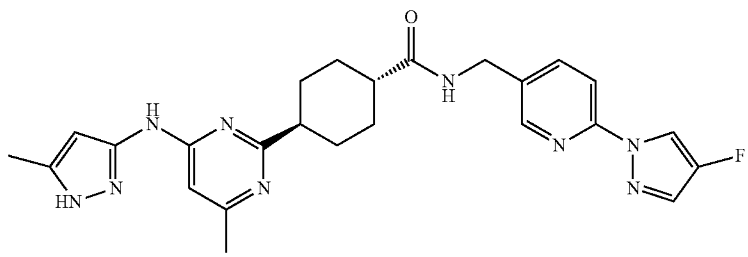 [SMILES: Cc1cc(Nc2cc(C)[nH]n2)nc([C@H]2CC[C@H](C(=O)NCc3ccc(-n4cc(F)cn4)nc3)CC2)n1] |
| 106 | 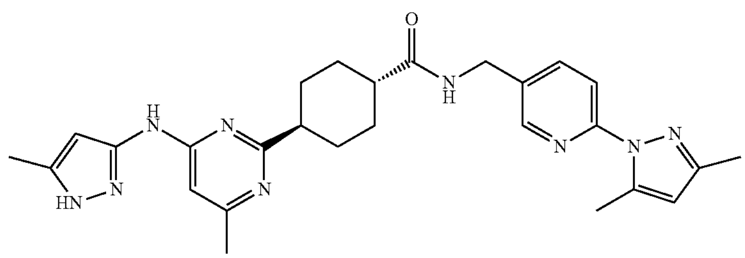 |
| 107 | 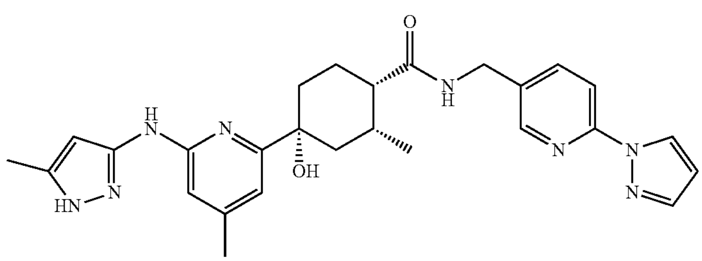 [SMILES: Cc1cc(Nc2cc(C)[nH]n2)nc([C@@]2(O)CC[C@H](C(=O)NCc3ccc(-n4cccn4)nc3)[C@H](C)C2)c1] |
| 108 | 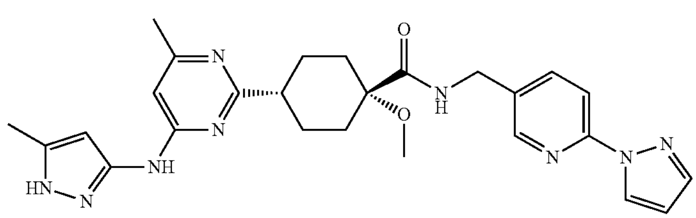 [SMILES: CO[C@]1(C(=O)NCc2ccc(-n3cccn3)nc2)CC[C@H](c2nc(C)cc(Nc3cc(C)[nH]n3)n2)CC1] |
| 109 | 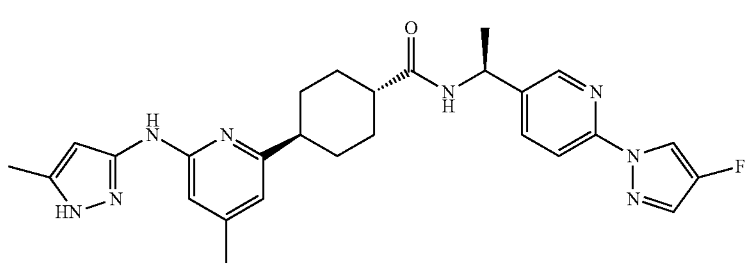 [SMILES: Cc1cc(Nc2cc(C)[nH]n2)nc([C@H]2CC[C@H](C(=O)N[C@@H](C)c3ccc(-n4cc(F)cn4)nc3)CC2)c1] |

TABLE 1-continued

Exemplary Compounds of the Invention.

| Compound | Structure |
| --- | --- |
| 110 | 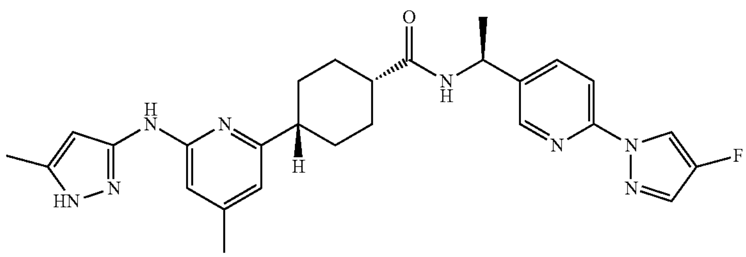 [SMILES: Cc1cc(Nc2cc(C)[nH]n2)nc([C@H]2CC[C@@H](C(=O)N[C@@H](C)c3ccc(-n4cc(F)cn4)nc3)CC2)c1] |
| 111 | 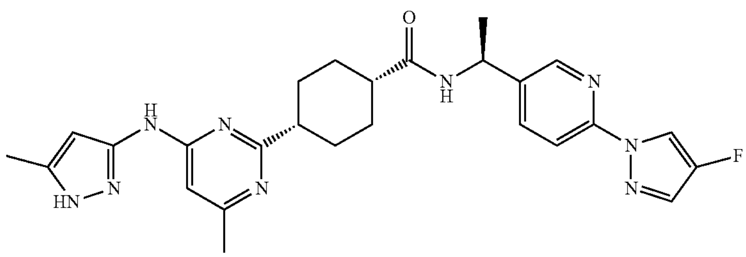 [SMILES: Cc1cc(Nc2cc(C)[nH]n2)nc([C@H]2CC[C@@H](C(=O)N[C@@H](C)c3ccc(-n4cc(F)cn4)nc3)CC2)n1] |
| 112 | 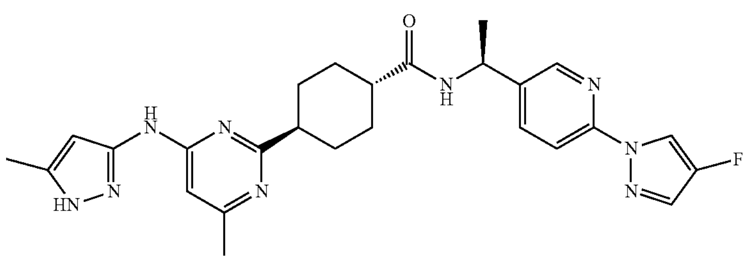 [SMILES: Cc1cc(Nc2cc(C)[nH]n2)nc([C@H]2CC[C@H](C(=O)N[C@@H](C)c3ccc(-n4cc(F)cn4)nc3)CC2)n1] |
| 113 | 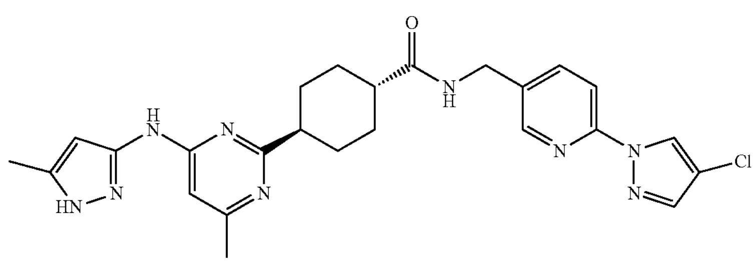 [SMILES: Cc1cc(Nc2cc(C)[nH]n2)nc([C@H]2CC[C@H](C(=O)NCc3ccc(-n4cc(Cl)cn4)nc3)CC2)n1] |
| 114 | 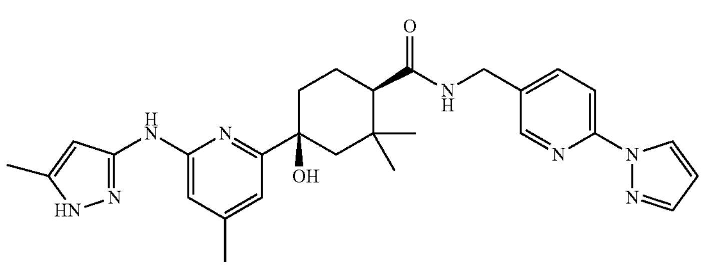 [SMILES: Cc1cc(Nc2cc(C)[nH]n2)nc([C@]2(O)CC[C@@H](C(=O)NCc3ccc(-n4cccn4)nc3)C(C)(C)C2)c1] |
| 115 | 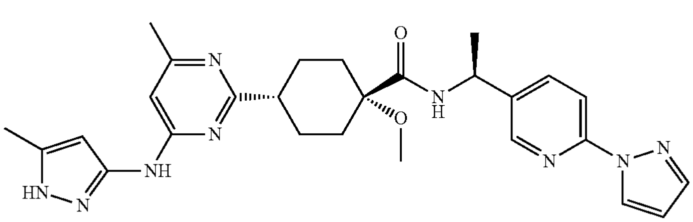 [SMILES: CO[C@]1(C(=O)N[C@@H](C)c2ccc(-n3cccn3)nc2)CC[C@H](c2nc(C)cc(Nc3cc(C)[nH]n3)n2)CC1] |

TABLE 1-continued

Exemplary Compounds of the Invention.

| Compound | Structure |
|---|---|
| 116 | 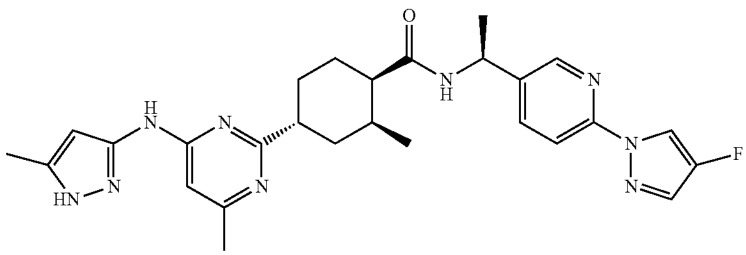 [SMILES: Cc1cc(Nc2cc(C)[nH]n2)nc([C@@H]2CC[C@@H](C(=O)N[C@@H](C)c3ccc(-n4cc(F)cn4)nc3)[C@@H](C)C2)n1] |
| 117 | 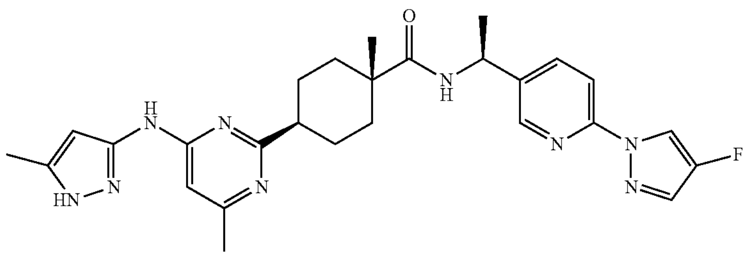 [SMILES: Cc1cc(Nc2cc(C)[nH]n2)nc([C@H]2CC[C@](C)(C(=O)N[C@@H](C)c3ccc(-n4cc(F)cn4)nc3)CC2)n1] |
| 118 | 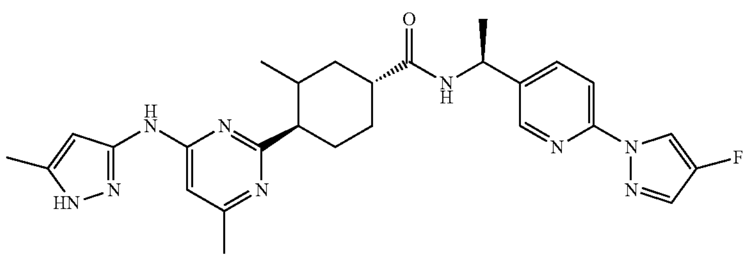 [SMILES: Cc1cc(Nc2cc(C)[nH]n2)nc([C@@H]2CC[C@@H](C(=O)N[C@@H](C)c3ccc(-n4cc(F)cn4)nc3)CC2C)n1] |
| 119 | 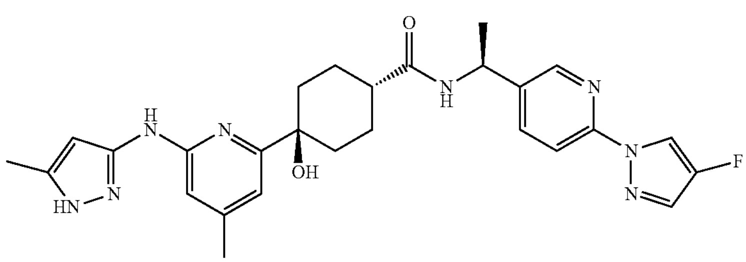 [SMILES: Cc1cc(Nc2cc(C)[nH]n2)nc([C@]2(O)CC[C@H](C(=O)N[C@@H](C)c3ccc(-n4cc(F)cn4)nc3)CC2)c1] |
| 120 | 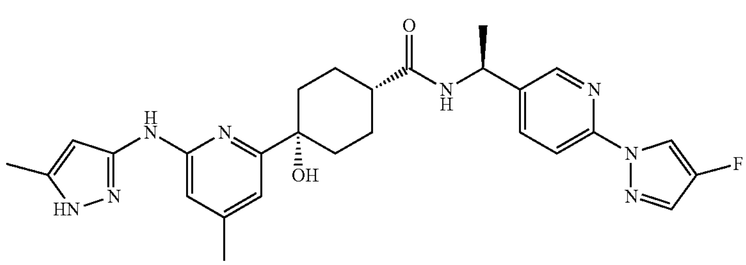 [SMILES: Cc1cc(Nc2cc(C)[nH]n2)nc([C@]2(O)CC[C@@H](C(=O)N[C@@H](C)c3ccc(-n4cc(F)cn4)nc3)CC2)c1] |
| 121 | 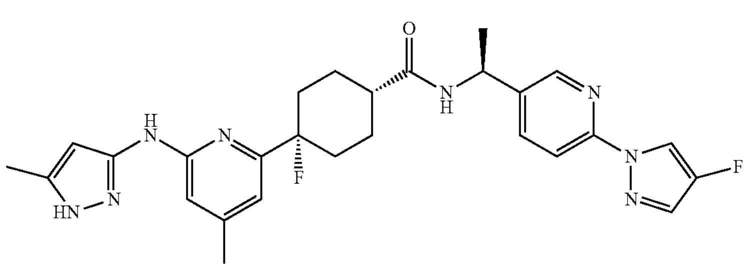 [SMILES: Cc1cc(Nc2cc(C)[nH]n2)nc([C@]2(F)CC[C@@H](C(=O)N[C@@H](C)c3ccc(-n4cc(F)cn4)nc3)CC2)c1] |

TABLE 1-continued

Exemplary Compounds of the Invention.

| Compound | Structure |
|---|---|
| 122 | 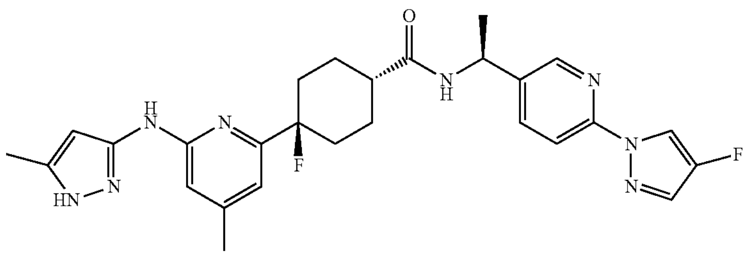 [SMILES: Cc1cc(Nc2cc(C)[nH]n2)nc([C@]2(F)CC[C@H](C(=O)N[C@@H](C)c3ccc(-n4cc(F)cn4)nc3)CC2)c1] |
| 123 | 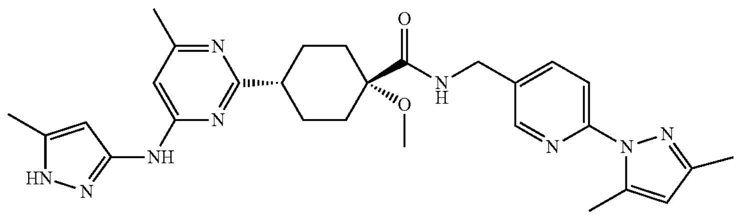 |
| 124 | 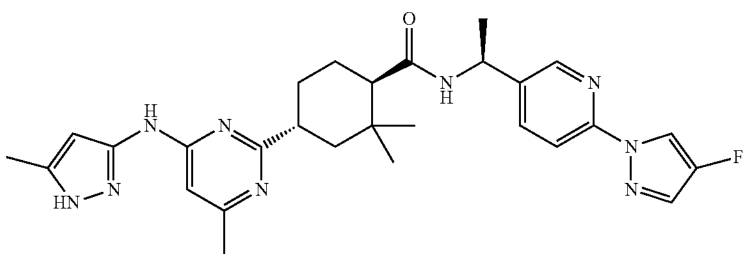 [SMILES: Cc1cc(Nc2cc(C)[nH]n2)nc([C@@H]2CC[C@@H](C(=O)N[C@@H](C)c3ccc(-n4cc(F)cn4)nc3)C(C)(C)C2)n1] |
| 125 | 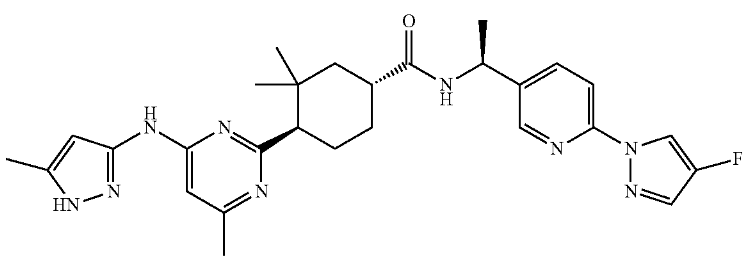 [SMILES: Cc1cc(Nc2cc(C)[nH]n2)nc([C@@H]2CC[C@@H](C(=O)N[C@@H](C)c3ccc(-n4cc(F)cn4)nc3)CC2(C)C)n1] |
| 126 | 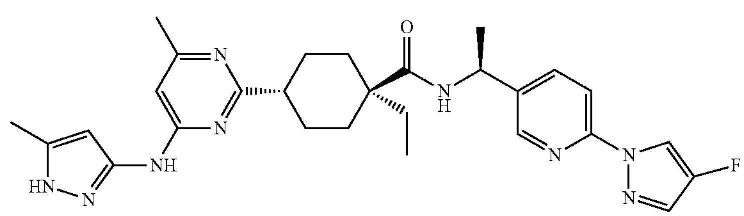 [SMILES: CC[C@]1(C(=O)N[C@@H](C)c2ccc(-n3cc(F)cn3)nc2)CC[C@H](c2nc(C)cc(Nc3cc(C)[nH]n3)n2)CC1] |
| 127 | 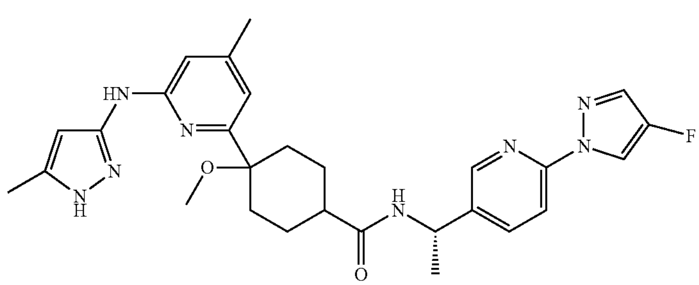 [SMILES: COC1(c2cc(C)cc(Nc3cc(C)[nH]n3)n2)CCC(C(=O)N[C@@H](C)c2ccc(-n3cc(F)cn3)nc2)CC1] |

TABLE 1-continued

Exemplary Compounds of the Invention.

| Compound | Structure |
|---|---|
| 128 | 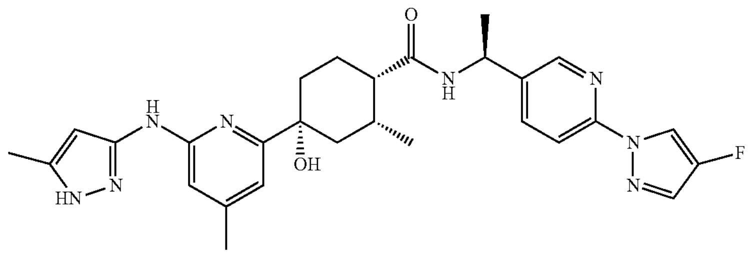 [SMILES: Cc1cc(Nc2cc(C)[nH]n2)nc([C@@]2(O)CC[C@H](C(=O)N[C@@H](C)c3ccc(-n4cc(F)cn4)nc3)[C@H](C)C2)c1] |
| 129 | 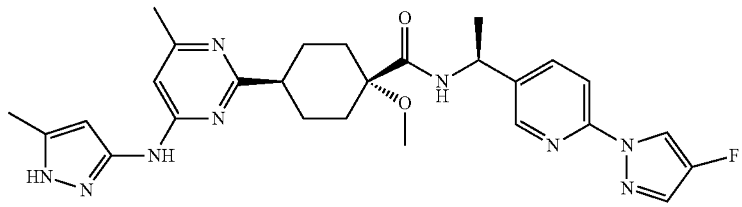 [SMILES: CO[C@]1(C(=O)N[C@@H](C)c2ccc(-n3cc(F)cn3)nc2)CC[C@@H](c2nc(C)cc(Nc3cc(C)[nH]n3)n2)CC1] |
| 130 | 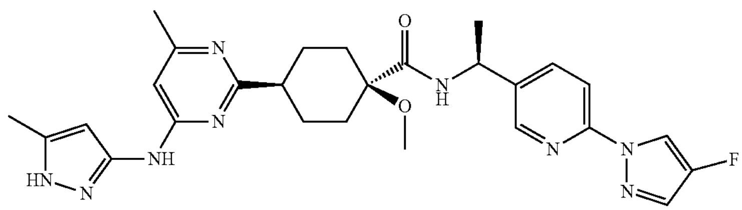 [SMILES: CO[C@]1(C(=O)N[C@@H](C)c2ccc(-n3cc(F)cn3)nc2)CC[C@H](c2nc(C)cc(Nc3cc(C)[nH]n3)n2)CC1] |
| 131 | 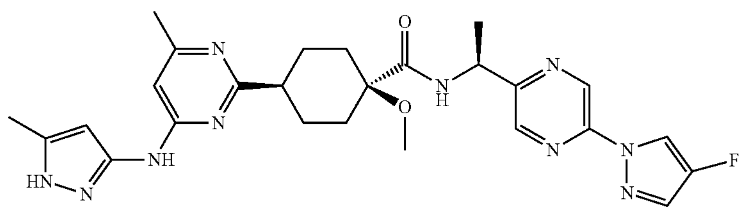 [SMILES: CO[C@]1(C(=O)N[C@@H](C)c2cnc(-n3cc(F)cn3)cn2)CC[C@H](c2nc(C)cc(Nc3cc(C)[nH]n3)n2)CC1] |
| 132 | 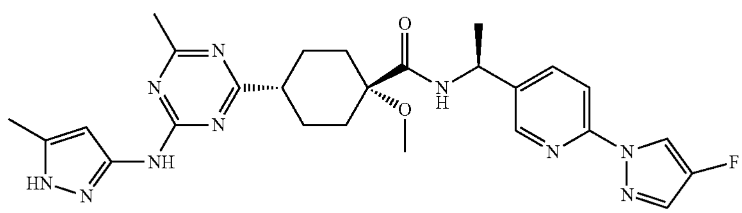 [SMILES: CO[C@]1(C(=O)N[C@@H](C)c2ccc(-n3cc(F)cn3)nc2)CC[C@H](c2nc(C)nc(Nc3cc(C)[nH]n3)n2)CC1] |
| 133 | 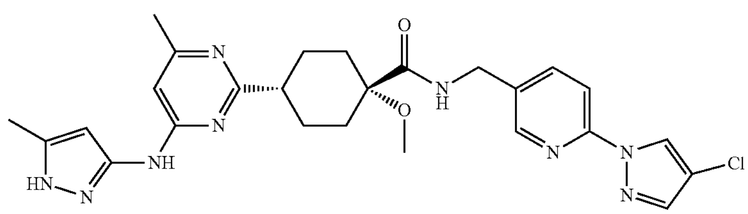 [SMILES: CO[C@]1(C(=O)NCc2ccc(-n3cc(Cl)cn3)nc2)CC[C@H](c2nc(C)cc(Nc3cc(C)[nH]n3)n2)CC1] |
| 134 | 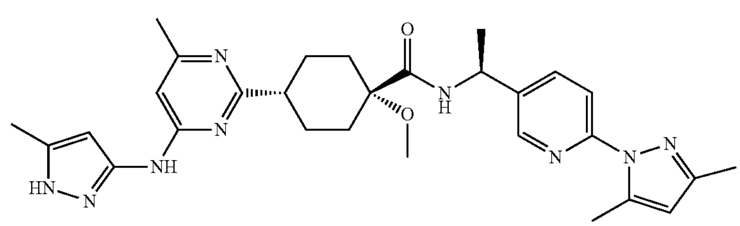 |

TABLE 1-continued

Exemplary Compounds of the Invention.

| Compound | Structure |
|---|---|
| 135 | 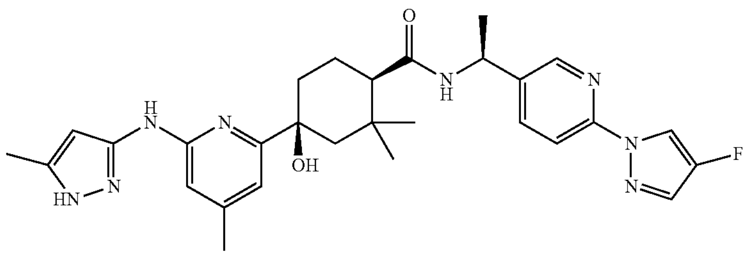 [SMILES: Cc1cc(Nc2cc(C)[nH]n2)nc([C@]2(O)CC[C@@H](C(=O)N[C@@H](C)c3ccc(-n4cc(F)cn4)nc3)C(C)(C)C2)c1] |
| 136 | 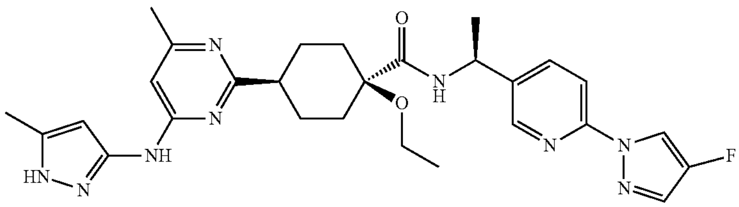 [SMILES: CCO[C@]1(C(=O)N[C@@H](C)c2ccc(-n3cc(F)cn3)nc2)CC[C@H](c2nc(C)cc(Nc3cc(C)[nH]n3)n2)CC1] |
| 137 | 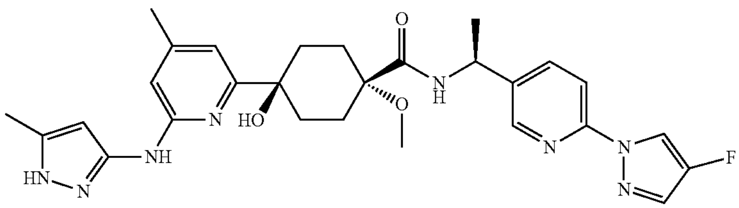 [SMILES: CO[C@]1(C(=O)N[C@@H](C)c2ccc(-n3cc(F)cn3)nc2)CC[C@](O)(c2cc(C)cc(Nc3cc(C)[nH]n3)n2)CC1] |
| 138 | 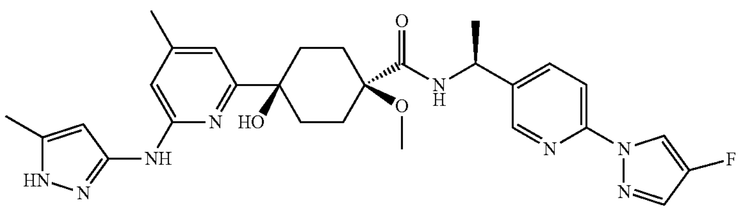 [SMILES: CO[C@]1(C(=O)N[C@@H](C)c2ccc(-n3cc(F)cn3)nc2)CC[C@@](O)(c2cc(C)cc(Nc3cc(C)[nH]n3)n2)CC1] |
| 139 | 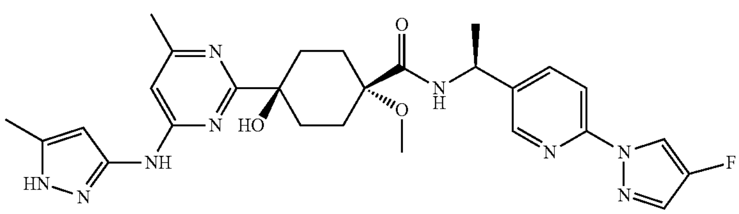 [SMILES: CO[C@]1(C(=O)N[C@@H](C)c2ccc(-n3cc(F)cn3)nc2)CC[C@](O)(c2nc(C)cc(Nc3cc(C)[nH]n3)n2)CC1] |
| 140 | 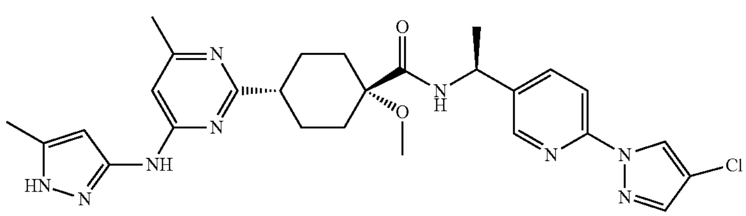 [SMILES: CO[C@]1(C(=O)N[C@@H](C)c2ccc(-n3cc(Cl)cn3)nc2)CC[C@H](c2nc(C)cc(Nc3cc(C)[nH]n3)n2)CC1] |
| 141 | 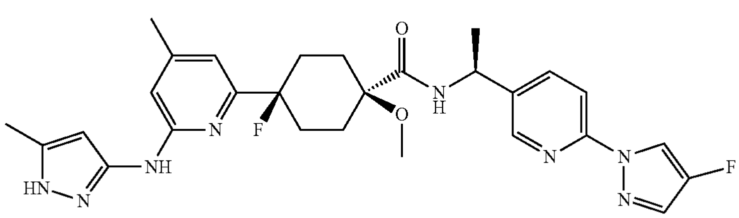 [SMILES: CO[C@]1(C(=O)N[C@@H](C)c2ccc(-n3cc(F)cn3)nc2)CC[C@@](F)(c2cc(C)cc(Nc3cc(C)[nH]n3)n2)CC1] |

TABLE 1-continued

Exemplary Compounds of the Invention.

| Compound | Structure |
|---|---|
| 142 | 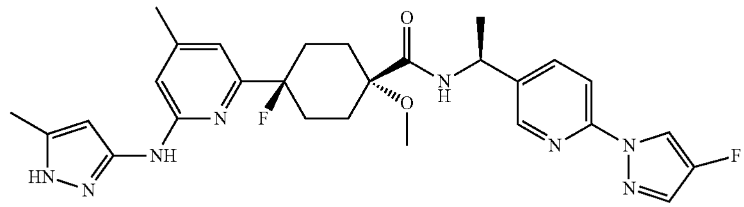 [SMILES: CO[C@]1(C(=O)N[C@@H](C)c2ccc(-n3cc(F)cn3)nc2)CC[C@](F)(c2cc(C)cc(Nc3cc(C)[nH]n3)n2)CC1] |
| 143 | 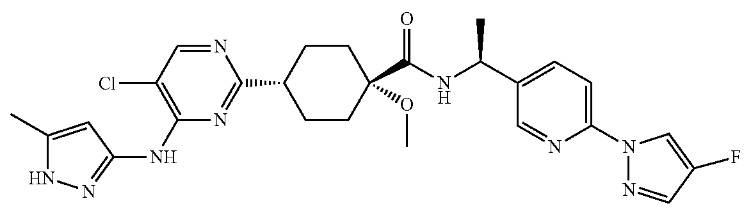 [SMILES: CO[C@]1(C(=O)N[C@@H](C)c2ccc(-n3cc(F)cn3)nc2)CC[C@H](c2ncc(Cl)c(Nc3cc(C)[nH]n3)n2)CC1] |
| 144 | 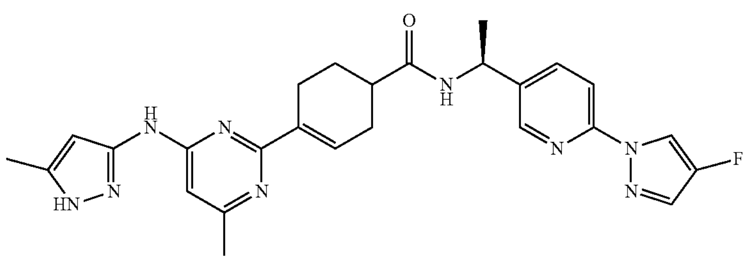 [SMILES: Cc1cc(Nc2cc(C)[nH]n2)nc(C2=CCC(C(=O)N[C@@H](C)c3ccc(-n4cc(F)cn4)nc3)CC2)n1] |
| 145 | 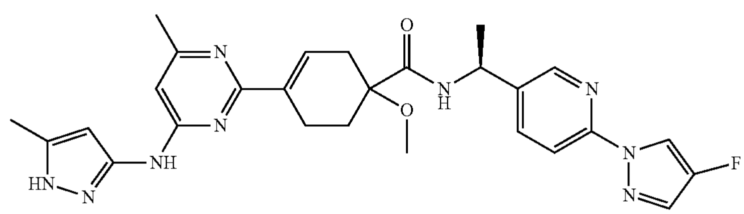 [SMILES: COC1(C(=O)N[C@@H](C)c2ccc(-n3cc(F)cn3)nc2)CC=C(c2nc(C)cc(Nc3cc(C)[nH]n3)n2)CC1] |
| 146 | 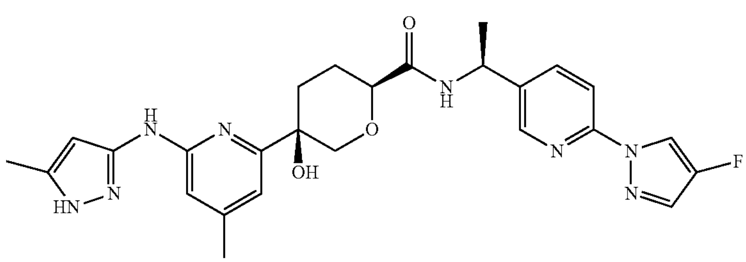 [SMILES: Cc1cc(Nc2cc(C)[nH]n2)nc([C@]2(O)CC[C@@H](C(=O)N[C@@H](C)c3ccc(-n4cc(F)cn4)nc3)OC2)c1] |
| 147 | 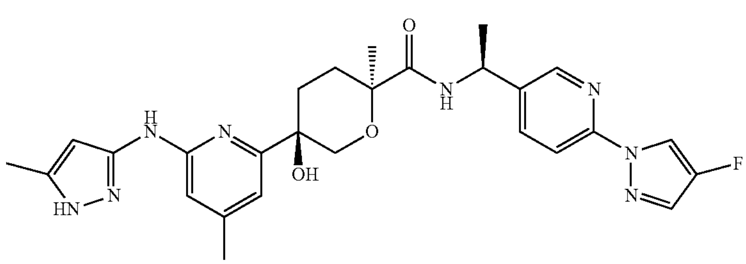 [SMILES: Cc1cc(Nc2cc(C)[nH]n2)nc([C@]2(O)CC[C@@](C)(C(=O)N[C@@H](C)c3ccc(-n4cc(F)cn4)nc3)OC2)c1] |

TABLE 1-continued

Exemplary Compounds of the Invention.

| Compound | Structure |
|---|---|
| 148 | *(structure)* |
| 149 | *(structure)* |
| 150 | *(structure)* |
| 151 | *(structure)* |

Pharmaceutically acceptable salts of these compounds are also contemplated for the uses described herein.

"Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical Compositions

Pharmaceutical compositions of the invention comprise one or more compounds of the invention and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the invention are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present invention that may be combined with the carrier materials to produce a composition in a single dosage form will vary depending upon the host treated, the particular mode of administration.

Dosages

Toxicity and therapeutic efficacy of compounds of the invention, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Treatment

RET fusions have been implicated in several types of cancers. Generally, these RET fusions have a RET kinase domain that is the same as in wild-type RET; therefore, as used herein, any RET protein with the same kinase domain as wild-type RET will be referred to as "wild-type RET." Mutations can occur in the RET kinase domain, leading to resistant mutants of RET.

The activity of exemplary compounds that are approved or in development for RET-related conditions is shown below. As shown, the compounds are active against the wild-type RET, but are much less active against the mutated forms.

| Compound | RET wt Biochemical $IC_{50}$ (nM) | RET V804L Biochemical $IC_{50}$ (nM) |
| --- | --- | --- |
| Cabozantinib | 11 | 45 |
| Vandetanib | 4 | 3597 |
| Sorafenib | 7.9 | 95.2 |
| Regorafenib | 12 | 53 |

The invention provides compounds that inhibit both wild-type RET and mutants of RET, e.g., mutants of RET that are resistant to current standard of care treatments ("RET resistant mutants"). In addition, the compounds of the invention can be selective for wild-type RET, over other kinases, thus leading to reduced toxicities associated with inhibiting other kinases.

Mutations can be predicted using structural biology and computational analyses, as well as by examining codon sequences in which a sequence change gives rise to a codon for a different amino acid. Using such methods, RET resistant mutants are predicted to have point mutations at the 804 gatekeeper residue in the RET protein and/or at residues at or near the gatekeeper residue. In some embodiments, the mutation may be at one or more of the 804, 806, 810, 865, 870, 891, or 918 residues. Specific examples of RET resistant mutants include: V804L, V804M, V804E, Y806C, Y806S, Y806H, Y806N, G810R, G810S, L865V, L870F, S891A and M918T mutants.

Mutations occurring from administration of a particular inhibitor (e.g., a known RET wild-type inhibitor) can be determined experimentally by exposing cells to a mutation-promoting agent, such as ENU. The cells are washed, then plated with increasing concentrations (2-100× proliferation $IC_{50}$) of the compound of choice. The wells with cellular outgrowth are then collected after 3-4 weeks. The RET kinase domain is then sequenced to identify resistance mutations (i.e., altered forms of the RET protein that retain enzymatic activity). Resistance can be confirmed by exposing these cells with the compound of choice. Resistant mutants that have been identified experimentally include the V804L, V804E, V804M, and Y806H mutants.

Because of their activity against wild-type RET and mutant RET, the compounds described herein can be used to treat a patient with a condition associated with aberrant RET activity. They can also be used to treat various cancers. In some embodiments, the cancer is selected from papillary thyroid carcinoma (PTC), medullary thyroid cancer (MTC), pheochromocytoma (PC), pancreatic ductal adenocarcinoma, multiple endocrine neoplasia (MEN2A and MEN2B), metastatic breast cancer, testicular cancer, small cell lung cancer, non-small cell lung cancer, chronic myelomonocytic leukemia, colorectal cancer, ovarian cancer, and cancers of the salivary gland.

The compounds can also be used to treat a patient who has developed resistance to a wild-type RET inhibitor, or a patient with a particular RET mutant. The method includes the step of administering a compound or composition of the invention that is active against one or more RET resistant mutants. In certain embodiments, the RET resistant mutant is selected from V804L, V804M, V804E, Y806C, Y806S, Y806N, Y806H, G810R, G810S, L865V, L870F, S891A and M918T. By "active" is meant that a compound has an $IC_{50}$ of less than 1 µM, 500 nM, 250 nM, 100 nM, 75 nM, 50 nM, 25 nM, 10 nM, or 5 nM when measured in a biochemical assay, against at least one resistant mutant.

The compounds and compositions described herein can be administered alone or in combination with other compounds, including other RET-modulating compounds, or other therapeutic agents. In some embodiments, the compound or composition of the invention may be administered in combination with one or more compounds selected from Cabozantinib (COMETRIQ), Vandetanib (CALPRESA), Sorafenib (NEXAVAR), Sunitinib (SUTENT), Regorafenib (STAVARGA), Ponatinib (ICLUSIG), Bevacizumab (AVASTIN), Crizotinib (XALKORI), or Gefitinib (IRESSA). The compound or composition of the invention may be administered simultaneously or sequentially with the other therapeutic agent by the same of different routes of administration. The compound of the invention may be included in a single formulation with the other therapeutic agent or in separate formulations.

EXAMPLES

The following examples are intended to be illustrative, and are not meant in any way to be limiting.

Compounds of the invention, including salts and N-oxides thereof, can be prepared using known organic synthesis techniques and can be synthesized according to any of numerous possible synthetic routes, such as those in the Synthetic Protocols below and in the Examples. The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol 1:

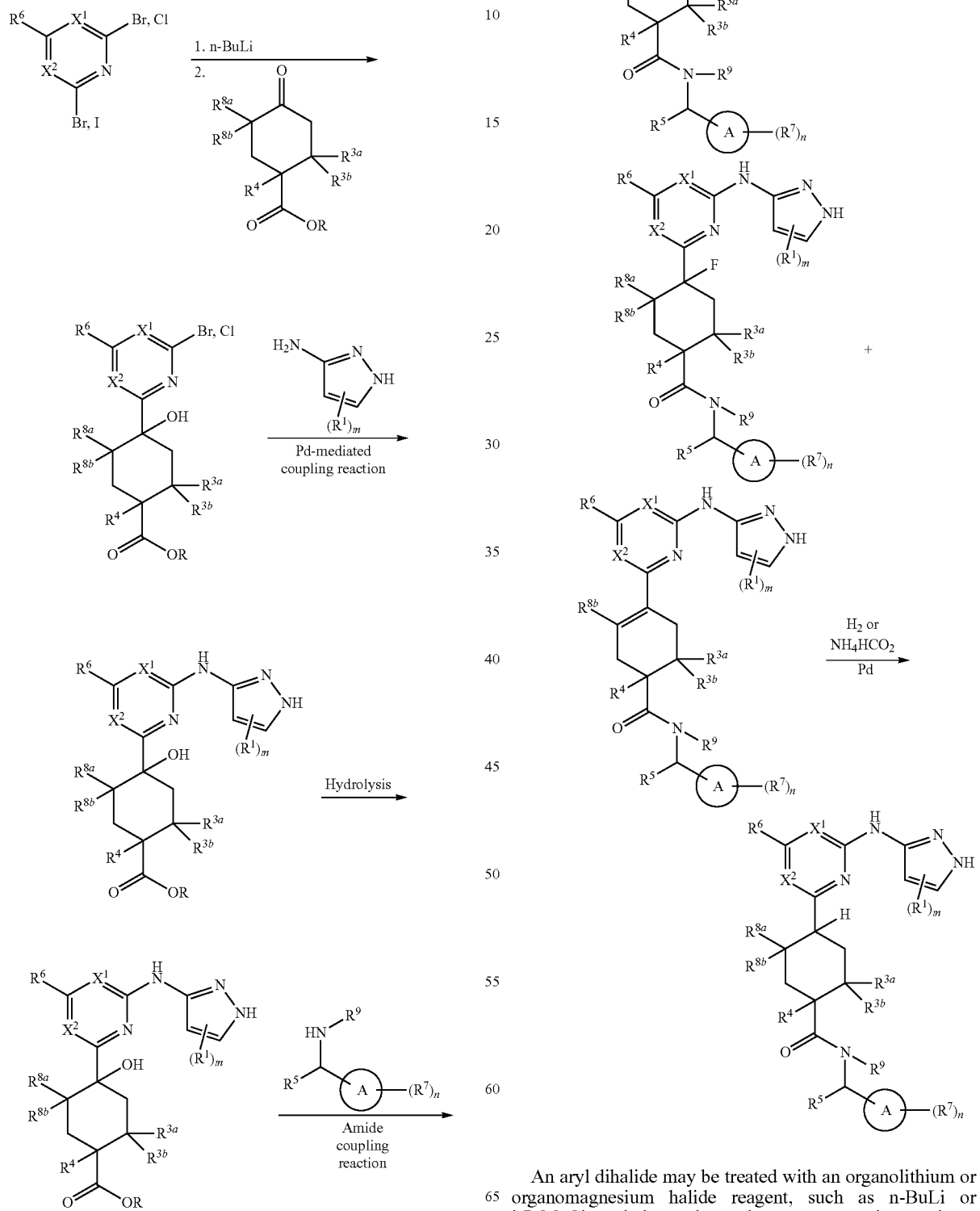

An aryl dihalide may be treated with an organolithium or organomagnesium halide reagent, such as n-BuLi or i-PrMgCl, and the aryl metal reagent may then undergo addition to an ester substituted cyclohexanone (either commercially available or prepared as described in "Synthesis of Ketone and Boronate Intermediates"). The remaining halide can then undergo a coupling reaction with an arylamine under SnAr conditions or metal-catalyzed coupling conditions to give a tricyclic ester intermediate. The ester can then be hydrolyzed under basic conditions to give an acid, which can then undergo an amide coupling reaction with an amine (either commercially available or prepared as described in "Synthesis of Amine Intermediates"). The amides are examples of RET inhibitors described herein, but can also be further modified. For example, the tertiary alcohol can be treated with a fluorinating reagent such as DAST to give a mixture of deoxyfluorinated products and dehydrated products. The dehydrated products can be reduced under typical hydrogenation conditions such as Pd and $H_2$, or Pd and ammonium formate to give the reduced products which are also examples of RET inhibitors.

Synthetic Protocol 2:

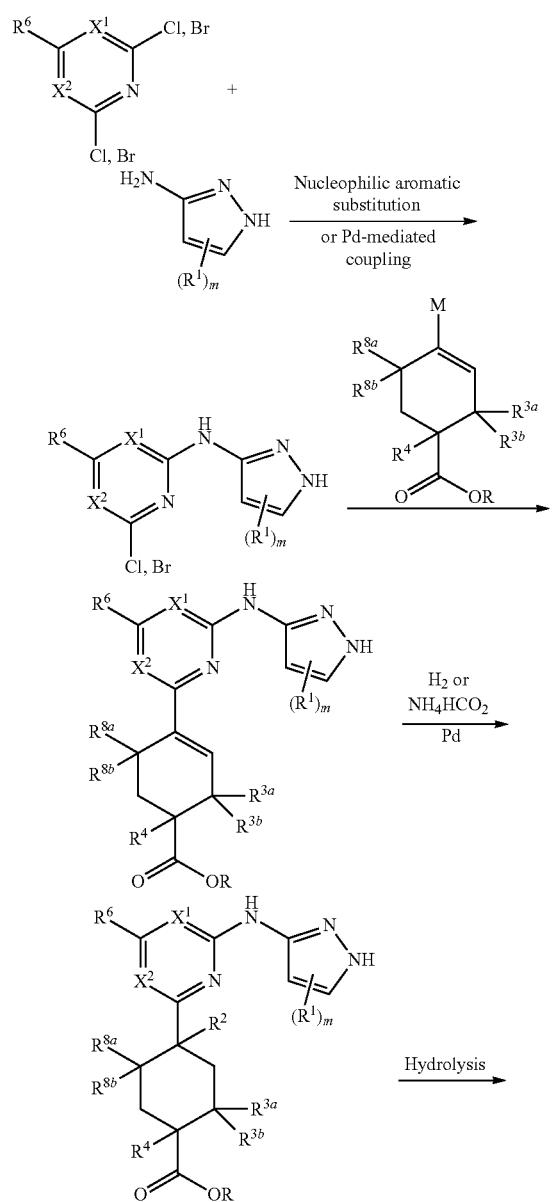

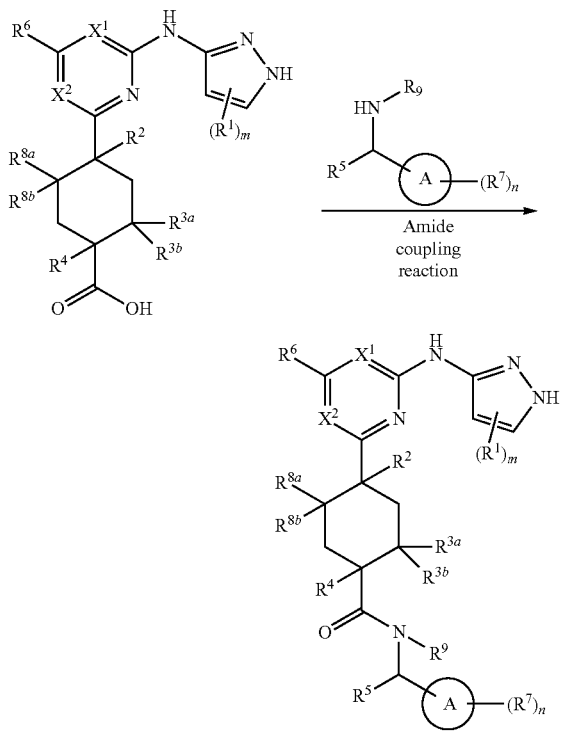

The heteroaryl dihalide can be coupled to an amino pyrazole under nucleophilic aromatic substitution reaction conditions using a base such as diisopropylethylamine (DIPEA) or triethylamine (TEA) in a polar solvent to provide the bicyclic ring system. The bicyclic heteroaryl halide can then be coupled to a to a boron, tin or zinc alkenyl or alkyl reagent via a Palladium-mediated coupling reaction, e.g., Suzuki, Stille, Negishi coupling, to provide the tricyclic ring system. For example, in Synthetic Protocol 2, the bicyclic heteroaryl halide of the can be coupled to a variety of ester substituted cyclohexenyl boronic esters (commercially available or those described under the heading "Synthesis of Vinyl Boronates") under Suzuki coupling reaction conditions (X=halo, e.g., chloro; and $M=B(OR)_2$) to provide the tricyclic carboxylic ester intermediate. The carboxylic ester can then be hydrolyzed under acidic or basic conditions to provide a carboxylic acid intermediate. The carboxylic acid intermediate can then be coupled to a variety of amine intermediates, such as those described in Example 9 to provide the amide final product.

Synthetic Protocol 3:

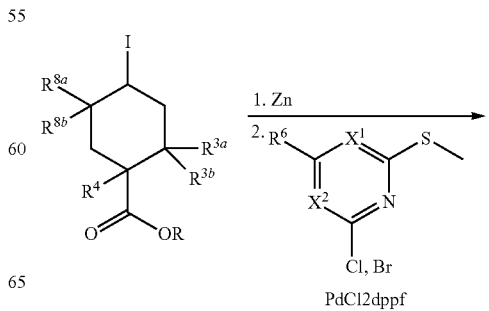

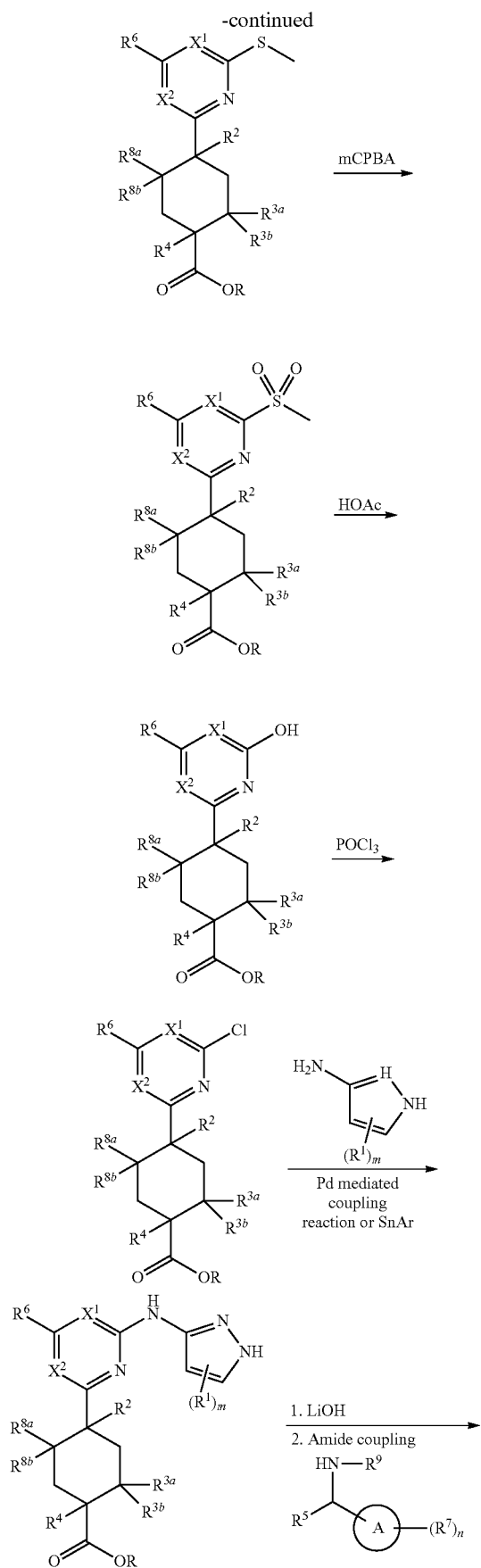
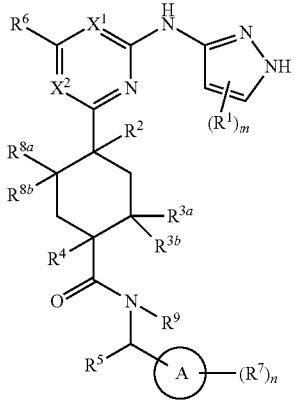

A substituted cycloalkyl iodide (either commercially available or prepared as described in "Synthesis of Iodide Intermediates") was treated with activated zinc. The zinc was then activated by a variety methods, including but not limited to the method of Reike or treatment with TMS-Cl and 1,2-dibromoethane. The cycloalkyl zinc reagent can then be coupled to a heteroaryl halide with palladium catalysis under Negishi coupling conditions. The thiomethyl group of the resulting product can then be converted to a chloride via oxidation to the sulfone, hydrolysis under acidic conditions, and chlorination with $POCl_3$ or oxalyl chloride. The heteroaryl chloride can then undergo displacement with an aryl amine under either SnAr conditions or palladium mediated coupling conditions. The tricyclic carboxylic ester can then be hydrolyzed under acidic or basic conditions to provide a carboxylic acid intermediate. The carboxylic acid intermediate can then be coupled to a variety of amines intermediates, such as those described in Example 9 to provide the amide final product.

Synthetic Protocol 4:

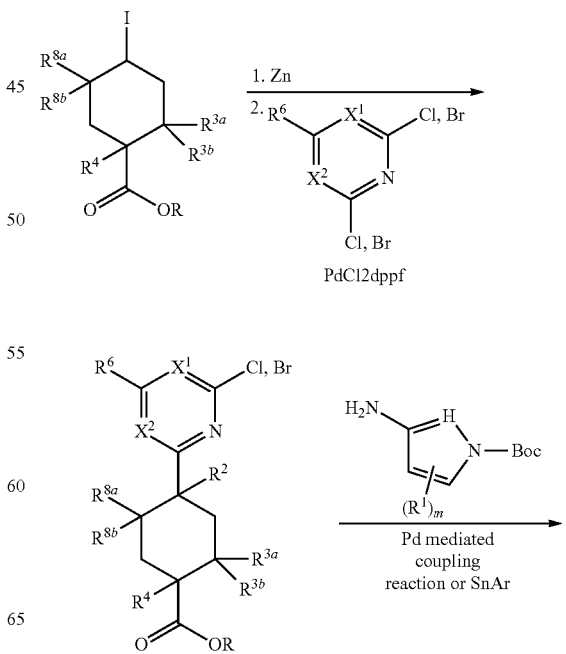

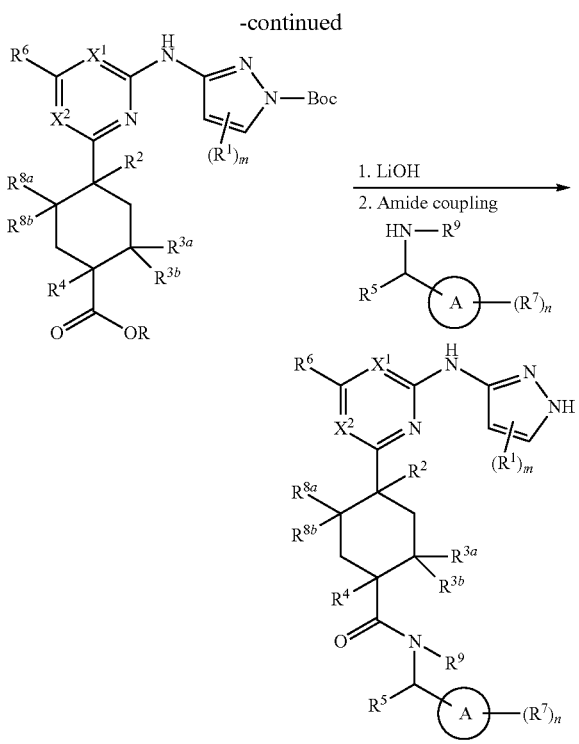

A substituted cycloalkyl iodide (either commercially available or prepared as described in "Synthesis of Iodide Intermediates") was treated with activated zinc. The zinc could be activated by a variety methods, including but not limited to the method of Reike or treatment with TMS-Cl and 1,2-dibromoethane. The cycloalkyl zinc reagent can then be coupled to a heteroaryl dihalide with palladium catalysis under Negishi coupling conditions. The remaining halide group of the resulting product can then undergo displacement with an aryl amine under either SnAr conditions or palladium mediated coupling conditions. The aryl amine can either be unprotected or the pyrazole N—H can be protected with a variety of groups, such as Boc. The tricyclic carboxylic ester can then be hydrolyzed under acidic or basic conditions to provide a carboxylic acid intermediate, which also removes the protecting group from the pyrazole. The carboxylic acid intermediate can then be coupled to a variety of amines intermediates, such as those described in "Synthesis of Amine Intermediates" to provide the amide final product.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: Unless otherwise indicated, all liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Silica gel chromatography: Silica gel chromatography was performed on either a Teledyne Isco CombiFlash® Rf unit or a Biotage® Isolera Four unit.

Proton NMR: Unless otherwise indicated, all $^1$H NMR spectra were obtained with a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm).

Example 1. Synthesis of Compounds 109 and 110

Step 1: Synthesis of (1R,4S)—N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 109) and (1S,4R)-N—((S)-1-(6-(4-fluoro-1H-pyrazol-1-yl) pyridin-3-yl)ethyl)-4-(4-methyl-6-(5-methyl-1H-pyrazol-3-ylamino)pyridin-2-yl)cyclohexanecarbox-amide (Compound 110)

N—((S)-1-(6-(4-fluoro-1H-pyrazol-1-yl)pyridin-3-yl) ethyl)-4-(4-methyl-6-((5-methyl-1H-pyrazol-3-yl)amino) pyridin-2-yl)cyclohex-3-enecarboxamide (50 mg, 0.10 mmol) and 10% Pd/C (20 mg) in MeOH (5 mL) was stirred at ambient temperature under a H$_2$ atmosphere (1 atm) for 1 h. The mixture was then filtered through a pad of celite, and the filtered solution was concentrated and purified by preparative HPLC to give both of title compounds (1R,4S)—N—((S)-1-(6-(4-fluoro-1H-pyrazol-1-yl)pyridin-3-yl)

ethyl)-4-(4-methyl-6-(5-methyl-1H-pyrazol-3-ylamino) pyridin-2-yl)cyclohexanecarboxamide (Compound 109; 10.0 mg, 19.9%) and (1S,4R)-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 110; 24.8 mg, 49.5%) as a white solid. MS (ES+) $C_{27}H_3FN_8O$ requires: 502, found: 503 [M+H]$^+$. (1R, 4S)—N—((S)-1-(6-(4-fluoro-1H-pyrazol-1-yl)pyridin-3-yl) ethyl)-4-(4-methyl-6-(5-methyl-1H-pyrazol-3-ylamino) pyridin-2-yl)cyclohexanecarboxamide (Compound 109): $^1$H-NMR (400 MHz, DMSO-d6) δ ppm 11.66 (s, 1H), 8.82 (s, 1H), 8.68 (d, 1H, J=4.4 Hz), 8.39 (s, 1H), 8.35 (d, 1H, J=6.8 Hz), 7.92-7.86 (m, 3H), 6.89 (s, 1H), 6.37 (s, 1H), 6.12 (s, 1H), 5.00-4.97 (m, 1H), 2.50-2.44 (m, 1H), 2.40-2.15 (m, 7H), 1.90-1.85 (m, 4H), 1.55-1.45 (m, 4H), 1.40 (d, 3H, J=6.4 Hz). (1S,4R)-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 110): $^1$H-NMR (400 MHz, DMSO-d6) δ ppm 11.62 (s, 1H), 8.78 (s, 1H), 8.66 (d, 1H, J=4.4 Hz), 8.38 (d, 1H, J=1.6 Hz), 8.23 (d, 1H, J=7.6 Hz), 7.93-7.84 (m, 3H), 6.83 (s, 1H), 6.35 (s, 1H), 6.15 (s, 1H), 5.03-5.00 (m, 1H), 2.59-2.50 (m, 1H), 2.50-2.46 (m, 1H), 2.14-2.02 (m, 6H), 2.02-1.84 (m, 4H), 1.63-1.55 (m, 4H), 1.40 (d, 3H, J=7.6 Hz).

Example 2. Synthesis of Compound 112

Step 1: Synthesis of 2-chloro-6-methyl-N-(5-methyl-1H-pyrazol-3-yl)pyrimidin-4-amine

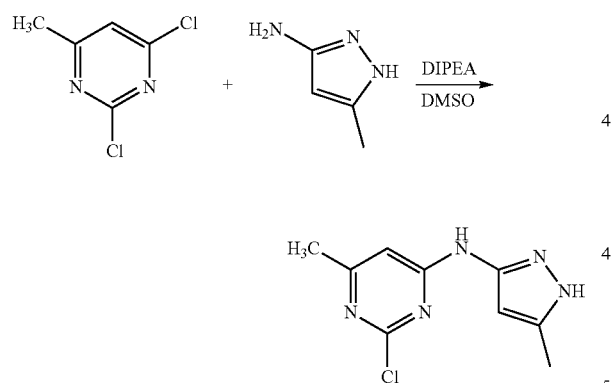

A suspension of 2,4-dichloro-6-methyl-pyrimidine (120.00 g, 736.2 mmol, 1.00 eq), 5-methyl-1H-pyrazol-3-amine (78.65 g, 0.81 mol, 1.10 eq) and DIPEA (142.72 g, 1.10 mol, 1.50 eq) in DMSO (400.00 mL) was heated at 60° C. for 16 hrs, at which point TLC (PE/EA, 5:1, 1:1) analysis showed the reaction was complete. The reaction mixture was cooled to 30° C., poured into ice-water (800 mL), and the resulting mixture was extracted with MTBE (800 mL×10). The combined organic layers were washed with water (400 mL×3), brine (400 mL×3) and dried over $Na_2SO_4$. After filtration, the filtrate was concentrated under reduced pressure and the residue was recrystallized from DCM (10 mL/g) to afford 2-chloro-6-methyl-N-(5-methyl-1H-pyrazol-3-yl)pyrimidin-4-amine (105.60 g, 472.14 mmol, 64%) as a yellow solid. The structure was confirmed by LC-MS and NMR.

Step 2: Synthesis of ethyl 4-(4-methyl-6-((5-methyl-1H-pyrazol-3-yl)amino)pyrimidin-2-yl)cyclohex-3-ene-1-carboxylate

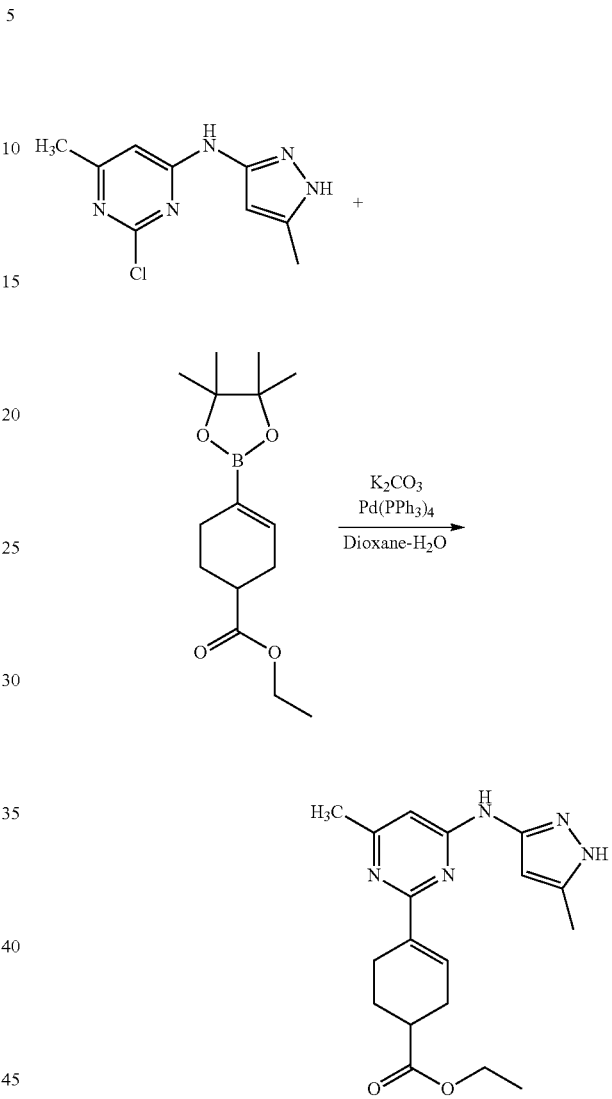

A mixture of 2-chloro-6-methyl-N-(5-methyl-1H-pyrazol-3-yl)pyrimidin-4-amine (0.530 g, 2.37 mmol), ethyl 4-(4,4,5,5-tetramethyl-1,3,2-dioxaborolan-2-yl)cyclohex-3-enecarboxylate (0.664 g, 2.37 mmol), and potassium carbonate (0.819 g, 5.92 mmol) in dioxane (8.89 ml) and water (2.96 ml) was sparged with nitrogen gas for 10 min, then Pd(PPh$_3$)$_4$ (0.137 g, 0.118 mmol) was added and the reaction vessel was sealed. The reaction mixture was heated in a microwave reactor at 125° C. for 80 min, then cooled to ambient temperature and partitioned between 5:1 DCM/IPA and water. The aqueous layer was further extracted with 5:1 DCM/IPA. The organic layers were combined and dried over sodium sulfate. The dried solution was filtered, concentrated, and purified by silica gel chromatography (gradient elution, 0 to 10% methanol-DCM) to give ethyl 4-(4-methyl-6-((5-methyl-1H-pyrazol-3-yl)amino)pyrimidin-2-yl)cyclohex-3-ene-1-carboxylate (646 mg, 80%) as a yellow solid. MS (ES+) $C_{18}H_{23}N_5O_2$ requires: 341, found: 342 [M+H]$^+$.

Step 3: Synthesis of ethyl 4-(4-methyl-6-((5-methyl-1H-pyrazol-3-yl)amino)pyrimidin-2-yl)cyclohexane-1-carboxylate

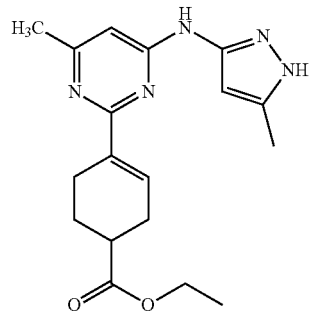

Palladium on carbon (10 wt %, 0.125 g, 0.117 mmol) and ammonium formate (0.296 g, 4.69 mmol) were added to a solution of ethyl 4-(4-methyl-6-((5-methyl-1H-pyrazol-3-yl)amino)pyrimidin-2-yl)cyclohex-3-enecarboxylate (0.40 g, 1.2 mmol) in ethanol (11.7 ml) and the resulting mixture was heated to 70° C. for 30 min. The reaction mixture was cooled to ambient temperature, and filtered through celite, rinsing the celite with methanol. The filtered solution was then concentrated onto silica gel and purified by silica gel chromatography (gradient elution, 0 to 10% methanol-DCM) to give ethyl 4-(4-methyl-6-((5-methyl-1H-pyrazol-3-yl)amino)pyrimidin-2-yl)cyclohexane-1-carboxylate as a 3:1 mixture of cis:trans. MS (ES+) $C_{18}H_{25}N_5O_2$ requires: 343, found: 344 [M+H]+.

Step 4: Synthesis of 4-(4-methyl-6-((5-methyl-1H-pyrazol-3-yl)amino)pyrimidin-2-yl)cyclohexane-1-carboxylic acid

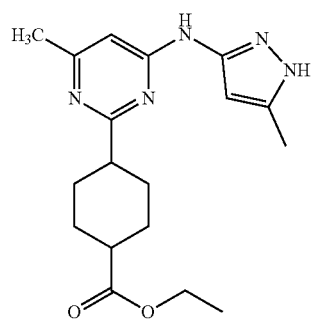

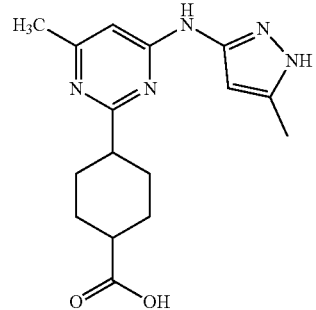

Lithium hydroxide monohydrate (0.029 g, 0.70 mmol) was added to a solution of ethyl 4-(4-methyl-6-((5-methyl-1H-pyrazol-3-yl)amino)pyrimidin-2-yl)cyclohexanecarboxylate (0.12 g, 0.35 mmol) in THF (2.8 mL), EtOH (2.8 mL), and water at ambient temperature. The reaction mixture was stirred for 6 h, then concentrated aqueous HCl (37%, 0.072 ml, 0.87 mmol) was added. The reaction mixture was concentrated and carried forward in the next step.

Step 5: Synthesis of (1R,4S)—N—((S)-1-(6-(4-fluoro-1H-pyrazol-1-yl)pyridin-3-yl)ethyl)-4-(4-methyl-6-((5-methyl-1H-pyrazol-3-yl)amino)pyrimidin-2-yl)cyclohexane-1-carboxamide (Compound 112)

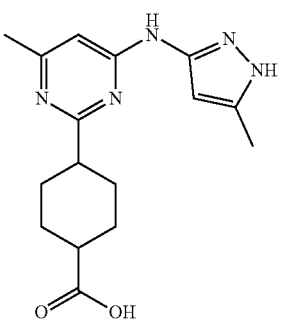

+

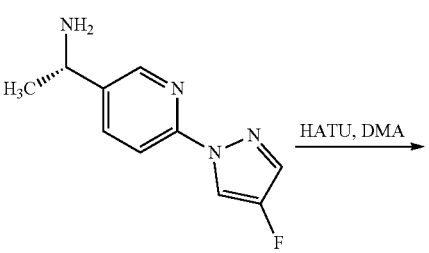

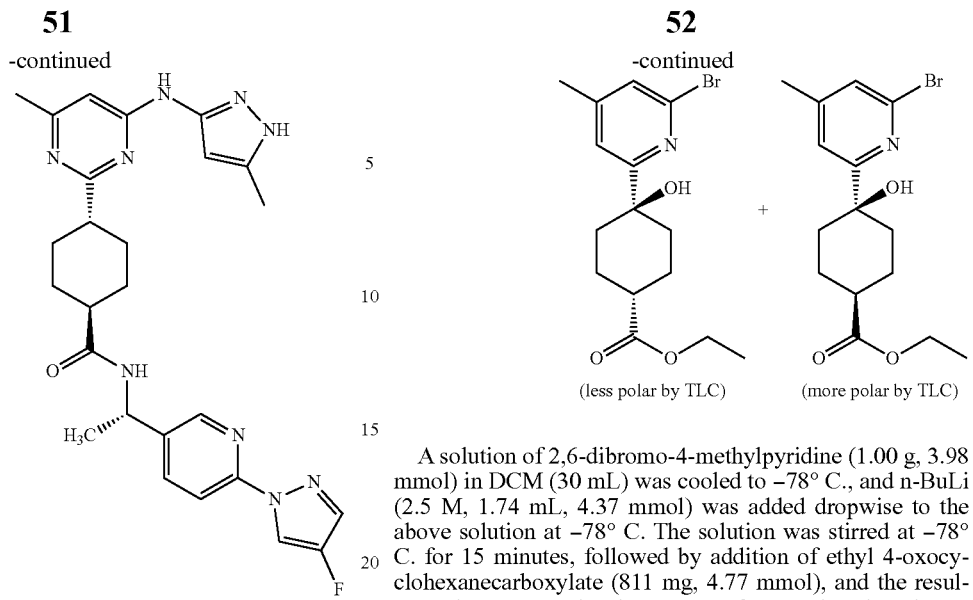

HATU (162 mg, 0.427 mmol) was added to a solution of crude 4-(4-methyl-6-((5-methyl-1H-pyrazol-3-yl)amino)pyrimidin-2-yl)cyclohexanecarboxylic acid (72 mg, 0.23 mmol), (5)-1-(6-(4-fluoro-1H-pyrazol-1-yl)pyridin-3-yl)ethanamine hydrochloride salt (97 mg, 0.40 mmol), and DIEA (0.34 mL, 1.9 mmol) in DMF (3.8 mL) at ambient temperature. The reaction mixture was stirred for 10 min, then was partitioned between EtOAc and H$_2$O. The organic layer was washed with saturated aqueous NaCl solution, dried over sodium sulfate, filtered, and concentrated. The residue was purified by silica gel chromatography (gradient elution 0 to 10% methanol-dichloromethane with 2% triethylamine added) to give (1R,4S)—N—((S)-1-(6-(4-fluoro-1H-pyrazol-1-yl)pyridin-3-yl)ethyl)-4-(4-methyl-6-((5-methyl-1H-pyrazol-3-yl)amino)pyrimidin-2-yl)cyclohexane-1-carboxamide (Compound 112; 26 mg, 13% yield) as a white solid. MS (ES+) C$_{26}$H$_{30}$FN$_9$O requires: 503, found: 504 [M+H]$^+$. $^1$H NMR (500 MHz, DMSO-d6) δ 11.88 (s, 1H), 9.48 (s, 1H), 8.66 (d, J=4.5 Hz, 1H), 8.38 (d, J=2.2 Hz, 1H), 8.30 (d, J=7.7 Hz, 1H), 7.94-7.81 (m, 3H), 6.83 (s, 1H), 6.16 (s, 1H) 5.02-4.93 (m, 1H), 2-57-2.49 (m, 1H), 2.26-2.16 (m, 7H), 1.99-1.92 (m, 2H), 1.88-1.80 (m, 2H), 1.58-1.36 (m, 7H).

Example 3. Synthesis of Compound 120

Step 1: Synthesis of (1S,4S)-ethyl 4-(6-bromo-4-methylpyridin-2-yl)-4-hydroxycyclohexanecarboxylate and (1R,4R)-ethyl 4-(6-bromo-4-methylpyridin-2-yl)-4-hydroxycyclohexanecarboxylate

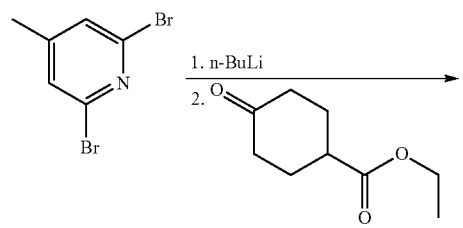

A solution of 2,6-dibromo-4-methylpyridine (1.00 g, 3.98 mmol) in DCM (30 mL) was cooled to −78° C., and n-BuLi (2.5 M, 1.74 mL, 4.37 mmol) was added dropwise to the above solution at −78° C. The solution was stirred at −78° C. for 15 minutes, followed by addition of ethyl 4-oxocyclohexanecarboxylate (811 mg, 4.77 mmol), and the resultant mixture was stirred at −78° C. for 30 min. The mixture was then quenched by addition of saturated aqueous NH$_4$Cl solution and extracted with DCM. Organic layers were combined, dried over sodium sulfate, filtered, and concentrated. The residue was purified by silica gel column (PE: EA=2:1) to give (1R,4R)-ethyl 4-(6-bromo-4-methylpyridin-2-yl)-4-hydroxycyclohexanecarboxylate (less polar by TLC, 500 mg, 36.7%) as a white solid, MS (ES+) C$_{15}$H$_{20}$BrNO$_3$ requires: 341, found: 342 [M+H]$^+$, and (1S, 4S)-ethyl 4-(6-bromo-4-methylpyridin-2-yl)-4-hydroxycyclohexanecarboxylate (more polar by TLC, 500 mg, 36.7%) as a white solid. MS (ES+) C$_{15}$H$_{20}$BrNO$_3$ requires: 341, found: 342 [M+H]$^+$.

Step 2: Synthesis of (1S,4S)-ethyl 4-hydroxy-4-(4-methyl-6-(5-methyl-1H-pyrazol-3-ylamino)pyridin-2-yl)cyclohexanecarboxylate

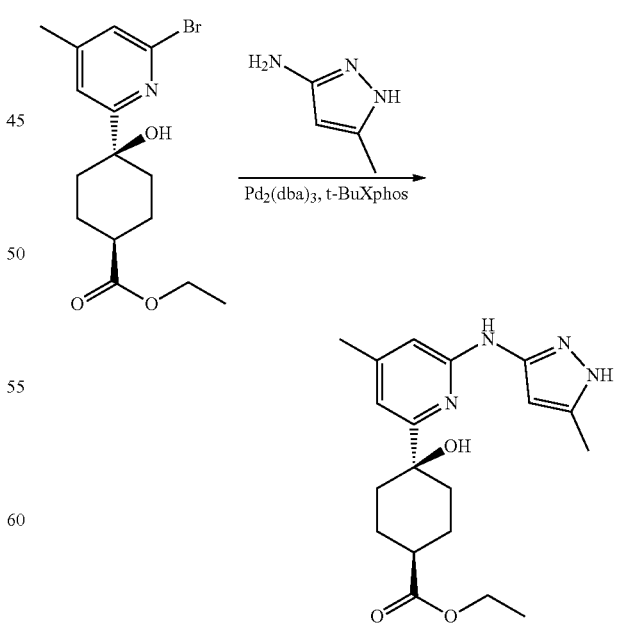

A mixture of (1s, 4s)-ethyl 4-(6-bromo-4-methylpyridin-2-yl)-4-hydroxycyclohexanecarboxylate (500 mg, 1.46 mmol), 5-methyl-1H-pyrazol-3-amine (283 mg, 2.92 mmol), t-BuXPhos (185 mg, 0.438 mmol), Pd$_2$(dba)$_3$ (200 mg, 0.219 mmol) and KOAc (429 mg, 4.38 mmol) in DMF (2 mL) and toluene (10 mL) was heated to 140° C. for 2 h under microwave irradiation. After cooling to ambient temperature, the mixture was concentrated and purified by silica gel column (PE:EA=1:2) to give (1s,4s)-ethyl 4-hydroxy-4-(4-methyl-6-(5-methyl-1H-pyrazol-3-ylamino)pyridin-2-yl)cyclohexanecarboxylate (80 mg, 15%) as a white solid. MS (ES+) C$_{19}$H$_{26}$N$_4$O$_3$ requires: 358, found: 359 [M+H]$^+$.

Step 3: Synthesis of (1S,4S)-4-hydroxy-4-(4-methyl-6-(5-methyl-1H-pyrazol-3-ylamino)pyridin-2-yl)cyclohexanecarboxylic acid To a solution of (1S,4S)-ethyl 4-hydroxy-4-(4-methyl-6-((5-methyl-1H-pyrazol-3-yl)amino)pyridin-2-yl)cyclohexanecarboxylate (80 mg, 0.2231 mmol) in MeOH (3 mL) was added 2 M aqueous NaOH (0.5 mL, 1 mmol) at 25° C. The solution was stirred at 25° C. for 15 h and then concentrated to remove MeOH. The aqueous solution was acidified with 2 M HCl to bring the pH to 6, which resulted in formation of a precipitate. The precipitated solid was collected and dried to give (1S,4S)-4-hydroxy-4-(4-methyl-6-(5-methyl-1H-pyrazol-3-ylamino)pyridin-2-yl)cyclohexanecarboxylic acid (60 mg, 81%) as a yellow solid. MS (ES+) C$_{17}$H$_{22}$N$_4$O$_3$ requires: 330, found: 331 [M+H]$^+$.

Step 4: Synthesis of (1s,4R)-N—((S)-1-(6-(4-fluoro-1H-pyrazol-1-yl)pyridin-3-yl)ethyl)-4-hydroxy-4-(4-methyl-6-(5-methyl-1H-pyrazol-3-ylamino)pyridin-2-yl)cyclohexanecarboxamide (Compound 120)

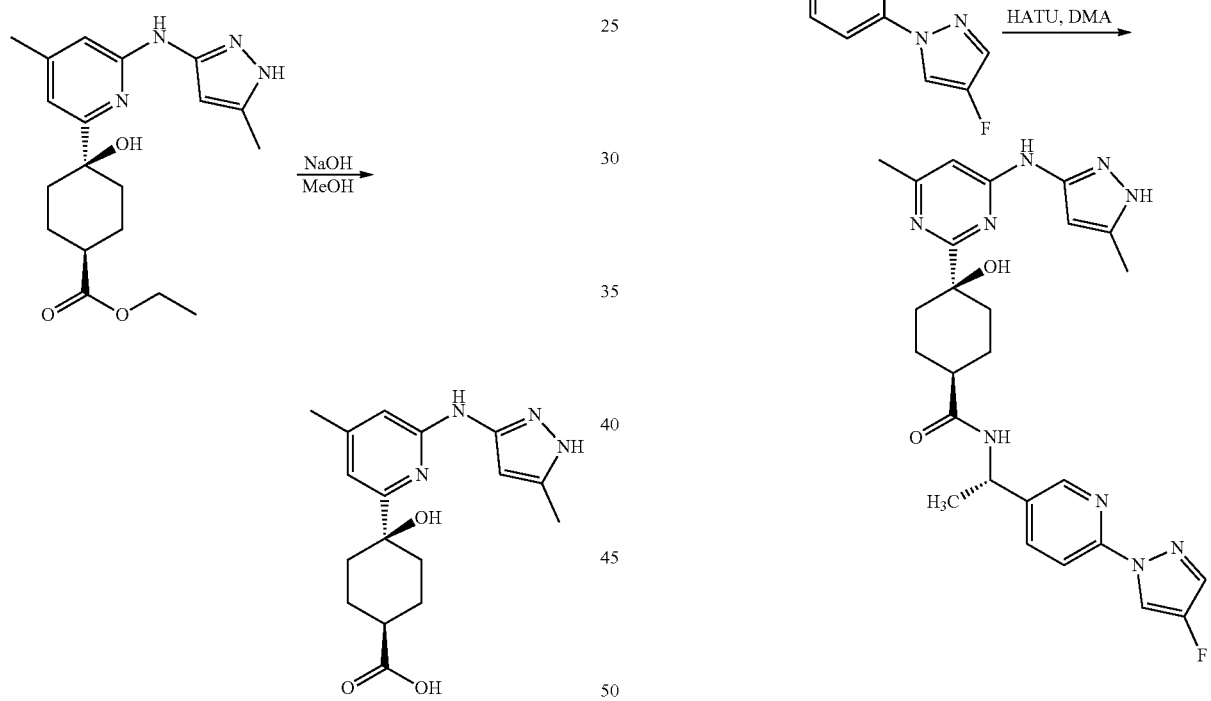

A mixture of (1 S,4S)-4-hydroxy-4-(4-methyl-6-((5-methyl-1H-pyrazol-3-yl)amino)pyridin-2-yl)cyclohexanecarboxylic acid (60 mg, 0.18 mmol), (S)-1-(6-(4-fluoro-1H-pyrazol-1-yl)pyridin-3-yl)ethanamine hydrochloride (44.0 mg, 0.1816 mmol), HATU (69.0 mg, 0.1816 mmol) and DIEA (70.4 mg, 0.545 mmol) in DMA (2 mL) was stirred at 25° C. for 2 h. The solution was concentrated and purified by preparative HPLC to give the title product (40 mg, 43%) as a white solid. MS (ES+) C$_{27}$H$_{31}$FN$_8$O$_2$ requires: 518, found: 519 [M+H]$^+$. $^1$H-NMR (400 MHz, DMSO-d6) δ ppm 11.71 (br. s., 1H), 8.92 (br. s., 1H), 8.69 (d, 1H, J=4.4 Hz), 8.39 (d, 1H, J=2.0 Hz), 8.31 (d, 1H, J=7.6 Hz), 7.95-7.87 (m, 3H), 6.83 (br. s., 1H), 6.79 (s, 1H), 6.09 (br. s., 1H), 5.01-4.98 (m, 1H), 4.89 (s, 1H), 2.50-2.48 (m, 1H), 2.21 (s, 3H), 2.20 (s, 3H), 2.00-1.75 (m, 4H), 1.65-1.50 (m, 4H), 1.41 (d, 3H, J=7.2 Hz).

Example 4. Synthesis of Compounds 121 and 122

Step 1: Synthesis of (1s,4R)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 121), (1R,4S)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 122), and N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohex-3-enecarboxamide

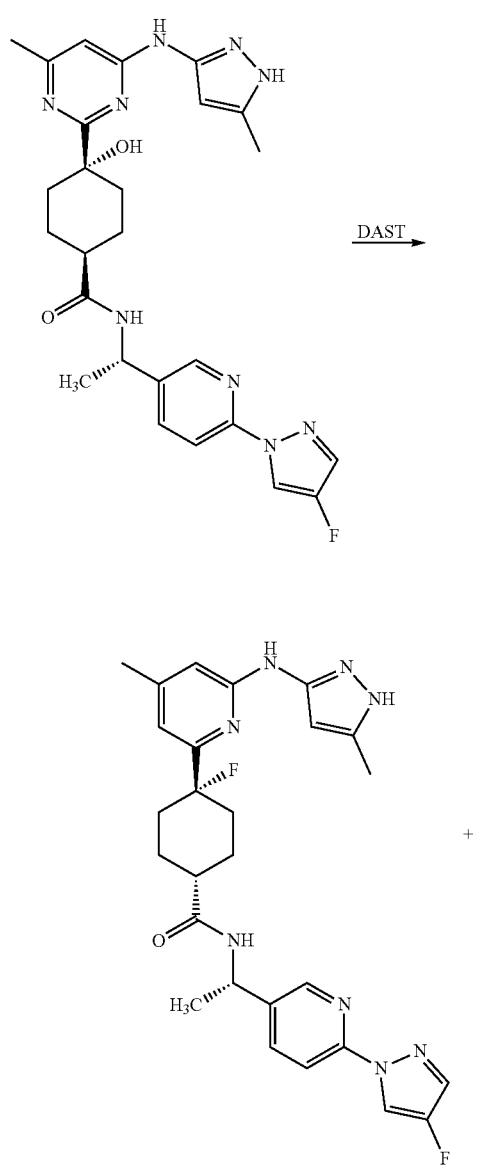

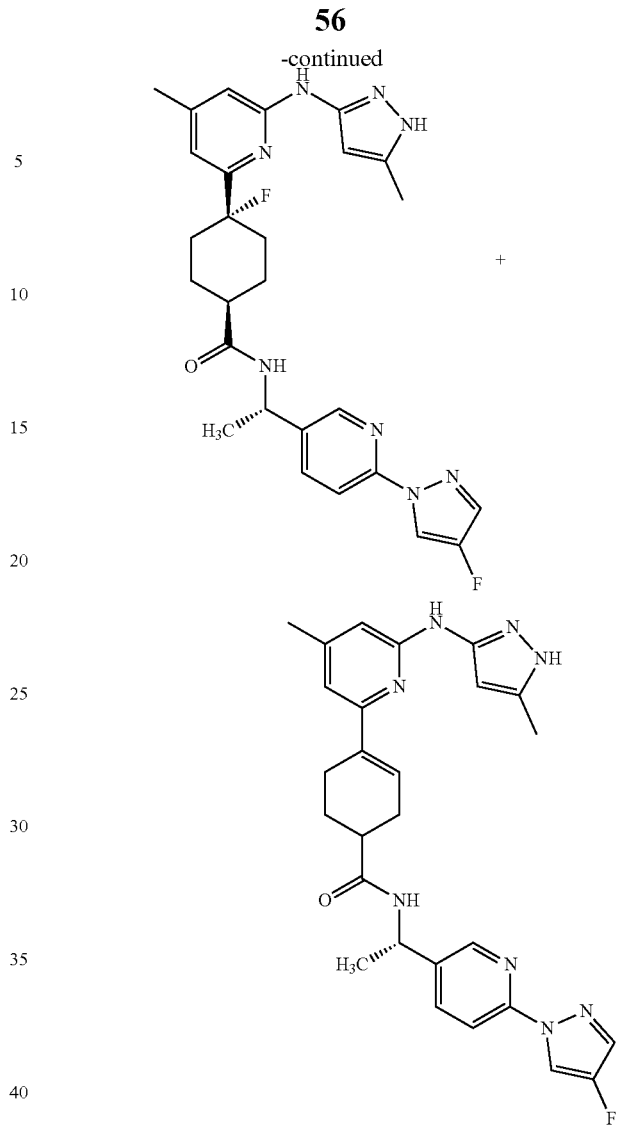

A mixture of (1R,4S)—N—((S)-1-(6-(4-fluoro-1H-pyrazol-1-yl)pyridin-3-yl)ethyl)-4-hydroxy-4-(4-methyl-6-((5-methyl-1H-pyrazol-3-yl)amino)pyridin-2-yl)cyclohexanecarboxamide (120 mg, 0.23 mmol) in DCM (6 mL) was cooled to 0° C. DAST (111 mg, 0.69 mmol) was added to the mixture at 0° C., and the resultant mixture was stirred at 25° C. for 2 h. The mixture was concentrated and purified by preparative HPLC to give the title compounds (1 S,4R)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 121; 6.1 mg, 5.08%) and (1R,4S)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 122; 13.2 mg, 11.0%) as white solids. MS (ES+) $C_{27}H_{30}F_2N_8O$ requires: 520, found: 521 [M+H]$^+$. Also gave N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohex-3-enecarboxamide (50 mg, 43.4%) as a white solid. MS (ES+) $C_{27}H_{29}FN_8O$ requires: 500, found: 501 [M+H]$^+$. (1S,4R)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 121): $^1$H-NMR (400

MHz, DMSO-d6) δ ppm 11.73 (s, 1H), 9.01 (d, 1H, J=2.8 Hz), 8.69 (d, 1H, J=4.4 Hz), 8.41-8.38 (m, 2H), 7.95-7.87 (m, 3H), 6.92 (s, 1H), 6.66 (s, 1H), 6.14 (s, 1H), 5.00 (q, 1H, J=7.2 Hz), 2.50-2.31 (m, 1H), 2.21-2.21 (m, 6H), 2.21-1.74 (m, 8H), 1.41 (d, 3H, J=7.2 Hz). (1R,4S)-4-fluoro-N—((S)-1-(6-(4-fluoro-1H-pyrazol-1-yl)pyridin-3-yl)ethyl)-4-(4-methyl-6-(5-methyl-1H-pyrazol-3-ylamino)pyridin-2-yl)cyclohexanecarboxamide (Compound 122): $^1$H-NMR (400 MHz, DMSO-d6) δ ppm 11.65 (s, 1H), 9.01 (s, 1H), 8.65 (d, 1H, J=4.4 Hz), 8.38-8.33 (m, 2H), 7.92-7.84 (m, 3H), 6.83 (s, 1H), 6.67 (s, 1H), 6.30 (s, 1H), 5.04 (q, 1H, J=7.2 Hz), 2.70-2.50 (m, 3H), 2.20 (s, 3H), 2.15 (s, 3H), 2.21-1.70 (m, 6H), 1.40 (d, 3H, J=7.2 Hz).

Example 5: Synthesis of Compounds 129 and 130

Step 1: Synthesis of 2-chloro-4-methyl-6-(methylthio)pyrimidine

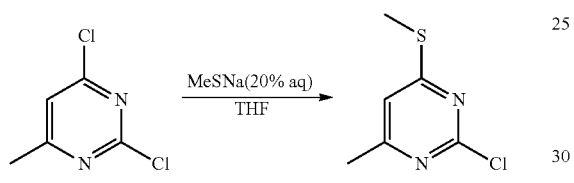

2,4-Dichloro-6-methylpyrimidine (20.0 g, 0.123 mol) was dissolved in THF (200 mL). MeSNa (20% aq, 43 g, 0.129 mol) was added dropwise at −5° C., and the resulting mixture was stirred overnight at room temperature. H$_2$O (100 mL) and EtOAc (100 mL) were added, and the layers were separated. The organic layer was washed with brine (2×), dried over sodium sulfate, and concentrated to afford a yellow solid. The solid was washed by PE (100 mL) to afford target compound (9.1 g). MS (ES+) C$_6$H$_7$ClN$_2$S requires: 174, found: 175 [M+H]$^+$.

Step 2: Synthesis of Methyl 1-methoxy-4-(4-methyl-6-(methylthio)pyrimidin-2-yl)cyclohexane-1-carboxylate

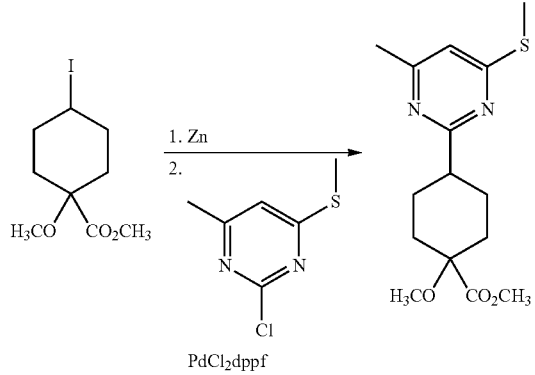

Methyl 4-iodo-1-methoxycyclohexanecarboxylate (1.35 g, 4.53 mmol) was dissolved in dimethylacetamide (10 mL) in a pressure vessel under a stream of N$_2$. Rieke Zinc (5.7 mL of a 50 mg/mL suspension in THF, 4.34 mmol) was added quickly via syringe, and the vessel was capped and stirred at ambient temperature for 15 minutes. The vessel was opened under a stream of N$_2$ and 2-chloro-4-methyl-6-(methylthio)pyrimidine (659 mg, 3.8 mmol) was added followed by PdCl$_2$dppf (138 mg, 0.19 mmol). The vessel was capped and heated to 80° C. for one hour, then cooled to room temperature. The reaction mixture was diluted with EtOAc, filtered through celite, and the filtrate was washed with H$_2$O (3×), brine, dried over sodium sulfate, filtered, and concentrated. The resulting residue was purified by flash-column chromatography on silica gel (gradient elution, 0 to 30% EtOAc-hexanes) to give methyl 1-methoxy-4-(4-methyl-6-(methylthio)pyrimidin-2-yl)cyclohexanecarboxylate (828 mg, 70%) as a colorless oil. The product was determined to be ~3:2 mixture of isomers by integration of the UV peaks in the LC/MS and integration of NMR. MS (ES+) C$_{15}$H$_{22}$N$_2$O$_3$S requires: 310, found: 311 [M+H]$^+$.

Step 3: Synthesis of Methyl 1-methoxy-4-(4-methyl-6-(methylsulfonyl)pyrimidin-2-yl)cyclohexane-1-carboxylate

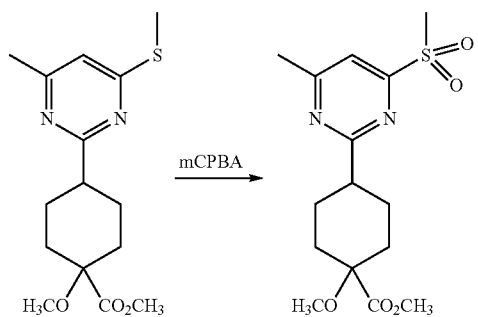

Methyl 1-methoxy-4-(4-methyl-6-(methylthio)pyrimidin-2-yl)cyclohexanecarboxylate (825 mg, 2.66 mmol) was dissolved in DCM (12 mL) followed by the addition of mCPBA (1.10 g, 6.38 mmol) at ambient temperature. The reaction mixture was stirred for 16 h, then an additional portion of mCPBA was added (200 mg). After stirring for an additional 4 h, the reaction mixture was diluted with DCM and then washed with saturated sodium bicarbonate solution. The washed solution was dried over sodium sulfate, filtered, concentrated, and the resulting residue was purified by flash-column chromatography on silica gel (gradient elution, 0 to 60% ethyl acetate-hexane) to afford methyl 1-methoxy-4-(4-methyl-6-(methylsulfonyl)pyrimidin-2-yl)cyclohexanecarboxylate (808 mg, 89%) as a colorless oil. MS (ES+) C$_{15}$H$_{22}$N$_2$O$_5$S requires: 342, found: 343 [M+H]$^+$.

Step 4: Synthesis of Methyl 4-(4-hydroxy-6-methylpyrimidin-2-yl)-1-methoxycyclohexane-1-carboxylate

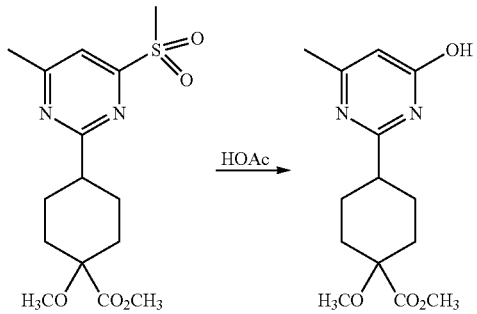 [SMILES: COC(=O)C1(OC)CCC(c2nc(C)cc(S(C)(=O)=O)n2)CC1 ; COC(=O)C1(OC)CCC(c2nc(C)cc(O)n2)CC1 ; "HOAc"]

Methyl 1-methoxy-4-(4-methyl-6-(methylsulfonyl)pyrimidin-2-yl)cyclohexanecarboxylate (600 mg, 1.75 mmol) was dissolved in acetic acid (5 mL) and heated to 80° C. for 1 h. The reaction mixture was then cooled to ambient temperature, concentrated under reduced pressure, triturated with $H_2O$, and filtered. The solids were washed with additional $H_2O$ and then dried under reduced pressure to afford the title compound, methyl 4-(4-hydroxy-6-methylpyrimidin-2-yl)-1-methoxycyclohexanecarboxylate (390 mg, 79%), as a pale yellow solid. MS (ES+) $C_{14}H_{20}N_2O_4$ requires: 280, found: 281 $[M+H]^+$.

Step 5: Synthesis of Methyl 4-(4-chloro-6-methylpyrimidin-2-yl)-1-methoxycyclohexane-1-carboxylate

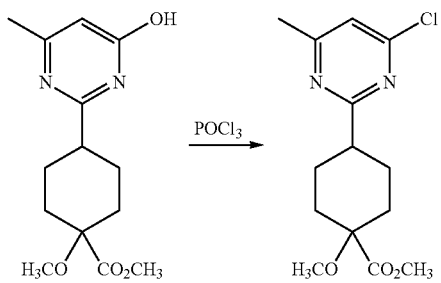

Methyl 4-(4-hydroxy-6-methylpyrimidin-2-yl)-1-methoxycyclohexanecarboxylate (380 mg, 1.36 mmol) was suspended in $POCl_3$ (3.2 mL, 33.9 mmol) and heated to 100° C. for 2 h. The reaction mixture was then cooled to ambient temperature, concentrated, and the residue was treated with crushed ice. The resulting suspension was partitioned with DCM, and the organic layer was extracted with saturated sodium bicarbonate solution and dried over sodium sulfate. The dried solution was filtered, concentrated, and the resulting residue was purified by flash-column chromatography on silica gel (gradient elution, 0 to 30% ethyl acetate-hexanes) to give methyl 4-(4-chloro-6-methylpyrimidin-2-yl)-1-methoxycyclohexanecarboxylate (344 mg, 85%) as a pale orange oil that solidified on standing. MS (ES+) $C_{14}H_{19}ClN_2O_3$ requires: 298, found: 299 $[M+H]^+$.

Step 6: Synthesis of Methyl 1-methoxy-4-(4-methyl-6-((5-methyl-1H-pyrazol-3-yl)amino)pyrimidin-2-yl)cyclohexane-1-carboxylate

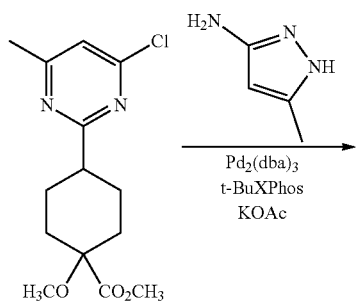

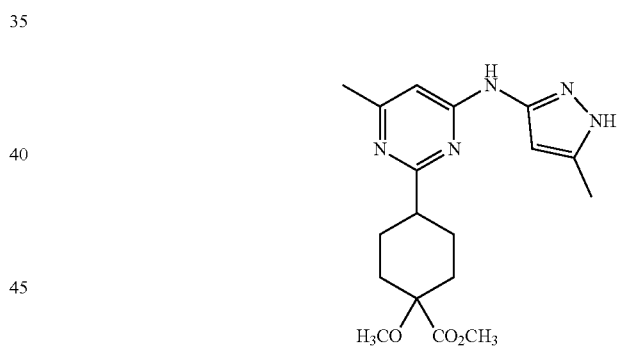

Methyl 4-(4-chloro-6-methylpyrimidin-2-yl)-1-methoxycyclohexanecarboxylate (300 mg, 1.00 mmol), 3-methyl-1-pyrazol-5-amine (146 mg, 1.51 mmol), di-tert-butyl(2',4',6'-triisopropyl-[1,1'-biphenyl]-2-yl)phosphine (85 mg, 0.2 equiv.), $Pd_2(dba)_3$ (92 mg, 0.1 equiv.), and potassium acetate (394 mg, 4.02 mmol) were combined in a vial under nitrogen and 4 mL dioxane was added. The reaction mixture was heated to 100° C. for 1 h, then cooled to ambient temperature. The reaction mixture was diluted with EtOAc, filtered through celite, concentrated, and the resulting residue was purified by flash-column chromatography on silica gel (gradient elution, 0 to 10% methanol-dichloromethane) to give methyl 1-methoxy-4-(4-methyl-6-((5-methyl-1H-pyrazol-3-yl)amino)pyrimidin-2-yl)cyclohexanecarboxylate (192 mg, 53%) as a tan-colored foam. MS (ES+) $C_{18}H_{25}N_5O_3$ requires: 359, found: 360 $[M+H]^+$.

Step 7: Synthesis of (1R,4S)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexanecarboxamide (Compound 129) and (1S,4R)-N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexanecarboxamide (Compound 130)

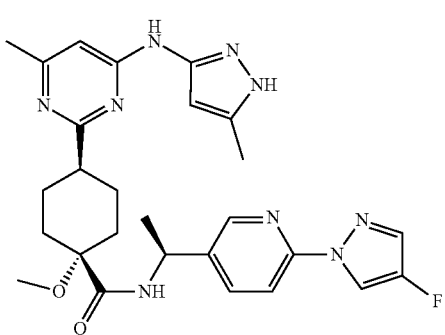

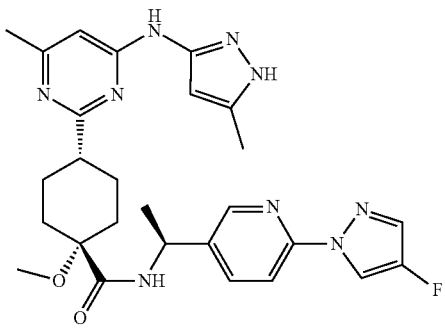

The title compounds were prepared from methyl 1-methoxy-4-(4-methyl-6-((5-methyl-1H-pyrazol-3-yl)amino)pyrimidin-2-yl)cyclohexanecarboxylate (192 mg, 0.53 mmol) using the same two-step procedure (hydrolysis and amide coupling) outlined in Synthetic Protocols 1 and 2, with PyBOP as the amide coupling reagent instead of HATU. The products were initially isolated as a mixture of diastereomers (190 mg), which was then dissolved in 6 mL methanol and purified by SFC (ChiralPak AD-H 21×250 mm, 40% MeOH containing 0.25% DEA in $CO_2$, 2.5 mL injections, 70 mL/min). Peak 1 was concentrated to give (1R,4S)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexanecarboxamide (29 mg, 10%) as a white solid. Peak 2 was concentrated to give (1s,4R)-N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexanecarboxamide (130 mg, 46%) as a white solid.

Example 6. Synthesis of Compound 149

Step 1: Synthesis of Methyl 4-(2-chloro-6-methylpyrimidin-4-yl)-1-methoxycyclohexane-1-carboxylate

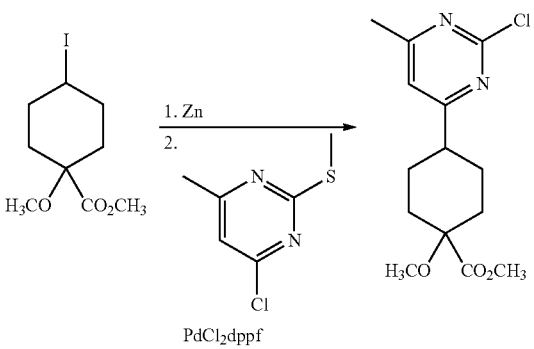

Methyl 4-iodo-1-methoxycyclohexanecarboxylate (3.37 g, 11.3 mmol) was dissolved in dimethylacetamide (38 mL) in a pressure vessel under a stream of $N_2$. Rieke Zinc (17.7 mL of a 50 mg/mL suspension in THF, 13.6 mmol) was added quickly via syringe, and the vessel was capped and stirred at ambient temperature for 15 minutes. The vessel was opened under a stream of $N_2$ and 2,4-dichloro-6-methylpyrimidine (1.84 g, 11.3 mmol) was added followed by $PdCl_2dppf$ (826 mg, 1.13 mmol). The vessel was capped and heated to 80° C. for one hour, then cooled to room temperature. The reaction mixture was diluted with EtOAc, filtered through celite, and the filtrate was washed with $H_2O$ (3×), brine, dried over sodium sulfate, filtered, and concentrated. The resulting residue was purified by flash-column chromatography on silica gel (gradient elution, 0 to 50% EtOAc-hexanes) to give methyl 4-(2-chloro-6-methylpyrimidin-4-yl)-1-methoxycyclohexane-1-carboxylate (74 mg, 2.2%) as a colorless oil. MS (ES+) $C_{14}H_{19}ClN_2O_3$ requires: 298, found: 299 $[M+H]^+$.

Step 2: Synthesis of tert-Butyl 3-((4-(4-methoxy-4-(methoxycarbonyl)cyclohexyl)-6-methylpyrimidin-2-yl)amino)-5-methyl-1H-pyrazole-1-carboxylate

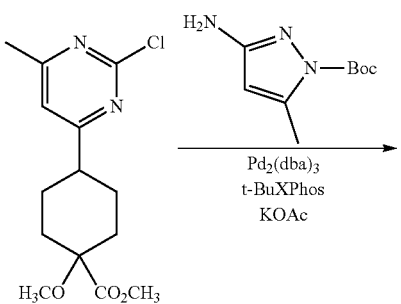

-continued

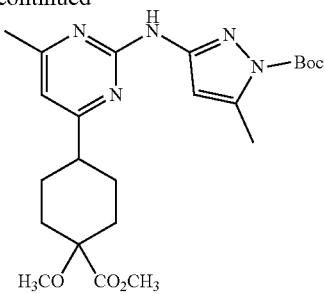

Methyl 4-(2-chloro-6-methylpyrimidin-4-yl)-1-methoxy-cyclohexane-1-carboxylate (70.5 mg, 0.236 mmol), tert-butyl 3-amino-5-methyl-1H-pyrazole-1-carboxylate (69.8 mg, 0.354 mmol), di-tert-butyl(2',4',6'-triisopropyl-[1,1'-biphenyl]-2-yl)phosphine (20.0 mg, 0.2 equiv.), Pd$_2$(dba)$_3$ (21.6 mg, 0.1 equiv.), and potassium acetate (70 mg, 0.71 mmol) were combined in a vial under nitrogen and 0.98 mL dioxane was added. The reaction mixture was heated to 115° C. for 2 h, then cooled to ambient temperature. The reaction mixture was diluted with EtOAc, filtered through celite, concentrated onto silica gel, and the resulting residue was purified by flash-column chromatography on silica gel (gradient elution, 0 to 100% ethyl acetate-hexanes) to give tert-butyl 3-((4-(4-methoxy-4-(methoxycarbonyl)cyclohexyl)-6-methylpyrimidin-2-yl)amino)-5-methyl-1H-pyrazole-1-carboxylate (48 mg, 44%) as a yellow oil. MS (ES+) C$_{23}$H$_{33}$N$_5$O$_5$ requires: 459, found: 460 [M+H]$^+$.

Step 3: Synthesis of 1-Methoxy-4-(6-methyl-2-((5-methyl-1H-pyrazol-3-yl)amino)pyrimidin-4-yl)cyclohexane-1-carboxylic acid Lithium hydroxide monohydrate (13 mg, 0.31 mmol) was added to a solution of tert-butyl 3-((4-(4-methoxy-4-(methoxycarbonyl)cyclohexyl)-6-methylpyrimidin-2-yl)amino)-5-methyl-1H-pyrazole-1-carboxylate (47.7 mg, 0.104 mmol) in THF/MeOH/H$_2$O (17:1:1, 1.8 mL). The reaction mixture was heated to 60° C. and stirred for 16 h. The reaction mixture was then cooled to ambient temperature and concentrated to give crude 1-methoxy-4-(6-methyl-2-((5-methyl-1H-pyrazol-3-yl)amino)pyrimidin-4-yl)cyclohexane-1-carboxylic acid (57 mg, crude) which was used in the subsequent amide coupling without any further purification. MS (ES+) C$_{17}$H$_{23}$N$_5$O$_3$ requires: 345, found: 346 [M+H]$^+$.

Step 4: Synthesis of (1s,4R)-N—((S)-1-(6-(4-fluoro-1H-pyrazol-1-yl)pyridin-3-yl)ethyl)-1-methoxy-4-(6-methyl-2-((5-methyl-1H-pyrazol-3-yl)amino)pyrimidin-4-yl)cyclohexane-1-carboxamide (Compound 149)

The title compound was prepared from 1-methoxy-4-(6-methyl-2-((5-methyl-1H-pyrazol-3-yl)amino)pyrimidin-4-yl)cyclohexane-1-carboxylic acid (57 mg, 0.104 mmol) using the same procedure (amide coupling) outlined in Synthetic Protocols 1 and 2, with PyBOP as the amide coupling reagent instead of HATU. The products were initially isolated as a mixture of diastereomers (36 mg), which was then dissolved in 6 mL methanol-DCM (1:1) and purified by SFC (ChiralPak IC-H 21×250 mm, 40% MeOH containing 0.25% DEA in CO$_2$, 1.0 mL injections, 70 mL/min). Peak 1 was an undesired isomer, and Peak 2 was concentrated to give (1 s,4R)-N—((S)-1-(6-(4-fluoro-1H-pyrazol-1-yl)pyridin-3-yl)ethyl)-1-methoxy-4-(6-methyl-2-((5-methyl-1H-pyrazol-3-yl)amino)pyrimidin-4-yl)cyclohexane-1-carboxamide (13.4 mg, 24%) as a white solid.

Synthesis of Intermediates

Example 7. Synthesis of Ketone and Boronate Intermediates

A. Methyl 1-methoxy-4-oxocyclohexane-1-carboxylate

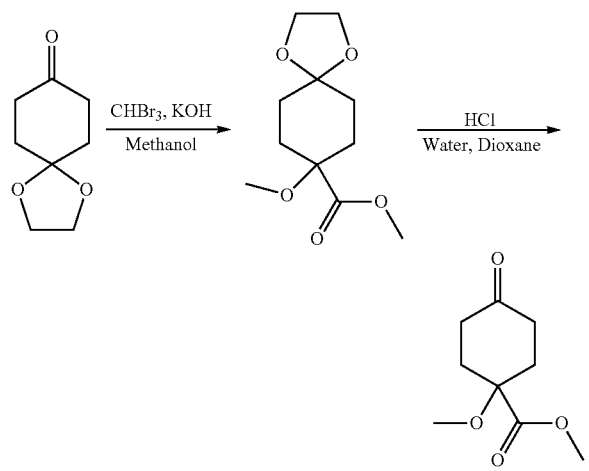

The title compound was prepared as described in WO 2014/130810 A1 page 86.

B. Ethyl 1-ethoxy-4-oxocyclohexane-1-carboxylate

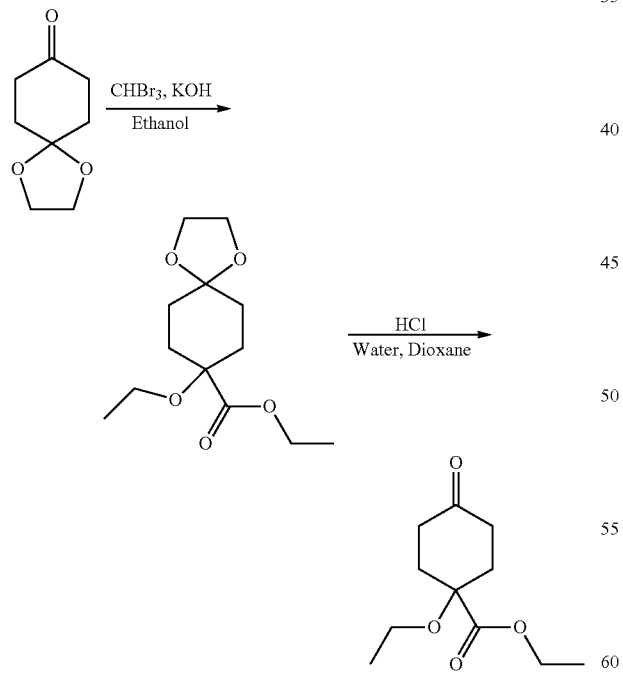

Step 1: Synthesis of ethyl 8-ethoxy-1,4-dioxaspiro[4.5]decane-8-carboxylate

A solution of 1,4-dioxaspiro[4.5]decan-8-one (20.0 g, 128 mmol) in CHBr$_3$ (3234 g, 1280 mmol) was cooled to 0° C. and potassium hydroxide (57.5 g, 1024 mmol) in EtOH (300 mL) was added dropwise over 2.5 hrs. After stirring the mixture for 23 h, the mixture was concentrated, and the residue was partitioned between EtOAc and H$_2$O. The organic layer was washed with brine, dried over Na$_2$SO$_4$, filtered, and concentrated under reduced pressure to give crude product, which was purified by flash column chromatography on silica gel (gradient elution, PE:EA=15:1 to 10:1) to obtain the title compound (18.0 g).

Step 2: Synthesis of ethyl 1-ethoxy-4-oxocyclohexane-1-carboxylate

To a solution of ethyl 8-ethoxy-1,4-dioxaspiro[4.5]decane-8-carboxylate (10 g, 43 mmol) in 1,4-dioxane (250 mL) was added aqueous HCl (6 M, 92.5 mL), and the mixture was stirred for 23 h at ambient temperature. The mixture was then diluted with H$_2$O and extracted with EtOAc. The organic layers were washed with brine, dried over Na$_2$SO$_4$, filtered, and concentrated under reduced pressure to give a crude residue, which was purified by flash column chromatography on silica gel (PE:EA=15:1) to obtain the product (8.0 g). $^1$H NMR (400 MHz, DMSO) δ 4.20-4.13 (m, 2H), 3.43 (q, J=6.9 Hz, 1H), 2.48-2.39 (m, 1H), 2.24-2.12 (m, 2H), 2.10-2.01 (m, 1H), 1.22 (t, J=7.1 Hz, 2H), 1.17 (t, J=7.0 Hz, 2H).

C. Ethyl 6,6-dimethyl-4-(4,4,5,5-tetramethyl-1,3,2-dioxaborolan-2-yl)cyclohex-3-ene-1-carboxylate

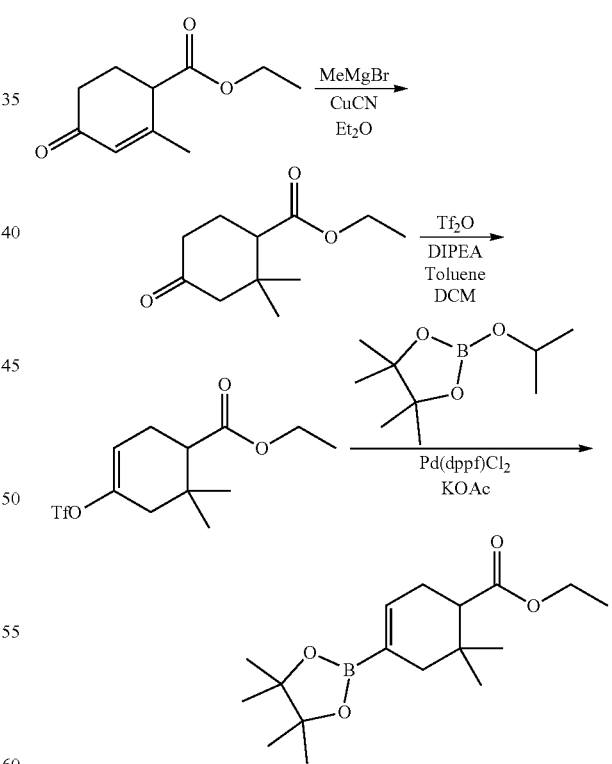

Step 1: Synthesis of ethyl 2,2-dimethyl-4-oxocyclohexane-1-carboxylate

A solution of methylmagnesium bromide (3M, 109.8 mL, 329.4 mmol) was added dropwise to a suspension of CuCN (14.75 g, 164.7 mmol) in diethyl ether (50 mL) at 0° C. The mixture was stirred for 30 min at 0° C. and then cooled to −78° C. The solution of ethyl 2-methyl-4-oxocyclohex-2-ene-1-carboxylate (10 g, 54.9 mmol) in diethyl ether (10 mL) was then added dropwise. The mixture was stirred between −40° C. to −20° C. for 2 h, then was warmed to ambient temperature for 16 h. The reaction mixture was carefully added to a saturated solution of ammonium chloride. The aqueous layer was extracted twice with diethyl ether, and the organic layers were combined. The combined organic layer was washed with brine, dried over sodium sulfate, filtered and concentrated. The residue was purified by flash column chromatography on silica gel (PE:EA=10:1) to give ethyl 2,2-dimethyl-4-oxocyclohexane-1-carboxylate (1.16 g).

Step 2: Synthesis of ethyl 6,6-dimethyl-4-(((trifluoromethyl)sulfonyl)oxy)cyclohex-3-ene-1-carboxylate Ethyl 2,2-dimethyl-4-oxocyclohexane-1-carboxylate (1.16 g, 5.85 mmol) and DIPEA (3.03 g, 23.4 mmol) were dissolved in dry toluene (2 mL) and heated at 45° C. for 10 minutes. Trifluoromethanesulfonic anhydride (6.61 g, 23.4 mmol) in DCM (20 mL) was added dropwise over 10 min and the mixture was heated at 45° C. for 2 h. The mixture was allowed to cool to room temperature, concentrated, diluted with water (60 mL) and extracted with DCM (2×40 mL). The organic layer was washed with saturated sodium bicarbonate solution (20 mL) and brine (20 mL), dried over sodium sulfate, filtered, and concentrated. The crude product was purified by flash column chromatography on silica gel (gradient elution, 0 to 100% ethyl acetate-petroleum ether) to afford ethyl 6,6-dimethyl-4-(((trifluoromethyl)sulfonyl)oxy)cyclohex-3-ene-1-carboxylate (1 g).

Step 3: Synthesis of ethyl 6,6-dimethyl-4-(4,4,5,5-tetramethyl-1,3,2-dioxaborolan-2-yl)cyclohex-3-ene-1-carboxylate Ethyl 6,6-dimethyl-4-(4,4,5,5-tetramethyl-1,3,2-dioxaborolan-2-yl)cyclohex-3-ene-1-carboxylate (1 g, 3.03 mmol), 4,4,5,5-tetramethyl-2-(4,4,5,5-tetramethyl-1,3,2-dioxaborolan-2-yl)-1,3,2-dioxaborolane (1.15 g, 4.54 mmol), Pd(dppf)Cl$_2$ (73.5 mg, 0.09 mmol) and potassium acetate (891 mg, 9.08 mmol) were suspended in 1,4-dioxane (20 mL). The reaction mixture was flushed with nitrogen, then heated to 100° C. for 2 h. The mixture was cooled to room temperature, filtered, and concentrated, and the resulting brown oil was purified by flash column chromatography on silica gel (gradient elution, 0 to 100% ethyl acetate-petroleum ether) to afford ethyl 6,6-dimethyl-4-(4,4,5,5-tetramethyl-1,3,2-dioxaborolan-2-yl)cyclohex-3-ene-1-carboxylate (618 mg).

D. Ethyl 6-methyl-4-(4,4,5,5-tetramethyl-1,3,2-dioxaborolan-2-yl)cyclohex-3-ene-1-carboxylate

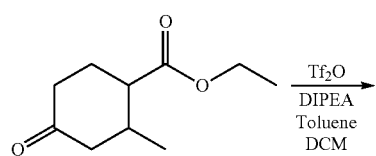

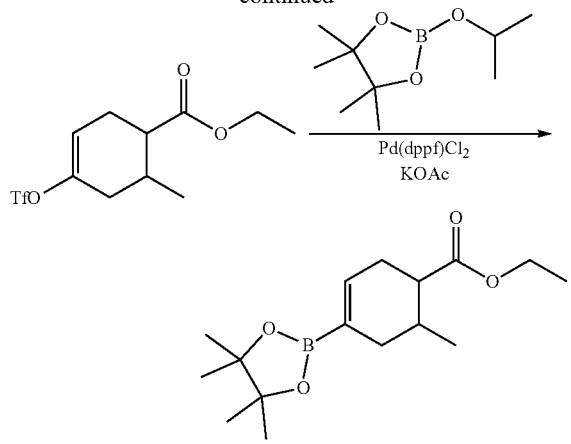

Ethyl 6-methyl-4-(4,4,5,5-tetramethyl-1,3,2-dioxaborolan-2-yl)cyclohex-3-ene-1-carboxylate was prepared using the same synthetic protocol as described above using ethyl 2-methyl-4-oxocyclohexane-1-carboxylate as the starting material.

E. Methyl 2-methyl-5-oxotetrahydro-2H-pyran-2-carboxylate

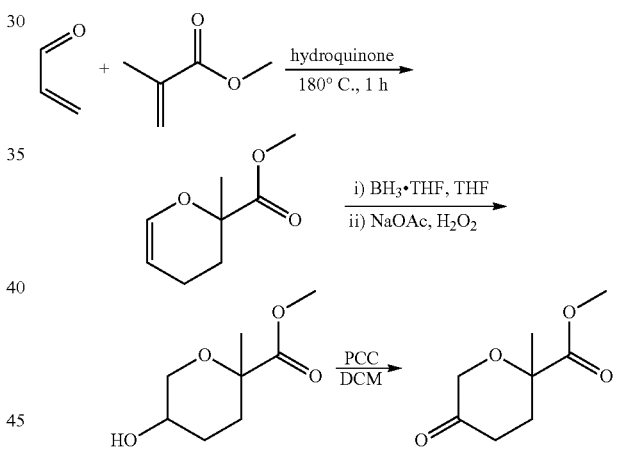

Step 1: Synthesis of methyl 2-methyl-3,4-dihydro-2H-pyran-2-carboxylate

A mixture of acrylaldehyde (120 g, 2.14 mol), methyl methacrylate (200 g, 2.00 mol) and hydroquinone (2.2 g, 20 mmol) were heated in a sealed steel vessel at 180° C. for one h. The mixture was then cooled to ambient temperature and concentrated. The residue was purified by silica gel column chromatography (gradient elution, petroleum ether:ethyl acetate=100:1 to 80:1) to give methyl 2-methyl-3,4-dihydro-2H-pyran-2-carboxylate (70 g, 22% yield) as a pale yellow oil. $^1$H-NMR (400 MHz, CDCl3): δ 6.38 (d, J=6.4 Hz, 1H), 4.73-4.70 (m, 1H), 3.76 (s, 3H), 2.25-2.22 (m, 1H), 1.99-1.96 (m, 2H), 1.79-1.77 (m, 1H), 1.49 (s, 3H).

Step 2: Synthesis of methyl 5-hydroxy-2-methyltetrahydro-2H-pyran-2-carboxylate

To a solution of methyl 2-methyl-3,4-dihydro-2H-pyran-2-carboxylate (20.0 g, 128 mmol) in anhydrous tetrahydrofuran (200 mL) was added borane (67 mL, 1 M in tetrahydrofuran) dropwise at −5° C. The reaction mixture was stirred at 0° C. for 3 hours. This reaction was monitored by TLC. The mixture was quenched by a solution of sodium acetate (10.5 g, 128 mmol) in water (15 mL). Then the mixture was treated with 30% hydrogen peroxide solution (23.6 g, 208.2 mmol) slowly at 0° C. and stirred at 30° C. for 3 h. The mixture was then partitioned between saturated sodium sulfite solution and tetrahydrofuran. The aqueous layer was further extracted with tetrahydrofuran (2×). The combined organic layers were washed with saturated brine, dried over sodium sulfate and concentrated in vacuo. The residue was purified by a silica gel column chromatography (gradient elution, petroleum ether:ethyl acetate=10:1 to 1:1) to give crude methyl 5-hydroxy-2-methyltetrahydro-2H-pyran-2-carboxylate (18 g, crude) as a pale yellow oil, which used directly for next step.

Step 3: Synthesis of methyl 2-methyl-5-oxotetrahydro-2H-pyran-2-carboxylate

To a solution of methyl 5-hydroxy-2-methyltetrahydro-2H-pyran-2-carboxylate (18.0 g, 103 mmol) in anhydrous dichloromethane (200 mL) was added PCC (45.0 g, 209 mmol) in portions. The reaction mixture was stirred at ambient temperature until TLC indicated the reaction was completed. Petroleum ether (500 mL) was then added and the mixture was filtered. The filter cake was washed with petroleum ether (100 mL), and the filtrate was concentrated under vacuum to give methyl 2-methyl-5-oxotetrahydro-2H-pyran-2-carboxylate (15 g, 84% yield) as a pale yellow oil. $^1$H-NMR (400 MHz, CDCl$_3$): δ 4.25 (d, J=17.6 Hz, 1H), 4.07 (d, J=17.6 Hz, 1H), 3.81 (s, 3H), 2.52-2.44 (m, 3H), 2.11-2.04 (m, 1H), 1.53 (s, 3H).

Example 8. Synthesis of Iodide Intermediates

A. Methyl 1-methoxy-4-iodocyclohexane-1-carboxylate

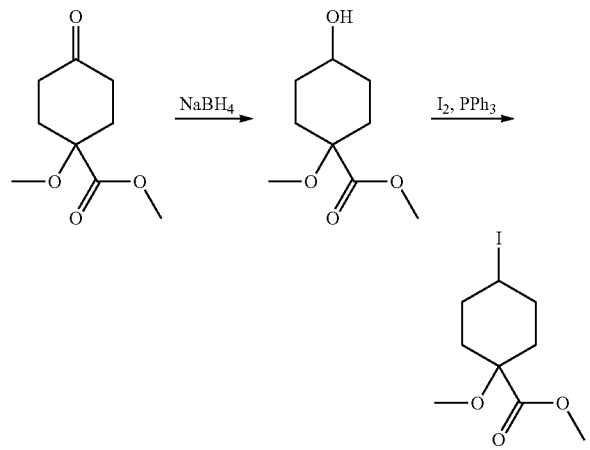

Step 1: Synthesis of methyl 1-methoxy-4-hydroxycyclohexane-1-carboxylate

Methyl 1-methoxy-4-oxocyclohexanecarboxylate (4.00 g, 21.5 mmol) was dissolved in methanol (100 mL) and the solution was cooled to 0° C. Sodium borohydride (2.03 g, 53.7 mmol) was added in portions over 20 min. The reaction mixture was stirred for 30 min, then was quenched by addition of aqueous saturated NH$_4$Cl solution. The quenched reaction mixture was evaporated to remove the MeOH, then the aqueous suspension was extracted with DCM (3×). The combined organic layers were dried over sodium sulfate, filtered, and concentrated to yield a residue that was purified by flash-column chromatography on silica gel (gradient elution, 5% to 100% ethyl acetate-hexanes) to afford methyl 1-methoxy-4-hydroxycyclohexane-1-carboxylate (2.00 g, 49.5%) as a colorless oil. MS (ES+) C$_9$H$_{16}$O$_4$ requires: 188, found: 211 [M+Na]$^+$.

Step 2: Synthesis of methyl 1-methoxy-4-iodocyclohexane-1-carboxylate

Methyl 1-methoxy-4-hydroxycyclohexane-1-carboxylate (2.00 g, 10.6 mmol) was dissolved in THF (20 mL) and imidazole (723 mg, 10.6 mmol) and triphenylphosphine (3.34 g, 12.8 mmol) were added. The mixture was cooled to 0° C., and then a solution of iodine (3.24 g, 12.8 mmol) in THF (10 mL) was added dropwise over 15 min. The reaction mixture was allowed to warm to ambient temperature and was then stirred for 2 days, after which it was poured over saturated sodium thiosulfate solution and extracted with EtOAc. The organic layer was dried over sodium sulfate, filtered, concentrated, and the residue was triturated with hexane (40 mL, stir for 20 min). The mixture was filtered, and the filtrate was evaporated to provide a residue that was purified by flash-column chromatography on silica gel (gradient elution, 0 to 30% ethyl acetate-hexanes) to give the title compound (2.37 g, 75%) as a pale yellow oil. MS (ES+) C$_9$H$_{15}$IO$_3$ requires: 298, found: 299 [M+H]$^+$.

B. Ethyl 1-ethoxy-4-iodocyclohexane-1-carboxylate

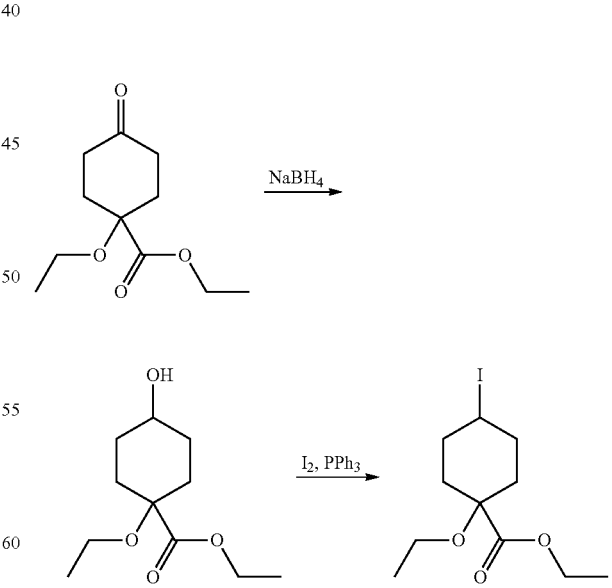

The title compound was prepared as described above using ethyl 1-ethoxy-4-oxocyclohexane-1-carboxylate as a starting material. C$_{11}$H$_{19}$IO$_3$ requires: 326, found: 327 [M+H]$^+$.

Example 9. Synthesis of Amine Intermediates

A. (S)-1-(6-(4-fluoro-1H-pyrazol-1-yl)pyridin-3-yl)ethan-1-amine

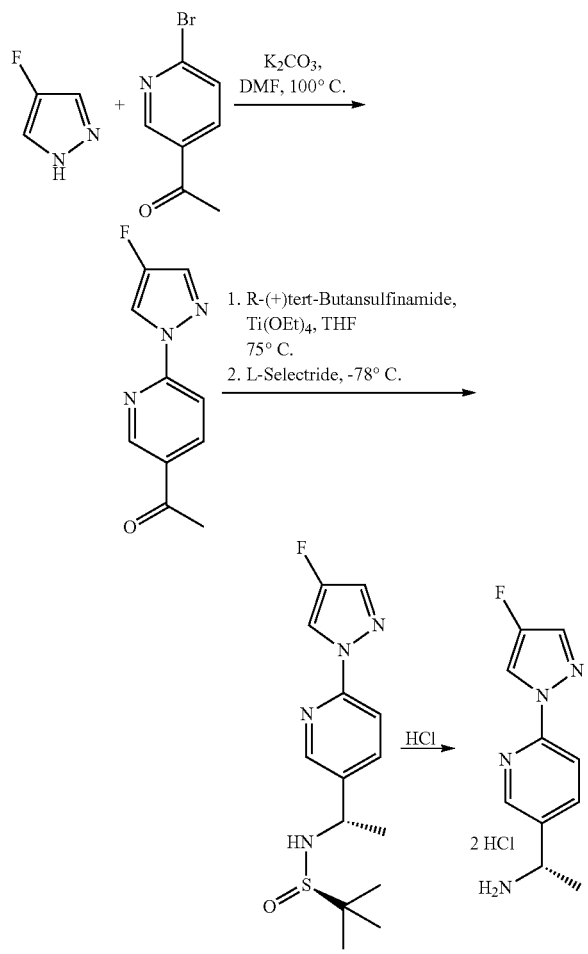

Step 1: Synthesis of 1-(6-(4-fluoro-1H-pyrazol-1-yl)pyridin-3-yl)ethan-1-one 4-Fluoro-1H-pyrazole (4.73 g, 55 mmol) and potassium carbonate (17.27 g, 125 mmol) were combined and stirred in N,N-dimethylformamide (41.7 mL) for 10 minutes in an open sealed tube before addition of 2-bromo-5-acetylpyridine (10 g, 50 mmol). The reaction tube was sealed and stirred for 20 hours at 100° C. The reaction mixture was then cooled to room temperature and poured into water (~700 mL). The mixture was sonicated and stirred for 20 minutes, after which a beige solid was isolated by filtration, washed with small amounts of water, and dried to yield 1-(6-(4-fluoro-1H-pyrazol-1-yl)pyridin-3-yl)ethan-1-one (9.81 g, 96% yield). MS: M+1=206.0.

Step 2: Synthesis of (R)-N—((S)-1-(6-(4-fluoro-1H-pyrazol-1-yl)pyridin-3-yl)ethyl)-2-methylpropane-2-sulfinamide To a stirred room temperature solution of 1-(6-(4-fluoro-1H-pyrazol-1-yl)pyridin-3-yl)ethan-1-one (9.806 g, 47.8 mmol) in THF (96 mL) was added (R)-(+)-t-Butylsulfinamide (5.79 g, 47.8 mmol) followed by titanium (IV) ethoxide (21.8 g, 96 mmol). The solution was stirred at 75° C. on an oil bath for 15 hours. The reaction solution was cooled to room temperature and then to −78° C. (external temperature) before the next step. To the −78° C. solution was added dropwise over nearly 55 minutes L-Selectride (143 mL of 1N in THF, 143 mmol). During addition, some bubbling was observed. The reaction was then stirred after the addition was completed for 15 minutes at −78° C. before warming to room temperature. LC-MS of sample taken during removal from cold bath showed reaction was completed. The reaction was cooled to −50° C. and quenched slowly with methanol (~10 mL), then poured into water (600 mL) and stirred. An off-white precipitate was removed by filtration, with ethyl acetate used for washes. The filtrate was diluted with ethyl acetate (800 mL), the layers were separated, and the organic layer was dried over sodium sulfate, filtered, and concentrated down. The crude was purified by silica gel chromatography to yield (R)-N—((S)-1-(6-(4-fluoro-1H-pyrazol-1-yl)pyridin-3-yl)ethyl)-2-methylpropane-2-sulfinamide (10.5 g, 99% purity, 70.3% yield) as a light yellow solid. MS: M+1=311.1.

Step 3: Synthesis of (S)-1-(6-(4-fluoro-1H-pyrazol-1-yl)pyridin-3-yl)ethan-1-amine A solution of (R)-N—((S)-1-(6-(4-fluoro-1H-pyrazol-1-yl)pyridin-3-yl)ethyl)-2-methylpropane-2-sulfinamide (10.53 g, 33.9 mmol)) in methanol (79 mmol) and 4N HCl/dioxane (85 mL, 339 mmol) was stirred for 2.5 hours, at which point LC-MS showed reaction was complete. The reaction solution was poured into diethyl ether (300 mL) and a sticky solid was formed. The mixture was treated with ethyl acetate (200 mL) and sonicated. The solvents were decanted, and the sticky solid was treated with more ethyl acetate (~200 mL), sonicated and stirred. The bulk of the sticky solid was converted to a suspension. A light yellow solid was isolated by filtration, washed with smaller amounts of ethyl acetate, and dried to yield (S)-1-(6-(4-fluoro-1H-pyrazol-1-yl)pyridin-3-yl)ethan-1-amine (7.419 g, 78% yield). LC-MS confirmed desired product in high purity. MS: M+1=207.1.

B. (S)-1-(5-(4-fluoro-1H-pyrazol-1-yl)pyrazin-2-yl)ethan-1-amine

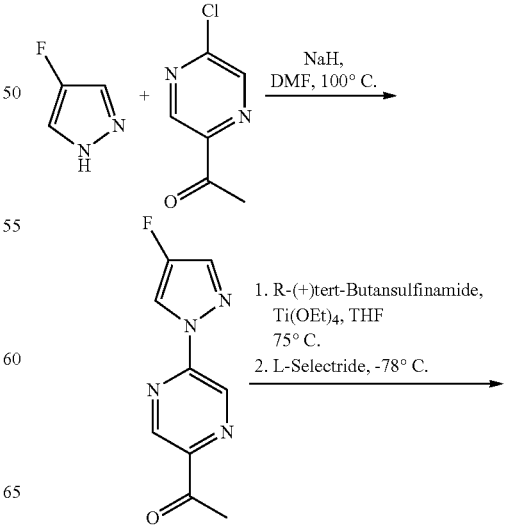

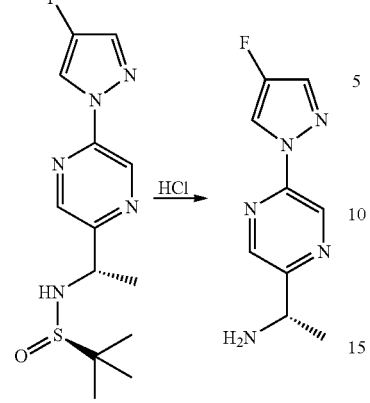

Step 1: Synthesis of 1-(5-(4-fluoro-1H-pyrazol-1-yl)pyrazin-2-yl)ethan-1-one Sodium hydride (60 wt %, 276 mg, 6.90 mmol) was added to a mixture of 1-(5-chloropyrazin-2-yl)ethanone (800 mg, 5.11 mmol) and 4-fluoro-1H-pyrazole (484 mg, 5.62 mmol) in N,N-dimethylformamide (6.0 mL) at ambient temperature for 10 minutes. The reaction mixture was then poured into water (70 mL) and sonicated and stirred for 20 minutes. A dark red solid was isolated by filtration, washed with small amounts of water, and dried to 1-(5-(4-fluoro-1H-pyrazol-1-yl)pyrazin-2-yl)ethan-1-one (919 mg, 95% yield). MS: M+1=207.

Step 2: Synthesis of (R)-N—((S)-1-(5-(4-fluoro-1H-pyrazol-1-yl)pyrazin-2-yl)ethyl)-2-methylpropane-2-sulfinamide To a stirred room temperature solution of 1-(5-(4-fluoro-1H-pyrazol-1-yl)pyrazin-2-yl)ethan-1-one (4.67 g, 22.7 mmol) in THF (45 mL) was added (R)-(+)-t-butylsulfinamide (2.75 g, 22.7 mmol) followed by titanium (IV) ethoxide (10.3 g, 45.3 mmol). The solution was stirred at 75° C. on an oil bath for 20 hours. The reaction solution was cooled to room temperature and then to −78° C. before the next step. To the −78° C. solution was added dropwise over 50 minutes L-Selectride (50.1 mL of 1 N in THF, 50.1 mmol). During addition, some bubbling was observed. After the addition was completed, the reaction was then stirred for 15 minutes before warming to room temperature. LC-MS of sample taken during removal from cold bath showed reaction was completed. The reaction was cooled to −60° C. and quenched slowly with methanol (1 mL), then poured into water (100 mL) and stirred. The mixture was filtered and the solids were washed further with ethyl acetate. The filtrate was diluted with ethyl acetate, and the organic layer was dried over sodium sulfate, filtered, concentrated, and the resulting residue was purified by flash-column chromatography (gradient elution, 0 to 100% ethyl acetate-dichloromethane) to give (R)-N—((S)-1-(5-(4-fluoro-1H-pyrazol-1-yl)pyrazin-2-yl)ethyl)-2-methylpropane-2-sulfinamide (1.04 g, 14%) as a brown solid. MS: M+1=312. $^1$H NMR (400 MHz, DMSO-d6) δ 9.12 (d, J=1.4 Hz, 1H), 8.73 (d, J=4.5 Hz, 1H), 8.59 (d, J=1.4 Hz, 1H), 8.03 (d, J=4.1 Hz, 1H), 5.69 (d, J=5.7 Hz, 1H), 4.62 (p, J=6.8 Hz, 3H), 1.57 (d, J=6.9 Hz, 3H), 1.12 (s, 9H).

Step 3: Synthesis of (S)-1-(5-(4-fluoro-1H-pyrazol-1-yl)pyrazin-2-yl)ethan-1-amine A solution of (R)-N—((S)-1-(5-(4-fluoro-1H-pyrazol-1-yl)pyrazin-2-yl)ethyl)-2-methylpropane-2-sulfinamide (1.04 g, 3.34 mmol) in methanol (7.8 mL) and 4N HCl/dioxane (8.34 mL, 33.4 mmol) was stirred for 1.5 h at ambient temperature. The reaction mixture was poured into diethyl ether (100 mL), and a light beige solid was isolated by filtration to afford (S)-1-(5-(4-fluoro-1H-pyrazol-1-yl)pyrazin-2-yl)ethan-1-amine (689 mg, 85% yield). MS: M+1=208.

C. (5-(4-fluoro-1H-pyrazol-1-yl)pyrazin-2-yl)methanamine

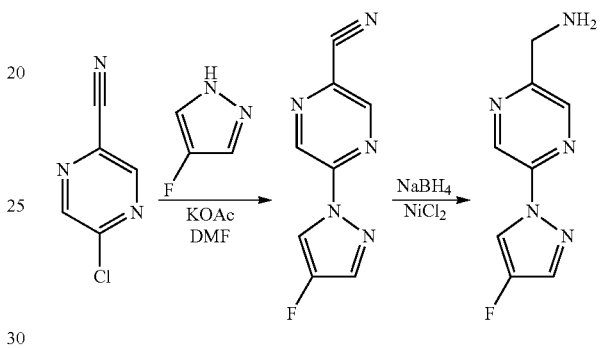

Step 1: Synthesis of 5-(4-fluoro-1H-pyrazol-1-yl)pyrazine-2-carbonitrile

To a solution of 5-chloropyrazine-2-carbonitrile (280 mg, 2.0 mmol) in DMF was added 4-fluoro-1H-pyrazole (170 mg, 2.0 mmol) and potassium acetate (395 mg, 4.0 mmol). The mixture was stirred at 100° C. for 4 hours, then cooled to 20° C., poured into brine (25 mL), and extracted with ethyl acetate. The organic layer was dried over sodium sulfate, concentrated, and purified by column chromatography (hexane:ethyl acetate=5:1) to give 5-(4-fluoro-1H-pyrazol-1-yl)pyrazine-2-carbonitrile (310 mg, 82%). The structure was confirmed by LC-MS.

Step 2: Synthesis of (5-(4-fluoro-1H-pyrazol-1-yl)pyrazin-2-yl)methanamine

A mixture of 5-(4-fluoro-1H-pyrazol-1-yl)pyrazine-2-carbonitrile (190 mg, 1.0 mmol) and NiCl$_2$ (12 mg, 0.1 mmol) in MeOH (5 mL) was added NaBH$_4$ (380 mg, 10 mmol) at 0° C. The mixture was stirred at 0° C. for 2 hours, quenched with aqueous NH$_4$Cl, and purified by HPLC to give (5-(4-fluoro-1H-pyrazol-1-yl)pyrazin-2-yl)methanamine (160 mg, Yield 82%). The structure was confirmed by LC-MS.

D. (6-(3,5-dimethyl-1H-pyrazol-1-yl)pyridin-3-yl)methanamine

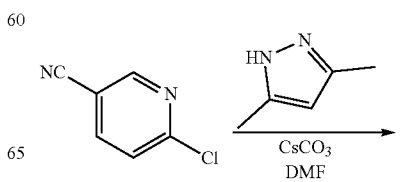

-continued

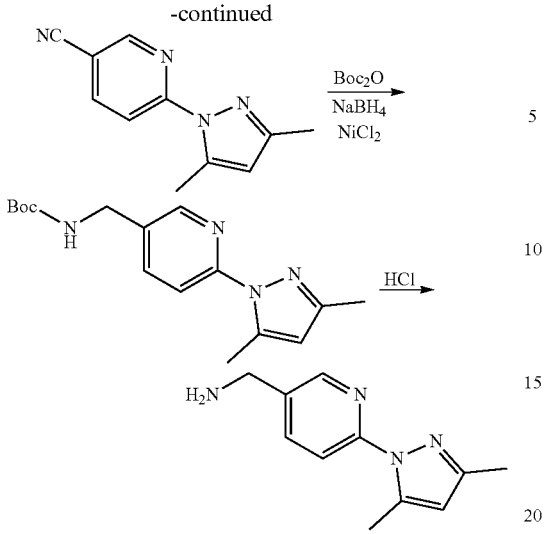

Step 1: Synthesis of 6-(3,5-dimethyl-1H-pyrazol-1-yl)nicotinonitrile

To a solution of 6-chloronicotinonitrile (300 mg, 2.2 mmol) in DMF (10 mL) was added 3,5-dimethyl-1H-pyrazole (210 mg, 2.2 mmol) and $Cs_2CO_3$ (1.4 g, 4.4 mmol), and the mixture was stirred at 90° C. for 16 h. The mixture was then diluted with $H_2O$ (25 mL) and filtered. The solids were washed with water and dried under vacuum to give 6-(3,5-Dimethyl-1H-pyrazol-1-yl)nicotinonitrile (320 mg, 74.6%).

Step 2: Synthesis of tert-Butyl ((6-(3,5-dimethyl-1H-pyrazol-1-yl)pyridin-3-yl)methyl)carbamate To 6-(3,5-dimethyl-1H-pyrazol-1-yl)nicotinonitrile (300 mg, 1.5 mmol) in MeOH (10 mL) was added $NiCl_2$ (19 mg, 0.15 mmol), $(Boc)_2O$ (654 mg, 3.0 mmol), and $NaBH_4$ (142 mg, 3.8 mmol), and the mixture was stirred at ambient temperature for 3 h. Saturated aqueous ammonium chloride solution was added, and MeOH was removed under vacuum. The aqueous suspension was partitioned with ethyl acetate, and the organic layer was washed with saturated sodium bicarbonate solution (2×50 mL), dried with anhydrous sodium sulfate, filtered, and concentrated under vacuum to give 450 mg target compound which was used in the next step without further purification.

Step 3: Synthesis of (6-(3,5-dimethyl-1H-pyrazol-1-yl)pyridin-3-yl)methanamine A solution of HCl in dioxane (4.0 M, 10 mL) was added to compound tert-butyl ((6-(3,5-dimethyl-1H-pyrazol-1-yl)pyridin-3-yl)methyl)carbamate (450 mg), and the mixture was stirred for 2 h. The mixture was then concentrated under reduced pressure to give the title compound (350 mg) as a light brown solid that was carried forward without further purification. $^1$H NMR (400 MHz, DMSO-d6) δ 8.51 (d, J=2.1 Hz, 1H), 8.34 (s, 3H), 8.03 (dd, J=8.5, 2.4 Hz, 1H), 7.87 (d, J=8.5 Hz, 1H), 6.14 (s, 1H), 4.12 (q, J=5.7 Hz, 2H), 2.59 (s, 3H), 2.21 (s, 3H).

E. (6-(4-chloro-1H-pyrazol-1-yl)pyridin-3-yl)methanamine

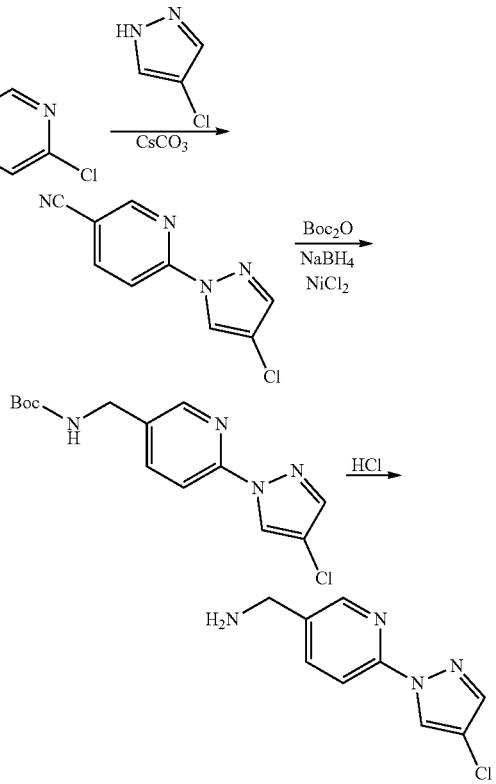

Step 1: Synthesis of 6-(4-Chloro-1H-pyrazol-1-yl)nicotinonitrile

To a solution of 6-chloronicotinonitrile (300 mg, 2.2 mmol) in DMF (10 mL) was added 4-chloro-1H-pyrazole (227 mg, 2.2 mmol) and $Cs_2CO_3$ (1.4 g, 4.4 mmol) and the mixture was stirred at 90° C. for 16 h. The mixture was then diluted with $H_2O$ (25 mL) and filtered. The solids were washed with $H_2O$ and dried under vacuum to give 6-(4-chloro-1H-pyrazol-1-yl)nicotinonitrile (380 mg, 84%), which was used in the next step without further purification.

Step 2: Synthesis of tert-Butyl ((6-(4-chloro-1H-pyrazol-1-yl)pyridin-3-yl)methyl)carbamate To 6-(4-chloro-1H-pyrazol-1-yl)nicotinonitrile (350 mg, 1.7 mmol) in MeOH (10 mL), was added $NiCl_2$ (19 mg, 0.17 mmol), $(Boc)_2O$ (741 mg, 3.4 mmol) and $NaBH_4$ (163 mg, 4.3 mmol), and the mixture was stirred at ambient temperature for 3 h. Saturated aqueous $NH_4Cl$ solution was added, and the MeOH was removed under vacuum. The aqueous suspension was then partitioned with EtOAc, and the organic layer was washed with saturated sodium bicarbonate solution (2×50 mL), dried with anhydrous sodium sulfate, filtered, and concentrated under vacuum to give 480 mg of the title compound, which was used in the next step without further purification.

Step 3: Synthesis of (6-(4-chloro-1H-pyrazol-1-yl)pyridin-3-yl)methanamine

A solution of HCl in dioxane (4.0 M, 10 mL) was added to tort-butyl ((6-(4-chloro-1H-pyrazol-1-yl)pyridin-3-yl)methyl)carbamate (450 mg, 1.5 mmol) at ambient temperature. The mixture was stirred for 2 h, then concentrated under reduced pressure to give the title compound (290 mg) as a light brown solid that was used without further purification. MS: M+1=209.

F. (R)-1-(6-(4-fluoro-1H-pyrazol-1-yl)pyridin-3-yl)ethan-1-amine

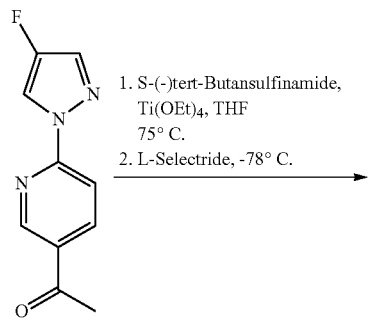

1. S-(−)tert-Butansulfinamide, Ti(OEt)$_4$, THF 75° C.
2. L-Selectride, -78° C.

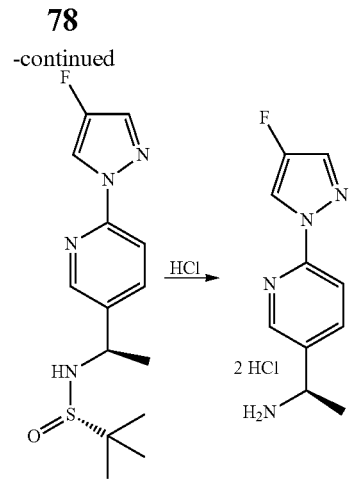

Steps 1-3: (R)-1-(6-(4-fluoro-1H-pyrazol-1-yl)pyridin-3-yl)ethan-1-amine

The title compound was prepared from 1-(6-(4-fluoro-1H-pyrazol-1-yl)pyridin-3-yl)ethan-1-one using the same sequence that was described to prepare the S enantiomer of this compound, except that (R)-(−)-t-Butylsulfinamide was replaced with (S)-(−)-t-Butylsulfinamide as the chiral auxiliary. MS (ES+) $C_{10}H_{11}FN_4$ requires: 206, found: 207 [M+H]$^+$.

The synthetic protocols that can be used to prepare the compounds disclosed herein are indicated below. The NMR and LC MS data obtained for compounds disclosed herein are also shown below.

| Compound Number | Synthetic Protocol | 1H NMR | MS (M + 1) |
|---|---|---|---|
| 100 | 2 | $^1$H NMR (400 MHz, DMSO-d6) δ 8.56 (s, 1H), 8.44 (s, 1H), 8.35 (s, 1H), 7.85 (s, 2H), 7.81 (s, 1H), 6.66 (d, 7 = 15.8 Hz, 1H), 6.57 (s, 1H), 4.36 (s, 2H), 3.17 (s, 3H), 2.21 (d, J = 29.3 Hz, 3H), 2.06 (d, J = 13.0 Hz, 4H), 1.80 (s, 2H), 1.63 (s, 2H). | 472 |
| 101 | 2 | $^1$H NMR (400 MHz, DMSO) δ 8.61 (d, J = 2.5 Hz, 1H), 8.46 (d, J = 6.0 Hz, 1H), 8.36 (s, 1H), 7.91 (d, J = 8.4 Hz, 1H), 7.87-7.84 (m, 1H), 7.82 (s, 1H), 6.72-6.66 (m, 1H), 6.59-6.57 (m, 1H), 4.34 (d, J = 5.8 Hz, 2H), 3.17 (s, 3H), 2.27 (s, 3H), 2.04 (s, 2H), 1.96 (d, J = 11.6 Hz, 2H), 1.59 (dd, J = 27.2, 14.4 Hz, 4H). | 472 |
| 102 | 2 | 1H NMR (400 MHz, DMSO) δ 8.56 (s, 1H), 8.44 (s, 1H), 8.35 (s, 1H), 7.83 (d, J = 15.0 Hz, 3H), 6.66 (d, J = 15.8 Hz, 1H), 6.57 (s, 1H), 4.36 (s, 1H), 3.17 (s, 3H), 2.42 (s, 2H), 2.21 (d, J = 29.3 Hz, 3H), 2.06 (d, J = 13.0 Hz, 4H), 1.78 (d, J = 16.2 Hz, 2H), 1.63 (s, 2H). | 486 |
| 103 | 2 | $^1$H NMR (400 MHz, DMSO-d6) δ 8.61 (d, J = 2.5 Hz, 1H), 8.46 (d, J = 6.0 Hz, 1H), 8.36 (s, 1H), 7.92-7.82 (m, 3H), 6.72-6.66 (m, 1H), 6.58-6.57 (m, 1H), 4.33 (s, 1H), 3.17 (s, 3H), 2.42 (s, 2H), 2.27 (s, 3H), 2.06-1.94 (m, 4H), 1.56 (dd, J = 28.0, 12.9 Hz, 4H). | 486 |
| 104 | 2 | $^1$H NMR (400 MHz, DMSO-d6) δ 14.03 (s, 1H), 12.33 (s, 1H), 8.70-8.31 (m, 4H), 7.86 (d, J = 30.5 Hz, 3H), 6.57 (s, 1H), 4.34 (s, 2H), 2.82 (s, 1H), 2.41 (s, 3H), 2.21 (s, 5H), 1.94 (d, J = 12.4 Hz, 1H), 1.67 (dd, J = 45.4, 19.9 Hz, 5H), 1.24 (s, 1H), 0.94 (d, J = 6.4 Hz, 3H). | 486 |
| 105 | 2 | $^1$H NMR (400 MHz, DMSO-d6) δ 8.64 (s, 1H), 8.46 (s, 1H), 8.35 (s, 1H), 7.92 (d, J = 4.2 Hz, 1H), 7.86 (d, J = 6.5 Hz, 2H), 6.66 (d, J = 21.2 Hz, 1H), 4.36 (s, 2H), 2.91 (s, 1H), 2.42 (s, 2H), 2.21 (d, J = 33.5 Hz, 3H), 2.07 (dd, J = 14.5, 7.1 Hz, 4H), 1.80 (s, 2H), 1.64 (d, J = 11.5 Hz, 2H). | 490 |
| 106 | 2 | $^1$H NMR (400 MHz, DMSO-d6) δ 11.55 (s, 1H), 11.24 (s, 1H), 8.90 (d, J = 5.0 Hz, 1H), 8.44 (s, 1H), 8.33 (s, 1H), 8.01-7.95 (m, 0H), 7.81-7.78 (m, 1H), 6.68 (s, 1H), 6.10 (s, 1H), 5.93 (s, 1H), 4.35 (s, 2H), 2.91 (s, | 500 |

-continued

| Compound Number | Synthetic Protocol | 1H NMR | MS (M + 1) |
|---|---|---|---|
| | | 0H), 2.54 (s, 1H), 2.44 (d, J = 20.0 Hz, 2H), 2.22 (d, J = 22.8 Hz, 5H), 2.13-1.96 (m, 4H), 1.79 (d, J = 8.4 Hz, 2H), 1.62 (s, 2H). | |
| 107 | 1 | ¹H NMR (400 MHz, DMSO-d6) δ 14.57 (s, 1H), 12.87 (s, 1H), 11.57 (s, 1H), 8.61 (d, J = 2.5 Hz, 1H), 8.47-8.35 (m, 2H), 7.94-7.85 (m, 2H), 7.82 (d, J = 1.0 Hz, 1H), 7.11 (s, 1H), 6.95 (s, 1H), 6.58 (dd, J = 2.5, 1.7 Hz, 1H), 6.02 (s, 1H), 5.92 (s, 1H), 4.40-4.29 (m, 2H), 2.45 (s, 3H), 2.31 (s, 1H), 2.27 (s, 3H), 2.05-1.96 (m, 2H), 1.93-1.81 (m, 3H), 1.54 (d, J = 9.9 Hz, 1H), 0.98 (d, J = 7.2 Hz, 3H). | 501 |
| 111 | 2 | ¹H NMR (500 MHz, DMSO-d6) δ 11.85 (s, 1H), 9.43 (s, 1H), 8.64 (d, J = 4.5 Hz, 1H), 8.35 (d, J = 2.2 Hz, 1H), 8.20 (d, J = 7.7 Hz, 1H), 7.92-7.81 (m, 3H), 6.79 (s, 1H), 6.17 (s, 1H), 5.02-4.92 (m, 1H), 2.72 (s, 1H), 2.41-2.31 (m, 1H), 2.27-2.12 (m, 8H), 1.83-1.48 (m, 6H), 1.38 (d, J = 7.1 Hz, 3H). | 504 |
| 113 | 2 | ¹H NMR (400 MHz, DMSO-d6) δ 11.55 (s, 0H), 11.23 (s, 0H), 8.83 (d, J = 4.8 Hz, 0H), 8.74 (s, 0H), 8.46 (s, 0H), 8.36 (s, 0H), 7.95 (s, 0H), 7.90-7.81 (m, 1H), 4.63-4.48 (m, 0H), 4.36 (s, 1H), 2.91 (s, 0H), 2.55 (s, 0H), 2.44 (d, J = 17.9 Hz, 1H), 2.20 (d, J = 32.7 Hz, 1H), 2.12-1.85 (m, 1H), 1.62 (s, 1H). | 506 |
| 114 | 1 | ¹H NMR (400 MHz, DMSO-d6) δ 14.60 (s, 1H), 12.88 (s, 1H), 11.53 (s, 1H), 8.61 (m, 1H), 8.36 (dd, J = 12.9, 7.1 Hz, 2H), 7.90 (m, 2H), 7.82 (d, J = 1.0 Hz, 1H), 7.12 (s, 1H), 6.94 (s, 1H), 6.58 (dd, J = 2.5, 1.7 Hz, 1H), 6.02 (s, 1H), 5.91 (s, 1H), 4.40 (dd, J = 15.2, 5.9 Hz, 2H), 4.30 (m, 2H), 2.45 (s, 3H), 2.27 (s, 3H), 2.17 (d, J = 9.7 Hz, 3H), 1.83 (d, J = 21.1 Hz, 2H), 1.66 (t, J = 16.3 Hz, 2H), 1.13 (s, 3H), 0.94 (s, 3H). | 515 |
| 116 | 2 | ¹H NMR (400 MHz, DMSO-d6) δ 13.88 (s, 1H), 12.46 (s, 1H), 11.37 (d, J = 120.9 Hz, 1H), 8.69 (d, J = 4.4 Hz, 1H), 8.50-8.36 (m, 2H), 7.98-7.86 (m, 2H), 7.59 (s, 0.5H), 6.86 (d, J = 27.8 Hz, 1H), 6.66 (s, 0.5H), 5.91 (s, 0.5H), 5.00 (s, 1H), 2.82 (s, 1H), 2.43 (d, J = 20.6 Hz, 3H), 2.22 (s, 3H), 2.11 (s, 1H), 2.04-1.84 (m, 2H), 1.82-1.57 (m, 3H), 1.54 (d, J = 12.6 Hz, 1H), 1.42 (d, J = 5.1 Hz, 3H), 1.24 (s, 1H), 1.01 (d, J = 6.8 Hz, 1H), 0.80 (s, 1H) | 518 |
| 119 | 1 | ¹H-NMR (400 MHz, DMSO-d6) δ ppm 11.63 (s, 1H), 8.85 (s, 1H), 8.65 (d, 1H, J = 4.4 Hz), 8.36 (d, 1H, J = 2.0 Hz), 8.25 (d, 1H, J = 7.2 Hz), 7.92-7.83 (m, 3H), 6.79 (s, 1H), 6.66 (s, 1H), 6.24 (s, 1H), 5.00 (q, 1H, J = 7.2 Hz), 4.81 (s, 1H), 2.49-2.30 (m, 3H), 2.18 (s, 3H), 2.16 (s, 3H), 1.85-1.53 (m, 4H), 1.50-1.34 (m, 5H). | 519 |
| 124 | 2 | ¹H NMR (400 MHz, DMSO-D6) δ 13.84 (s, 1H), 12.40 (d, J = 48.8 Hz, 1H), 11.52 (s, 1H), 8.68 (d, J = 3.2 Hz, 1H), 8.41 (t, J = 11.2 Hz, 2H), 7.93 (dd, J = 8.4, 2.1 Hz, 2H), 7.89 (dd, J = 8.3, 5.2 Hz, 1H), 6.92 (d, J = 24.0 Hz, 1H), 6.65 (s, 1H), 4.98 (s, 1H), 3.00 (s, 1H), 2.40 (s, 6H), 2.22 (s, 1H), 2.12 (s, 2H), 1.85 (s, 2H), 1.67 (d, J = 15.1 Hz, 2H), 1.42 (d, J = 5.7 Hz, 3H), 1.31 (m, 2H), 1.04 (m, 6H). | 532 |
| 128 | 1 | ¹H NMR (400 MHz, DMSO-d6) δ 14.54 (s, 1H), 12.87 (s, 1H), 11.61 (s, 1H), 8.68 (d, J = 4.5 Hz, 1H), 8.41 (dd, J = 6.4, 2.0 Hz, 1H), 8.31 (dd, J = 28.8, 7.8 Hz, 1H), 7.97-7.86 (m, 3H), 7.09 (s, 1H), 6.96 (s, 1H), 5.92 (d, J = 3.7 Hz, 1H), 5.04 (d, J = 7.3 Hz, 1H), 2.46 (s, 3H), 2.32 (s, 1H), 2.27 (d, J = 5.1 Hz, 3H), 2.12-1.77 (m, 6H), 1.49 (d, J = 10.0 Hz, 1H), 1.42 (d, J = 7.0 Hz, 3H), 1.03 (s, 1H), 0.84 (d, J = 7.2 Hz, 2H). | 534 |
| 129 | 3 | ¹H NMR (400 MHz, DMSO-d6) δ 11.85 (s, 1H), 9.46 (s, 1H), 8.65 (d, J = 4.5 Hz, 1H), 8.48-8.35 (m, 2H), 7.96 (dd, J = 8.5, 2.3 Hz, 1H), 7.89 (d, J = 4.2 Hz, 1H), 7.84 (d, J = 8.5 Hz, 1H), 6.77 (s, 1H), 6.15 (s, 1H), 5.12-5.02 (m, 1H), 3.06 (s, 3H), 2.67 (t, J = 6.4 Hz, 1H), 2.20 (s, 3H), 2.16 (s, 5H), 1.95 (dd, J = 28.8, 9.8 Hz, 2H), 1.87-1.76 (m, 2H), 1.58-1.38 (m, 5H). | 534 |
| 130 | 3 | ¹H NMR (500 MHz, DMSO-d6) δ 11.89 (s, 1H), 9.51 (bs, 1H), 8.68 (dd, J = 4.5, 0.7 Hz, 1H), 8.46 (d, J = 8.5 Hz, 1H), 8.44 (d, J = 2.3 Hz, 1H), 7.99 (dd, J = 8.5, 2.3 Hz, 1H), 7.91 (dd, J = 4.4, 0.8 Hz, 1H), 7.88 (d, J = 8.6 Hz, 1H), 6.86 (bs, 1H), 6.20 (bs, 1H), 5.06 (dq, J = 7.8, 7.6 Hz 1H), 3.14 (s, 3H), 2.58 (bt, J = 12 Hz, 1H), 2.24 (s, 3H), 2.21 (s, 3H), 1.99 (bd, J = 12.1 Hz, 1H), 1.93 | 534 |

-continued

| Compound Number | Synthetic Protocol | 1H NMR | MS (M + 1) |
|---|---|---|---|
| | | (dd, J = 13.8, 2.4 Hz, 1H), 1.88-1.69 (m, 5H), 1.63 (td, J = 14, 4 Hz, 1H), 1.47 (d, J = 7.1 Hz, 3H). | |
| 131 | 3 | ¹H NMR (400 MHz, DMSO-d6) δ 11.88 (s, 1H), 9.51 (s, 1H), 9.12 (d, J = 1.4 Hz, 1H), 8.73 (d, J = 4.4 Hz, 1H), 8.51 (d, J = 1.4 Hz, 1H), 8.41 (d, J = 8.0 Hz, 1H), 8.02 (d, J = 4.1 Hz, 1H), 6.85 (s, 1H), 6.18 (s, 1H), 5.18-5.07 (m, 1H), 3.17 (s, 3H), 2.64-2.52 (m, 1H), 2.23 (s, 3H), 2.19 (s, 3H), 2.02-1.91 (m, 2H), 1.89-1.61 (m, 6H), 1.49 (d, J = 7.1 Hz, 3H). | 535 |
| 135 | 1 | ¹H NMR (400 MHz, DMSO-d6) δ 14.58 (m, 1H), 12.89 (m, 2H), 11.52 (s, 1H), 8.69 (t, J = 4.3 Hz, 1H), 8.43 (d, J = 2.0 Hz, 1H), 8.27 (m, 1H), 7.97 (m, 4H), 7.59 (m, 1H), 7.06 (s, 1H), 6.95 (s, 1H), 5.98 (s, 1H), 5.91 (s, 1H), 5.06 (dd, J = 13.5, 7.0 Hz, 1H), 2.46 (s, 3H), 2.27 (s, 3H), 2.17 (s, 2H), 1.83 (d, J = 29.4 Hz, 2H), 1.62 (s, 2H), 1.52 (d, J = 7.0 Hz, 1H), 1.44 (d, J = 7.1 Hz, 3H), 1.16 (s, 1H), 1.04 (s, 2H), 1.02 (s, 1H), 0.88 (s, 2H). | 547 |
| 136 | 3 | ¹H NMR (400 MHz, DMSO-d6) δ 11.89 (s, 1H), 9.53 (s, 1H), 8.67 (d, J = 4.4 Hz, 1H), 8.41 (d, J = 2.2 Hz, 1H), 8.28 (d, J = 8.2 Hz, 1H), 7.98 (dd, J = 8.5, 2.3 Hz, 1H), 7.93-7.80 (m, 2H), 6.74 (s, 1H), 6.28 (s, 1H), 5.09-4.95 (m, 1H), 3.28-3.20 (m, 2H), 2.61-2.51 (m, 1H), 2.22 (s, 3H), 2.19 (s, 3H), 2.02-1.91 (m, 2H), 1.90-1.78 (m, 2H), 1.71 (d, J = 10.4 Hz, 3H), 1.63-1.51 (m, 1H), 1.45 (d, J = 7.1 Hz, 3H), 1.21 (t, J = 6.9 Hz, 3H). | 548 |
| 137 | 1 | ¹H NMR (400 MHz, DMSO-d6) δ 11.71 (s, 1H), 8.91 (s, 1H), 8.64 (d, J = 4.5 Hz, 1H), 8.48-8.36 (m, 2H), 7.97 (dd, J = 8.5, 2.3 Hz, 1H), 7.89 (d, J = 4.2 Hz, 1H), 7.83 (d, J = 8.5 Hz, 1H), 6.70 (s, 1H), 6.68 (s, 1H), 6.17 (s, 1H), 5.17-5.08 (m, , 1H), 4.88 (s, 1H), 3.08 (s, 3H), 2.25-2.15 (m, 7H), 2.02-1.73 (m, 6H), 1.59-1.48 (m, 2H), 1.45 (d, J = 7.0 Hz, 3H). | 549 |
| 138 | 1 | ¹H NMR (400 MHz, DMSO-d6) δ 11.67 (s, 1H), 8.96 (s, 1H), 8.68 (d, J = 4.5 Hz, 1H), 8.48 (d, J = 8.3 Hz, 1H), 8.43 (d, J = 2.2 Hz, 1H), 7.99 (dd, J = 8.6, 2.3 Hz, 1H), 7.94-7.81 (m, 2H), 6.77 (s, 1H), 6.67 (s, 1H), 6.39 (s, 1H), 5.09-5.01 (m, 1H), 4.84 (s, 1H), 3.18 (s, 3H), 2.29-2.03 (m, 9H), 1.97 (td, J = 13.7, 3.5 Hz, 1H), 1.72 (dd, J = 20.5, 14.9 Hz, 2H), 1.46 (d, J = 7.0 Hz, 3H), 1.40-1.26 (m, 2H). | 549 |
| 141 | 1 | ¹H NMR (400 MHz, DMSO-d6) δ 11.64 (s, 1H), 9.01 (s, 1H), 8.64 (d, J = 4.5 Hz, 1H), 8.55 (d, J = 8.3 Hz, 1H), 8.40 (d, J = 2.3 Hz, 1H), 7.97 (dd, J = 8.5, 2.4 Hz, 1H), 7.89 (d, J = 4.2 Hz, 1H), 7.84 (d, J = 8.5 Hz, 1H), 6.78 (s, 1H), 6.66 (s, 1H), 6.27 (s, 1H), 5.14 (t, J = 7.5 Hz, 1H), 3.10 (s, 3H), 2.45-2.29 (m, 2H), 2.20 (s, 3H), 2.16 (s, 3H), 2.14-2.01 (m, 2H), 1.91-1.68 (m, 4H), 1.46 (d, J = 7.1 Hz, 3H). | 551 |
| 142 | 1 | ¹H NMR (400 MHz, DMSO-d6) δ 11.71 (s, 1H), 9.11 (s, 1H), 8.67 (d, J = 4.5 Hz, 1H), 8.56 (d, J = 8.3 Hz, 1H), 8.43 (d, J = 2.2 Hz, 1H), 7.99 (dd, J = 8.5, 2.3 Hz, 1H), 7.93-7.84 (m, 2H), 6.77 (s, 1H), 6.63 (s, 1H), 6.32 (s, 1H), 5.10-05.13 (m, 1H), 3.20 (s, 3H), 2.43-2.15 (m, 8H), 2.06-1.81 (m, 4H), 1.78-1.61 (m, 2H), 1.47 (d, J = 7.1 Hz, 3H). | 551 |
| 144 | 2 | ¹H NMR (500 MHz, DMSO-d6) δ 11.89 (s, 1H), 9.48 (s, 1H), 8.67 (d, J = 4.5 Hz, 1H), 8.49-8.30 (m, 2H), 7.96-7.77 (m, 3H), 7.09 (d, J = 7.4 Hz, 1H), 6.81 (s, 1H), 6.19 (s, 1H), 5.01 (q, J = 7.0 Hz, 1H), 3.16 (d, J = 4.9 Hz, 1H), 2.75 (t, J = 18.9 Hz, 1H), 2.41-2.28 (m, 2H), 2.25 (d, J = 1.9 Hz, 3H), 2.20 (s, 3H), 2.10-1.87 (m, 1H), 1.65-1.49 (m, 2H), 1.41 (dd, J = 7.0, 2.0 Hz, 3H). | 502 |
| 146 | 1 | ¹H NMR (400 MHz, DMSO-d6) δ 11.68 (s, 1H), 8.91 (s, 1H), 8.69 (d, J = 4.4 Hz, 1H), 8.44 (d, J = 2.3 Hz, 1H), 8.18 (d, J = 8.2 Hz, 1H), 7.99 (dd, J = 8.6, 2.4 Hz, 1H), 7.93-7.87 (m, 2H), 6.90 (s, 1H), 6.84 (s, 1H), 6.12 (s, 1H), 5.22 (s, 1H), 5.08 (dt, J = 14.5, 7.2 Hz, 1H), 3.93-3.81 (m, 2H), 3.72-3.63 (m, 1H), 2.30-2.23 (m, 1H), 2.21 (s, 3H), 2.19 (s, 3H), 1.84-1.74 (m, 2H), 1.74-1.65 (m, 1H), 1.47 (d, J = 7.0 Hz, 3H). | 521 |
| 147 | 1 | ¹H-NMR (400 MHz, CD₃OD): δ ppm 8.53-8.51 (m, 2H), 8.43 (d, J = 7.6 Hz, 1H), 8.04-8.02 (m, 1H), 7.95 (d, J = 8.8 Hz, 1H), 7.71 (d, J = 4.0 Hz, 1H), 7.01 (s, 1H), 6.72 (s, 1H), 5.91 (s, 1H), 5.18-5.15 (m, 1H), 4.19 (d, J = 11.6 Hz, 1H), 3.60 (d, J = 12.0 Hz, 1H), 2.38 (s, 3H), 2.38-2.29 (m, 1H), 2.29 (s, 3H), 2.18-2.13 (m, 1H), | 535 |

-continued

| Compound Number | Synthetic Protocol | 1H NMR | MS (M + 1) |
|---|---|---|---|
| 148 | 1 | 1.81-1.78 (m, 1H), 1.59 (d, J = 7.2 Hz, 3H), 1.59-1.51 (m, 1H), 1.51 (s, 3H).<br>$^1$H-NMR (400 MHz, CD$_3$OD): δ ppm 8.52 (d, J = 4.4 Hz, 1H), 8.47 (d, J = 9.2 Hz, 1H), 7.99-7.93 (m, 2H), 7.71 (d, J = 4.0 Hz, 1H), 7.08 (s, 1H), 6.76 (s, 1H), 5.88 (s, 1H), 5.19-5.16 (m, 1H), 4.21 (d, J = 12.0 Hz, 1H), 3.70 (d, J = 12.0 Hz, 1H), 2.41 (s, 3H), 2.41-2.30 (m, 1H), 2.30 (s, 3H), 2.30-2.22 (m, 1H), 1.92-1.87 (m, 1H), 1.64 (d, J = 7.2 Hz, 3H), 1.63-1.46 (m, 1H), 1.46 (s, 3H). | 535 |
| 149 | 4 | $^1$H NMR (500 MHz, DMSO-d6) δ 11.74 (s, 1H), 9.13 (s, 1H), 8.67 (d, J = 4.4 Hz, 1H), 8.47 (d, J = 8.3 Hz, 1H), 8.42 (d, J = 2.3 Hz, 1H), 7.98 (dd, J = 8.5, 2.3 Hz, 1H), 7.90 (d, J = 4.2 Hz, 1H), 7.86 (d, J = 8.5 Hz, 1H), 6.51 (s, 1H), 6.50 (s, 1H), 5.04 (p, J = 7.6 Hz, 1H), 3.13 (s, 3H), 2.27 (s, 3H), 2.19 (s, 3H), 1.95 (dd, J = 29.5, 11.6 Hz, 2H), 1.84-1.54 (m, 7H), 1.45 (d, J = 7.1 Hz, 3H). | 534 |
| 150 | 3 | $^1$H NMR (400 MHz, DMSO) δ 11.88 (s, 1H), 9.50 (s, 1H), 9.11 (d, J = 1.4 Hz, 1H), 8.72 (d, J = 4.4 Hz, 1H), 8.64 (t, J = 6.0 Hz, 1H), 8.39 (d, J = 1.4 Hz, 1H), 8.02 (d, J = 4.2 Hz, 1H), 6.85 (s, 1H), 6.17 (s, 1H), 4.48 (d, J = 5.9 Hz, 2H), 3.19 (s, 3H), 2.64-2.53 (m, 1H), 2.23 (s, 3H), 2.19 (s, 3H), 1.96 (d, J = 14.2 Hz, 2H), 1.86-1.67 (m, 6H). | 521 |
| 151 | 3 | $^1$H NMR (400 MHz, DMSO) δ 11.88 (s, 1H), 9.50 (s, 1H), 8.66 (d, J = 4.4 Hz, 1H), 8.46 (d, J = 8.3 Hz, 1H), 8.41 (d, J = 2.2 Hz, 1H), 7.98 (dd, J = 8.5, 2.3 Hz, 1H), 7.92-7.82 (m, 2H), 6.84 (s, 1H), 6.18 (s, 1H), 5.08-5.01 (m, 1H), 3.12 (s, 3H), 2.61-2.51 (m, 1H), 2.22 (s, 3H), 2.19 (s, 3H), 2.00-1.87 (m, 2H), 1.83-1.56 (m, 6H), 1.45 (d, J = 7.1 Hz, 3H). | 534 |

Example 10: Measurement of Biochemical Activity of Compounds

In order to assess the activity of chemical compounds against the relevant kinase of interest, the Caliper Life-Sciences electrophoretic mobility shift technology platform was used. Fluorescently labeled substrate peptide was incubated in the presence of kinase and ATP so that a reflective proportion of the peptide was phosphorylated. At the end of the reaction, the mix of phosphorylated (product) and non-phosphorylated (substrate) peptides were passed through the microfluidic system of the Caliper EZ Reader 2, under an applied potential difference. The presence of the phosphate group on the product peptide provides a difference in mass and charge between those of the substrate peptide, resulting in a separation of the substrate and product pools in the sample. As the pools pass a LEDS within the instrument, these pools are detected and resolved as separate peaks. The ratio between these peaks therefore reflects the activity of the chemical matter at that concentration in that well, under those conditions.

A. RET Wild Type Assay at KM

In each well of a 384-well plate, 7.5 nM-10 nM of wild type RET (ProQinase 1090-0000-1) was incubated in a total of 12.5 μL of buffer (100 mM HEPES pH 7.5, 0.015% BriJ 35, 10 mM MgCl$_2$, 1 mM DTT) with 1 μM CSKtide (FITC-AHA-KKKKD DIYFFFG-NH2) and 25 μM ATP at 25° C. for 120 minutes in the presence or absence of a dosed concentration series of compound (1% DMSO final concentration). The reaction was stopped by the addition of 70 μL of Stop buffer (100 mM HEPES pH 7.5, 0.015% Brij 35.35 mM EDTA and 0.2% of Coating Reagent 3 (Caliper Lifesciences)). The plate was then read on a Caliper EZReader 2 (protocol settings: −1.7 psi, upstream voltage −500, downstream voltage −3000, post sample sip 35s). Data was normalized to 0% and 100% inhibition controls and the IC$_{50}$ calculated using a 4-parameter fit in the CORE LIMS.

B. RET V804L Gatekeeper mutant assay at KM

In each well of a 384-well plate, 7.5 nM-10 nM of mutant RET (ProQinase 1096-0000-1) was incubated in a total of 12.5 μL of buffer (100 mM HEPES pH 7.5, 0.015% BriJ 35, 10 mM MgCl2, 1 mM DTT) with 1 μM CSKtide (FITC-AHA-KKKKDDIYFFFG-NH2) and 10 μM ATP at 25° C. for 120 minutes in the presence or absence of a dosed concentration series of compound (1% DMSO final concentration). The reaction was stopped by the addition of 70 μL of Stop buffer (100 mM HEPES pH 7.5, 0.015% Brij 35.35 mM EDTA and 0.2% of Coating Reagent 3 (Caliper Lifesciences)). The plate was then read on a Caliper EZReader 2 (protocol settings: −1.7 psi, upstream voltage −500, downstream voltage −3000, post sample sip 35s). Data was normalized to 0% and 100% inhibition controls and the IC$_{50}$ calculated using a 4-parameter fit in the CORE LIMS.

In the Table below, the following designations are used: <10.00 nM=A; 10.01-100.0 nM=B; and >100 nM=C.

| Compound Number | Wild-type RET | V804L Mutant |
|---|---|---|
| 100 | C | C |
| 101 | A | A |
| 102 | C | C |
| 103 | A | A |
| 104 | C | C |
| 105 | B | B |
| 106 | A | B |
| 107 | A | A |
| 109 | A | A |
| 110 | B | B |

-continued

| Compound Number | Wild-type RET | V804L Mutant |
| --- | --- | --- |
| 111 | B | A |
| 112 | A | A |
| 113 | A | A |
| 114 | A | A |
| 116 | C | B |
| 119 | C | C |
| 120 | A | A |
| 121 | A | A |
| 122 | B | B |
| 124 | C | B |
| 128 | A | A |
| 129 | C | C |
| 130 | A | A |
| 131 | A | A |
| 135 | B | B |
| 136 | A | A |
| 137 | C | C |
| 138 | A | A |
| 141 | B | B |
| 142 | A | A |
| 144 | A | A |
| 146 | A | A |
| 147 | B | B |
| 148 | A | A |
| 149 | B | B |
| 150 | A | A |
| 151 | A | A |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound which is:

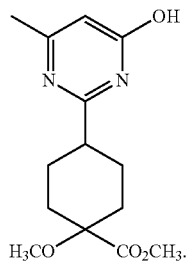

2. A compound which is:

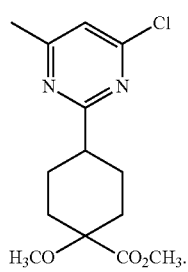

* * * * *